US012279954B2

(12) United States Patent
Arcaro et al.

(10) Patent No.: US 12,279,954 B2
(45) Date of Patent: *Apr. 22, 2025

(54) TRANSCATHETER DEPLOYMENT SYSTEMS AND ASSOCIATED METHODS

(71) Applicant: W. L. Gore & Associates, Inc., Newark, DE (US)

(72) Inventors: David J. Arcaro, Flagstaff, AZ (US); Jason T. Alger, Flagstaff, AZ (US); Dustin V. Dienno, Flagstaff, AZ (US); Joshua C. Haarer, Flagstaff, AZ (US); Edward J. Hoopingarner, Flagstaff, AZ (US); Patrick M. Norris, Flagstaff, AZ (US); Benjamin A. Smith, Flagstaff, AZ (US); Olga Baykova, Flagstaff, AZ (US); Russell L. Jacoby, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1035 days.

This patent is subject to a terminal disclaimer.

(21) Appl. No.: 17/238,649

(22) Filed: Apr. 23, 2021

(65) Prior Publication Data

US 2021/0307905 A1 Oct. 7, 2021

Related U.S. Application Data

(63) Continuation of application No. 16/129,657, filed on Sep. 12, 2018, now Pat. No. 10,987,218.

(Continued)

(51) Int. Cl.
*A61F 2/24* (2006.01)
*A61F 2/95* (2013.01)

(52) U.S. Cl.
CPC .......... *A61F 2/2439* (2013.01); *A61F 2/2436* (2013.01); *A61F 2/95* (2013.01);
(Continued)

(58) Field of Classification Search
CPC ...... A61F 2/2427; A61F 2/243; A61F 2/2436; A61F 2/2439; A61F 2/95; A61F 2002/9505; A61F 2002/9511
See application file for complete search history.

(56) References Cited

U.S. PATENT DOCUMENTS

| 654,799 A | 7/1900 | Levett |
| 3,739,402 A | 6/1973 | Kahn et al. |

(Continued)

FOREIGN PATENT DOCUMENTS

| AU | 2013363172 A1 | 7/2015 |
| AU | 2017202405 A1 | 4/2017 |

(Continued)

OTHER PUBLICATIONS

Forward citations for E12 obtained from: https://scholar.google.com/scholar?cites-5981833429320176658&assdt=2005&sciodt=0,5&hl= en.

(Continued)

*Primary Examiner* — Diane D Yabut

(57) ABSTRACT

Various examples relate to a transcatheter delivery system including a sheath, a delivery catheter, and an implantable device (e.g., a prosthetic valve, a stent, a stent graft, occluder, or vascular filter) maintained in a collapsed configuration by the delivery catheter. The delivery catheter includes a plurality of fiber guides separated by one or more reduced profile sections each having a smaller transverse outer profile than the transverse outer profiles of the fiber guides.

17 Claims, 48 Drawing Sheets

Related U.S. Application Data

(60) Provisional application No. 62/682,692, filed on Jun. 8, 2018, provisional application No. 62/579,756, filed on Oct. 31, 2017, provisional application No. 62/579,762, filed on Oct. 31, 2017.

(52) U.S. Cl.
CPC ........... *A61F 2/2412* (2013.01); *A61F 2/2418* (2013.01); *A61F 2/243* (2013.01); *A61F 2002/9511* (2013.01); *A61F 2/9517* (2020.05); *A61F 2/9522* (2020.05); *A61F 2230/0054* (2013.01); *A61F 2230/0078* (2013.01); *A61F 2250/0039* (2013.01)

(56) References Cited

U.S. PATENT DOCUMENTS

| | | |
|---|---|---|
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |

(56) References Cited

U.S. PATENT DOCUMENTS

| | | |
|---|---|---|
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,278,399 B2 | 3/2022 | Liu |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |

(56) References Cited

U.S. PATENT DOCUMENTS

| | | |
|---|---|---|
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0294248 A1 | 11/2008 | Yang et al. |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |

(56) References Cited

U.S. PATENT DOCUMENTS

| | | |
|---|---|---|
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0052107 A1* | 2/2014 | Voeller .............. A61M 25/0013 604/525 |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1* | 11/2014 | Bakis .................... A61F 2/2436 623/2.11 |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0100939 A1 | 4/2016 | Armstrong et al. |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1* | 9/2016 | Lim ......................... A61F 2/95 623/1.11 |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1* | 3/2017 | Johnson ................ A61F 2/2436 |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0128209 A1 | 5/2017 | Morriss et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0189175 A1 | 7/2017 | Justino et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0311039 A1* | 11/2018 | Cohen .................... A61F 2/2418 |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |

(56) References Cited

FOREIGN PATENT DOCUMENTS

| | | |
|---|---|---|
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |

(56) References Cited

FOREIGN PATENT DOCUMENTS

| | | |
|---|---|---|
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2014/149319 A1 | 9/2014 |
| WO | 2014/181188 A2 | 11/2014 |
| WO | 2014/210124 A1 | 12/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2017/218375 A1 | 12/2017 |
| WO | 2018/029680 A1 | 2/2018 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |
| WO | 2019/246268 A1 | 12/2019 |

OTHER PUBLICATIONS

Google Image Search Results, "S-Shaped", accessed Nov. 1, 2013.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Certified Copy of Priority Document for U.S. Appl. No. 61/739,721, received by the International Bureau Jan. 3, 2014, 1 page.
Certified Copy of the Application Data Sheet, Drawings, Specification, Claims, and Abstract filed under U.S. Appl. No. 13/843,196, filed Mar. 15, 2013, 52 pages.
Clough, Norman E. Introducing a New Family of GORE ePTFE Fibers (2007), pp. 1-10.
English translation of RU2434604 (C1), filed Apr. 30, 2010, translation powered by EPO and Google, 8 pages.
International Preliminary Report on Patentability received for PCT Patent Application No. PCT/US2018/050768, mailed on May 14, 2020, 8 pages.
International Preliminary Report on Patentability received for PCT Patent Application No. PCT/US2018/050786, mailed on Apr. 23, 2020, 9 pages.
International Search Report and Written Opinion from PCT/US2018/050768, mailed Dec. 17, 2018, 12 pages.
International Search Report and Written Opinion from PCT/US2018/050786 mailed Dec. 14, 2018, 13 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of GORE (Trademark) ePTFE Fibers (2007).
Opposition from EP16196687.4, mailed on Dec. 12, 2019, 38 pages.
Opposition from EP17187595.8, filed Sep. 12, 2019, 50 pages.
Cardiac Surgery in the Adult, Third Edition, Chapter 2 2008.
EPO Form 1002 for EP16196687.4 Filed Dec. 28, 2016.

* cited by examiner

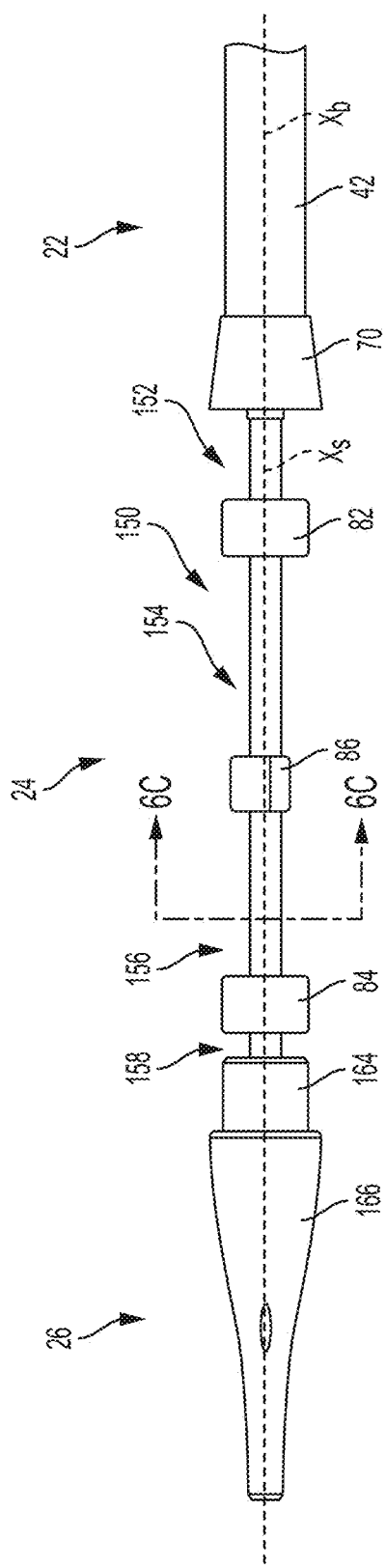
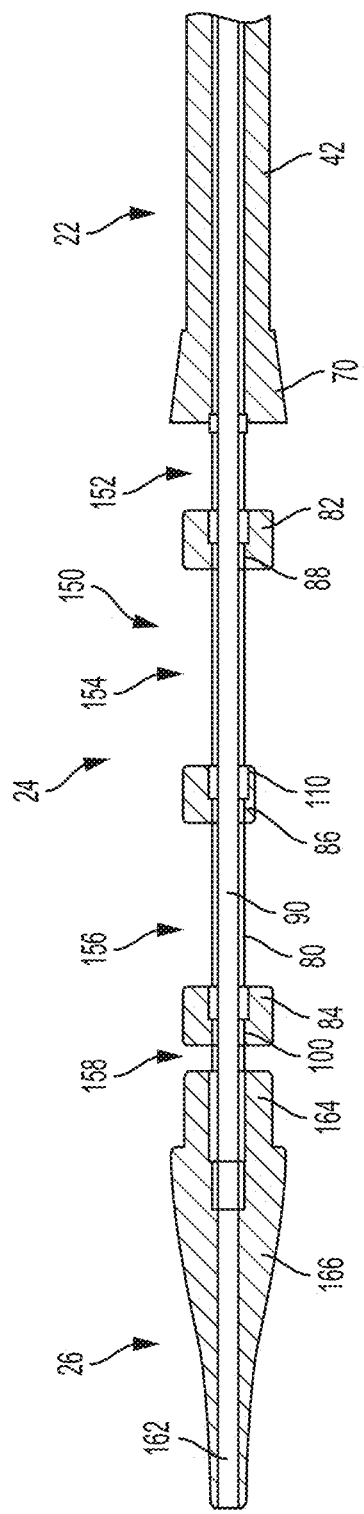

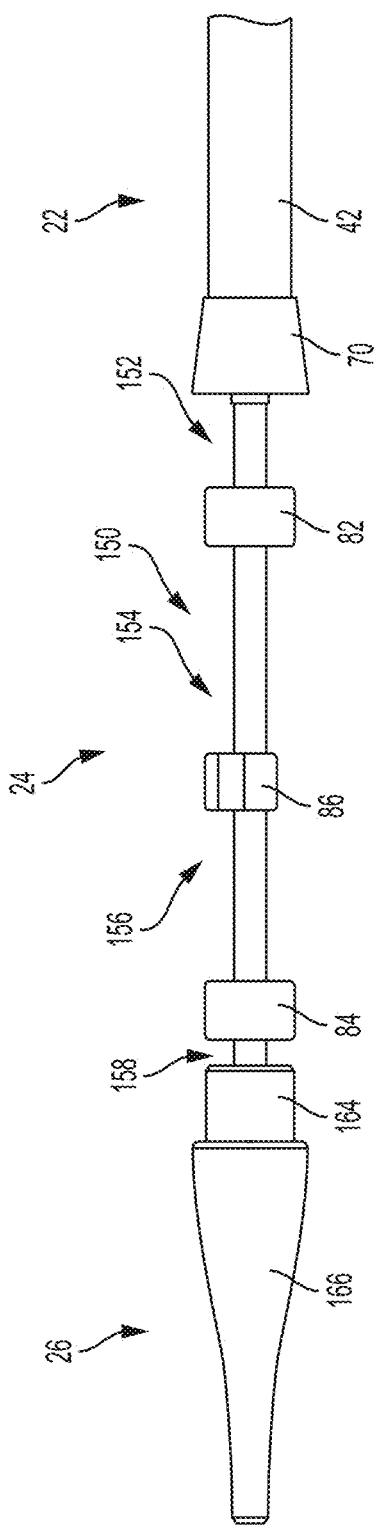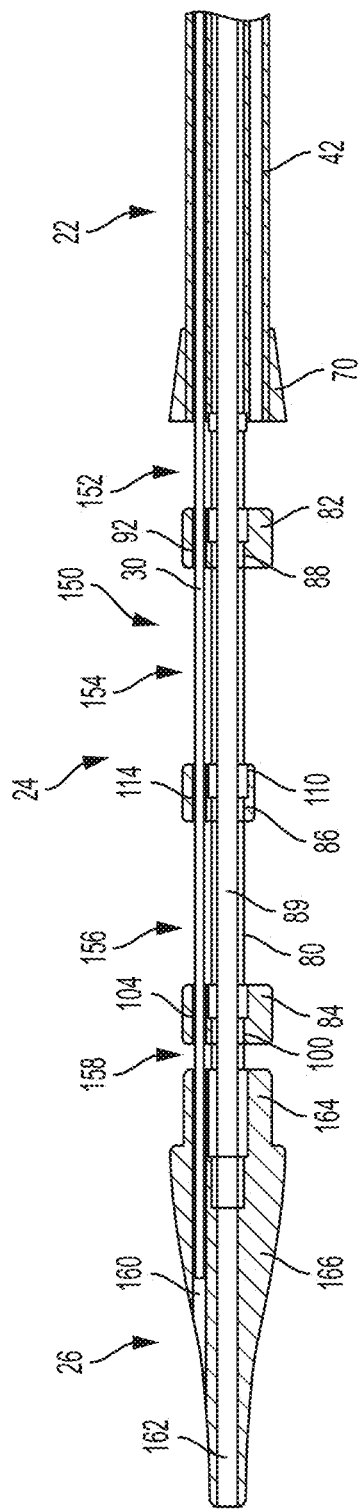
FIG. 6A
FIG. 6B

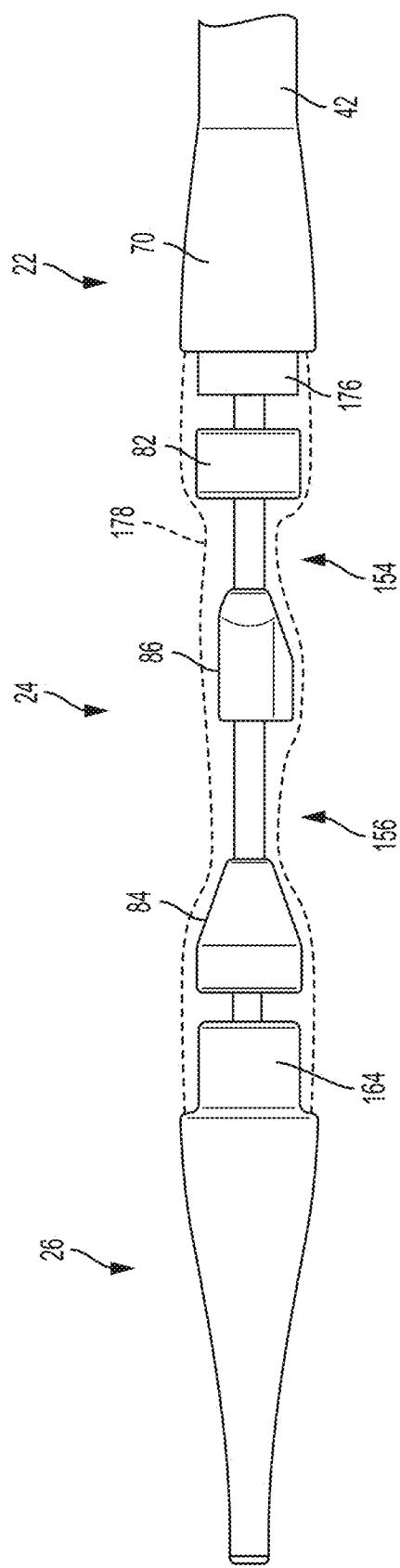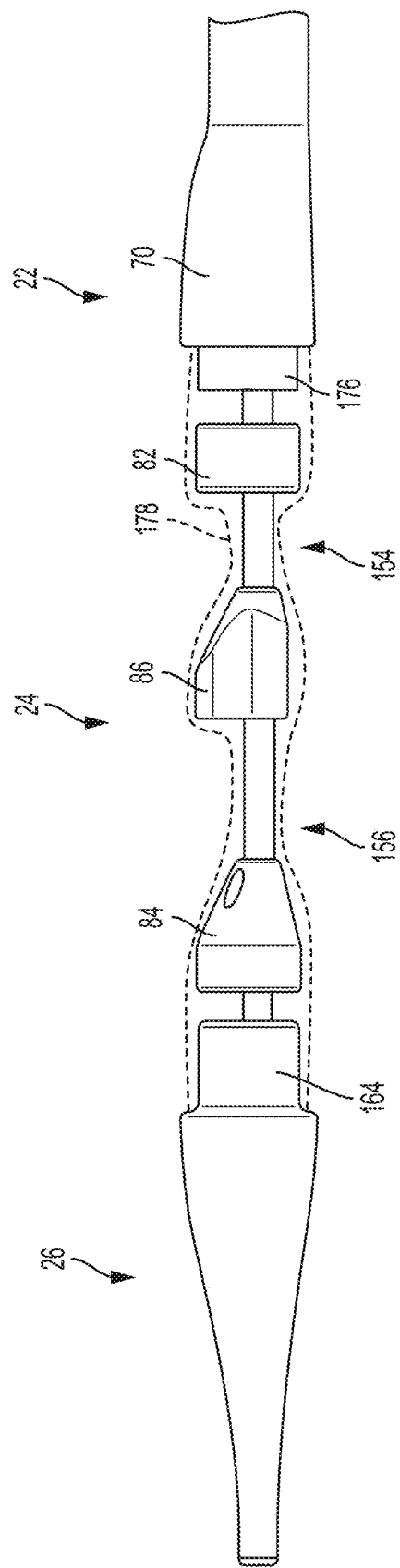
FIG. 7A
FIG. 7B

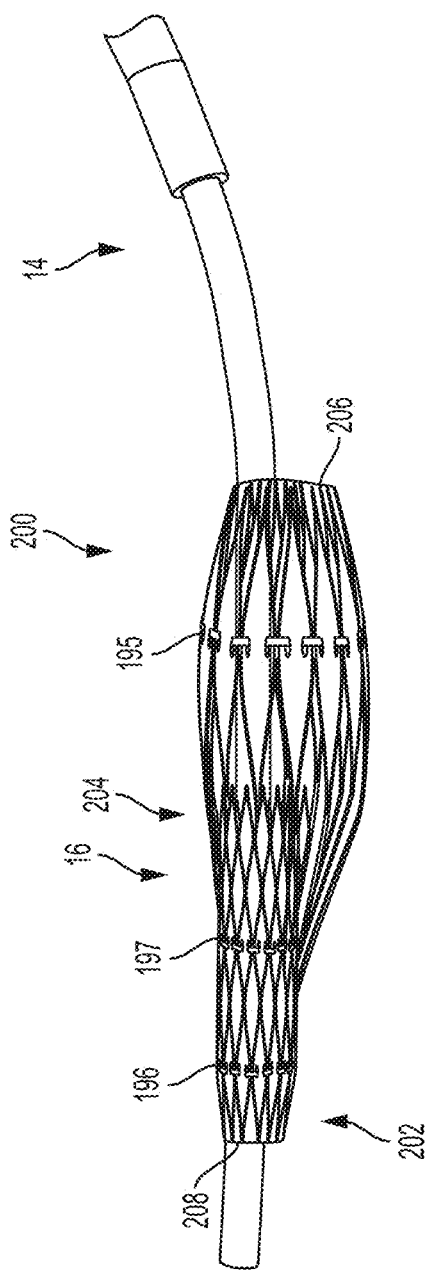
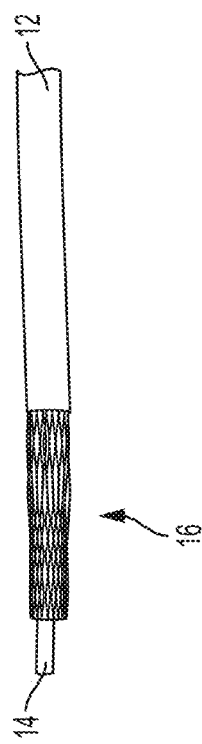
FIG. 14A
FIG. 14B

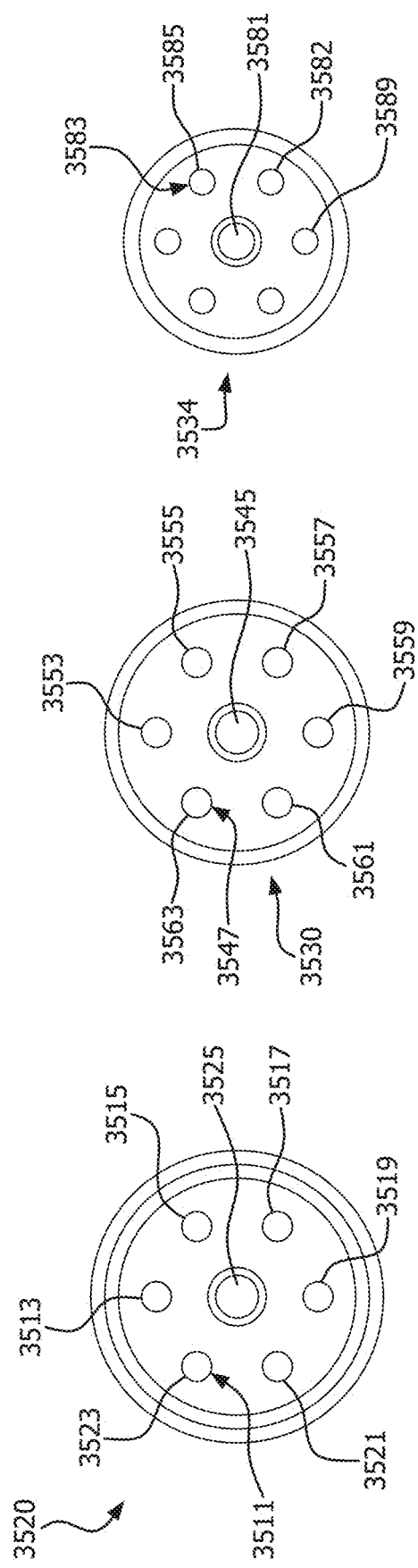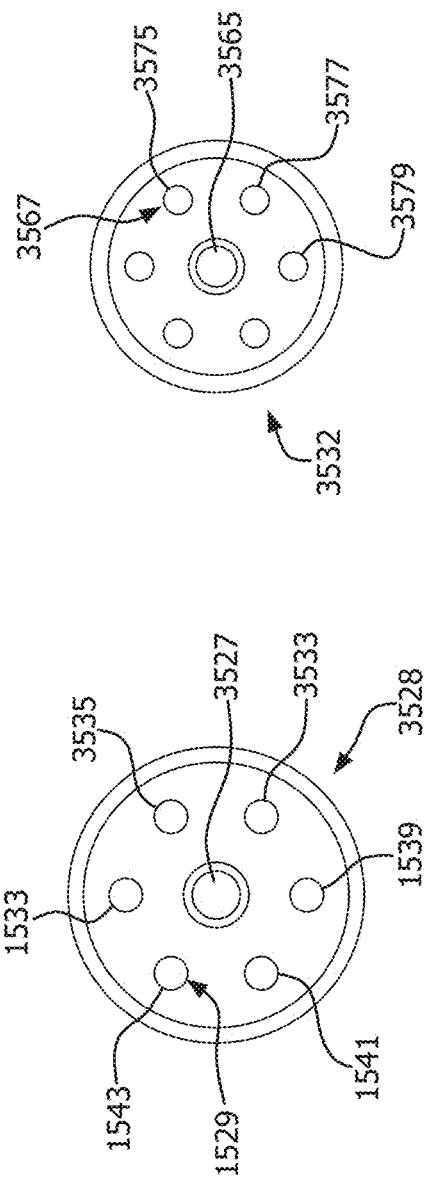

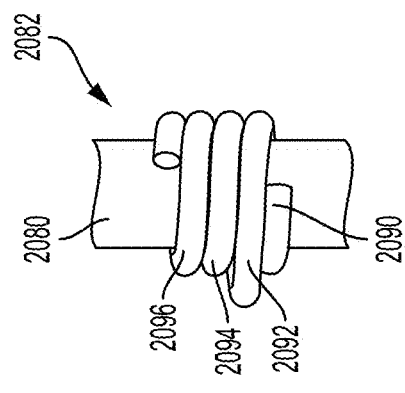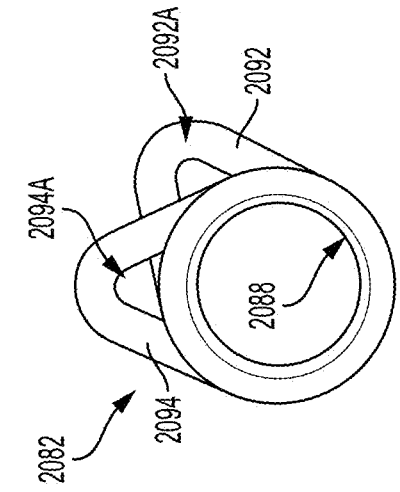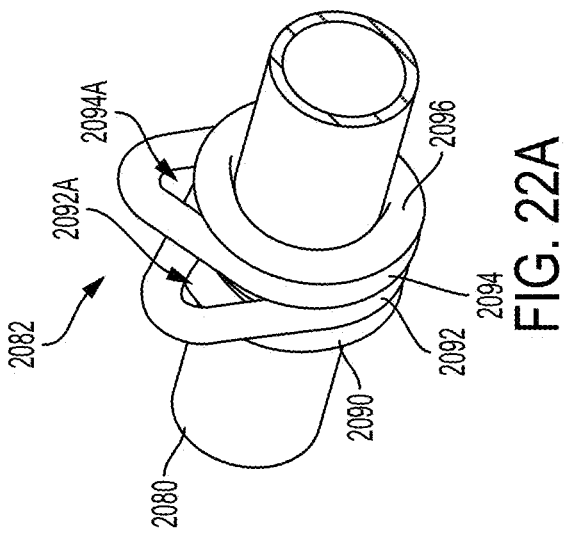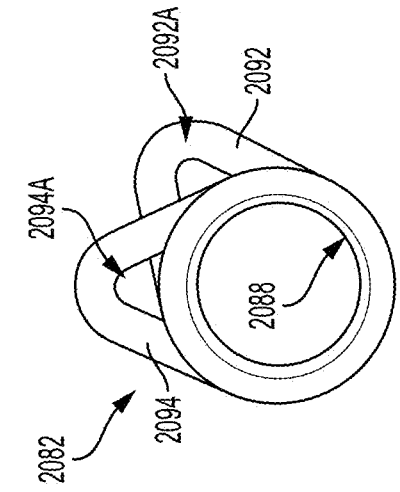

TRANSCATHETER DEPLOYMENT SYSTEMS AND ASSOCIATED METHODS

CROSS-REFERENCE TO RELATED APPLICATIONS

This application is a continuation of U.S. application Ser. No. 16/129,657, filed Sep. 12, 2018, now U.S. Pat. No. 10,987,218, issued Apr. 27, 2021, which claims the benefit of U.S. Provisional Application No. 62/579,756 filed Oct. 31, 2017, U.S. Provisional Application No. 62/579,762, filed Oct. 31, 2017, and U.S. Provisional Application No. 62/682,692, filed Jun. 8, 2018, all of which are incorporated herein by reference in their entireties for all purposes.

BACKGROUND

Depending on device design and the delivery system used, implantable devices, such as prosthetic valves, are deliverable to a treatment site using a variety of methods. As one example, U.S. Pat. No. 9,629,718 to Gloss et al., issued Apr. 25, 2017, is directed to a system that includes a prosthetic valve having a self-expanding frame and a holder configured to retain the frame of the prosthetic valve in a constricted configuration and to control expansion of the frame. According to Gloss et al., the holder has a controllably constrictable and expandable loop, wherein the loop is disposed about at least a portion of the self-expanding frame such that constriction or expansion of the first loop controls constriction or expansion of the frame.

Advances over existing and contemplated transcatheter delivery systems in the pertinent field remain to be realized.

SUMMARY

Various examples relate to a transcatheter delivery system including a sheath, a delivery catheter, and an implantable device (e.g., a prosthetic valve, a stent, a stent graft, occluder, or vascular filter) maintained in a collapsed configuration by the delivery catheter. The delivery catheter includes a plurality of fiber guides separated by one or more reduced profile sections each having a smaller transverse outer profile than the transverse outer profiles of the fiber guides.

According to one example ("Example 1"), a transcatheter delivery system includes a delivery catheter for use with an implantable device. The delivery catheter includes a body portion, a support portion extending from the body portion, a proximal constraint and a distal constraint. The support portion has a longitudinal axis and includes a proximal guide having a constraint passage and a transverse outer profile and a distal guide having a constraint passage, and, optionally a stake member passage, and the distal guide defining a transverse outer profile. The delivery catheter also has a first reduced profile section located intermediate the proximal guide and the distal guide, the first reduced section having a smaller transverse outer profile than the transverse outer profile of the proximal guide and the transverse outer profile of the distal guide. The proximal constraint extends longitudinally from the body portion through the constraint passage of the proximal guide and radially from the constraint passage of the proximal guide. The proximal constraint is secured in a releasable, looped configuration to define a proximal constraining loop. The distal constraint extends longitudinally from the body portion through the constraint passage of the distal guide and radially from the constraint passage of the distal guide. The distal constraint is secured in a releasable, looped configuration to define a distal constraining loop.

According to another example ("Example 2") further to Example 1, the constraint passage of the proximal guide is at an angular position relative to the longitudinal axis of the support portion and the constraint passage of the distal guide is at an angular position relative to the longitudinal axis of the support portion that is different than the angular position of the constraint passage of the proximal guide.

According to another example ("Example 3") further to Examples 1 or 2, the transverse outer profile of the first reduced profile section is at least 10% smaller than the transverse outer profile of the proximal guide and the transverse outer profile of the distal guide.

According to another example ("Example 4") further to any of Examples 1 to 3, the transverse outer profile of the first reduced profile section is at least 20% smaller than the transverse outer profile of the proximal guide and the transverse outer profile of the distal guide.

According to another example ("Example 5") further to any of Examples 1 to 4, the transverse outer profile of the first reduced profile section is at least 50% smaller than the transverse outer profile of the proximal guide and the transverse outer profile of the distal guide.

According to another example ("Example 6") further to any of Examples 1 to 5, the support portion further includes an intermediate guide having a transverse outer profile and a constraint passage, the intermediate guide being longitudinally-spaced from the proximal guide and the distal guide and being located intermediate the proximal guide and the distal guide, the constraint passage of the intermediate guide being at an angular position relative to the longitudinal axis of the support portion. The support portion further includes a second reduced profile section extending between the distal guide and the intermediate guide, the second reduced profile section having a smaller transverse outer profile than the transverse outer profile of the distal guide and the transverse outer profile of the intermediate guide, wherein the first reduced profile section is located between the proximal guide and the intermediate guide. And, the transcatheter delivery system further comprises an intermediate constraint extending longitudinally from the body portion through the constraint passage of the intermediate guide and radially from the constraint passage of the intermediate guide, the intermediate constraint secured in a releasable, looped configuration to define an intermediate constraining loop.

According to another example, ("Example 7"), further to any of Examples 1 to 6, the transverse outer profile of the second reduced profile section is at least 50% smaller than the transverse outer profile of the distal guide and the transverse outer profile of the intermediate guide.

According to another example, ("Example 8"), further to any of Examples 1 to 7, the angular position of the constraint passage of the proximal guide is angularly offset from the angular position of the constraint passage of the distal guide by 10 to 350 degrees.

According to another example ("Example 9"), further to any of Examples 6 to 8, the angular position of the constraint passage of the intermediate guide is angularly offset from the angular position of the constraint passage of the distal guide by 10 to 350 degrees.

According to another example ("Example 10"), further to any of Examples 6 to 9, the intermediate guide defines a transverse outer profile that is at least 50% smaller than the transverse outer profile of proximal guide and the transverse outer profile of the distal guide.

According to another example ("Example 11"), further to any of Examples 1 to 10, the transcatheter delivery system further includes a stake member releasably securing at least one of the proximal constraint in the releasable, looped configuration and the distal constraint in the releasable, looped configuration such that the stake member is operable to release at least one of the proximal and distal constraining loops.

According to another example ("Example 12"), further to any of Examples 1 to 11, the transcatheter delivery system further includes a tip portion having a distal nose section and a proximal support section, the proximal support section having a reduced transverse outer profile that defines a recess configured to receive and support an end portion of a prosthetic valve in a compressed, delivery state; and/or the proximal guide is a support guide that has a stepped distal end that defines a support surface for receiving an end portion of the prosthetic valve in the compressed, delivery state.

According to another example ("Example 13"), further to any of Examples 1 to 12, the transcatheter delivery system further includes a prosthetic valve maintained in a compacted delivery configuration by the proximal constraining loop and the distal constraining loop, the prosthetic valve including a frame portion that is expandable and a leaflet construct supported by the frame portion to define a leaflet region of the prosthetic valve, and further wherein the leaflet region is positioned on the support portion between the proximal guide and the distal guide.

According to another example ("Example 14") further to Example 13, the leaflet region does not extend beyond the proximal guide and the distal guide.

According to another example ("Example 15") further to Example 13 or Example 14, the distal guide is tapered proximally in transverse outer profile for receiving a distal end of the leaflet region.

According to another example ("Example 16") further to any of Examples 13 to 15, the frame portion of the prosthetic valve has a distal end and a proximal end and includes a plurality of rows of frame members defining an undulating pattern of alternating distal-facing apices and proximal-facing apices, the plurality of rows of frame members including a distal row at the distal end of the frame portion and a proximal row at the proximal end of the frame portion, and further wherein the distal constraining loop circumscribes the distal row at a position proximal to the distal-facing apices of the distal row and the proximal constraining loop circumscribes the proximal row at a position distal to the proximal-facing apices of the proximal row.

According to another example ("Example 17") further to any of Examples 13 to 16, the frame portion of the prosthetic valve has a distal end and a proximal end and includes a plurality of rows of closed cells defined by a plurality of frame members, each of the plurality of rows having a distal end, a proximal end, and a mid-portion between the proximal and distal ends, the plurality of rows of closed cells including a distal row of closed cells at the distal end of the frame portion and a proximal row of closed cells at the proximal end of the frame portion, and further wherein the distal constraining loop circumscribes the distal row of closed cells at the mid-portion of the distal row of closed cells and the proximal constraining loop circumscribes the proximal row of closed cells at the mid-portion of the proximal row of closed cells.

According to another example ("Example 18") further to any of Examples 13 to 17, the frame portion of the prosthetic valve has a distal end and a proximal end and further wherein the distal constraining loop constrains the distal end of the frame portion in a tapered configuration such that the frame portion defines a reduced transverse outer profile at the distal end of the frame portion and the proximal constraining loop constrains the proximal end of the frame portion in a tapered configuration such that the proximal end of the frame portion defines a reduced transverse outer profile at the proximal end of the frame portion.

According to another example ("Example 19") further to any of Examples 1 to 18, the proximal guide has a second constraint passage and the distal constraint passes through the second constraint passage of the proximal guide.

According to another example ("Example 20") further to any of Examples 1 to 19, the proximal guide has an angled portion.

According to another example ("Example 21"), a method of delivery an implantable medical device to a desired treatment site in a body of a patient with the transcatheter delivery system of any of preceding Examples 1 to 20, includes positioning the implantable medical device at a desired location in a patient using the transcatheter delivery system, the implantable medical device being mounted on the support portion of the transcatheter delivery system and maintained in a collapsed, delivery configuration by the proximal constraining loop and the distal constraining loop of the prosthetic delivery system; releasing the proximal constraining loop by decreasing tension on the proximal constraint such that a proximal portion of the implantable medical device self-expands; and releasing the distal constraining loop by decreasing tension on the distal constraint such that a distal portion of the implantable medical device self-expands.

According to another example ("Example 22") further to Example 21, the proximal and distal constraining loops are released concurrently.

According to another example ("Example 23") further to Example 21, the proximal and distal constraining loops are released sequentially.

According to another example ("Example 24"), a method of assembling a transcatheter delivery system includes arranging a prosthetic valve on the support portion of the delivery catheter of any one of Examples 1 to 20 such that a central longitudinal axis of the prosthetic valve is laterally offset from a central longitudinal axis of the support portion and a leaflet region of the prosthetic valve is located between the proximal guide and the distal guide of the support portion; compacting the prosthetic valve into a radially compressed delivery configuration such that the leaflet region is received in securing the proximal constraint and the distal constraint around the prosthetic valve and to the delivery catheter with the stake member; and constraining the prosthetic valve in the radially compressed delivery configuration with the proximal constraining loop defined by the proximal constraint and the distal constraining loop defined by the distal constraint.

According to one example ("Example 25"), a transcatheter delivery system includes a delivery catheter. The delivery catheter includes a body portion, a support portion extending from the body portion, the support portion configured to support an implantable device, a stake member, at least one constraint configured to be tensioned to the stake member to maintain the implantable device in a compacted delivery configuration, de-tensioned from the stake member to permit the implantable device to be transitioned to an expanded deployed configuration, and to be released from the stake member to release the implantable device from the delivery catheter, and an actuation portion configured to tension the at least one constraint, de-tension the at least one constraint, and release the at least one constraint from the stake member. The actuation portion includes a housing assembly coupled to the body portion, a rack assembly received in the housing assembly and including a slide rail secured to the stake member and slidably receiving a slider secured to the at least one constraint, a drive assembly slidably received over the slide rail and engageable with the slider to longitudinally translate the slider within the slide rail, and an actuation assembly including a rotatable deployment knob and configured to longitudinally translate the drive assembly along the slide rail.

According to another example ("Example 26") further to Example 25, the actuation portion further comprises a release assembly configured to longitudinally translate the slide rail to longitudinally translate the stake member.

According to another example ("Example 27") further to Examples 25 or 26, the at least one constraint includes a catch releasably secured to the stake member.

According to another example ("Example 28") further to any one of Examples 25 to 27, the drive assembly includes a clutch.

According to another example ("Example 29") further to Example 28, the clutch is a ratchet clutch.

According to another example ("Example 30") further to any one of Examples 25 to 29, the body portion, the rack assembly, and the drive assembly are releasably secured to the housing assembly by one or more clips, such that the rack assembly and the drive assembly are configured to be released from the drive assembly and the housing and slid longitudinally out from a distal end of the housing assembly.

According to another example ("Example 31") further to any one of Examples 25 to 30, the transcatheter delivery system comprises an implantable device maintained in a compacted delivery configuration on the support portion by the at least one constraint.

According to another example ("Example 32") further to Example 31, the implantable device is a prosthetic valve.

According to another example ("Example 33") further to any one of Examples 25 to 32, the delivery catheter includes at least two constraints, each constraint configured to be tensioned to the stake member to maintain the implantable device in the compacted delivery configuration, de-tensioned from the stake member to permit the implantable device to be transitioned to the expanded deployed configuration, and to be released from the stake member to release the implantable device from the delivery catheter.

According to another example ("Example 34") further to any one of Examples 25 to 33, the actuation assembly further includes a nut portion and a gear portion defining a clutch arrangement such that rotation of the gear portion results in rotation of the nut portion up until a torsional limit is reached at which point the gear portion is allowed to slip against the nut portion.

According to another example ("Example 35") further to Example 34, the nut portion is threaded onto the drive assembly.

According to another example ("Example 36") further to any one of Examples 34 or 35, the gear portion includes a plurality of teeth engaged with a plurality of teeth of the deployment knob.

According to another example ("Example 37") further to any one of Examples 1 to 25, the delivery catheter further includes a stake member and an actuation portion configured to tension at least one of the distal and the proximal constraints, de-tension the at least one of the distal and the proximal constraints, and release the at least one of the distal and the proximal constraints from the stake member. The actuation portion includes a housing assembly coupled to the body portion, a rack assembly received in the housing assembly and including a slide rail secured to the stake member and slidably receiving a slider secured to the at least one of the distal and the proximal constraints, a drive assembly slidably received over the slide rail and engageable with the slider to longitudinally translate the slider within the slide rail, and an actuation assembly including a rotatable deployment knob and configured to longitudinally translate the drive assembly along the slide rail.

According to another example ("Example 38"), the features of any one of Examples 25 to 36 are further included with the features of Example 37.

According to another example ("Example 39"), further to any preceding example, the implantable device includes a frame portion having a plurality of circumferentially-oriented eyelets configured to receive one or more constraints.

According to another example ("Example 40"), further to any preceding example, the transcatheter delivery system includes one or more constraints formed with an eye splice to define a catch.

According to another example ("Example 41"), further to any one of Examples 2 to 6, the distal guide includes a filament that extends around the support portion to form a first securing loop that couples the distal guide to the support portion and a first guide loop that defines the constraint passage of the distal guide.

According to another example ("Example 42"), further to any one of Examples 2 to 6 and 41, the proximal guide includes a filament that extends around the support portion to form a first securing loop that couples the proximal guide to the support portion and a first guide loop that defines the constraint passage of the proximal guide.

According to another example ("Example 43"), further to any one of Examples 42, the filament of the proximal guide extends around the support portion to form a second securing loop that couples the proximal guide to the support portion, and further wherein the first guide loop of the proximal guide is located between the first securing loop and the second securing loop of the proximal guide.

According to another example ("Example 44"), further to any one of Examples 42 or 43, wherein the filament of the proximal guide is formed into a second guide loop that defines a passage, the second guide loop being located adjacent to the first guide loop of the proximal guide.

According to another example ("Example 45"), further to Examples 44, the constraint passage of the first guide loop of the proximal guide is angularly offset from the passage of the second guide loop of the proximal guide.

According to another example ("Example 46"), further to any one of Examples 2 to 6 and 41, the proximal guide includes a fiber guide tube that defines the constraint passage of the proximal guide and which includes a receiving portion and a take-off portion, the receiving portion extending along the outer surface of the support portion at a first, transverse angular position relative to a top of the support portion and at a first longitudinal angle relative to the longitudinal axis the support portion, and the take-off portion extending along the outer surface of the support portion at a second transverse angular position relative to the top of the support portion that is different than the first, transverse angular position and at a second longitudinal angle relative to the longitudinal axis of the support portion that is different than the first longitudinal angle.

According to another example ("Example 47"), further to Example 46, the first longitudinal angle is from −15 to 15 degrees.

According to another example, ("Example 48"), further to Examples 46 or 47, the second longitudinal angle is from 75 to 105 degrees.

According to another example, ("Example 49"), further to any one of Examples 46 to 48, the first transverse angular position is from 165 to 195 degrees.

According to another example ("Example 50"), further to any one of Examples 46 to 49, the second transverse angular position is from 120 to 150 degrees.

According to another example ("Example 51"), further to any one of Examples 46 to 50, the fiber guide tube further defines a transition portion between the receiving portion and the take-off portion, the transition portion extending longitudinally and circumferentially to curve along the surface of the support portion.

According to another example ("Example 52"), further to any one of Examples 46 to 51, the take-off portion defines an outwardly flared outlet of the fiber guide tube.

According to another example ("Example 53"), further to any one of Examples 46 to 52, the receiving portion defines an outwardly flared inlet of the fiber guide tube.

According to another example ("Example 54"), further to any one of Examples 46 to 53, the proximal guide further includes a stake guide tube extending along the outer surface of the support portion at a third transverse angular position relative to a top of the support portion and at a third longitudinal angle relative to the longitudinal axis of the support portion.

According to another example ("Example 55"), further to Example 54, the third transverse angular position is from −15 to 15 degrees and the third longitudinal angle is from −15 to 15 degrees.

According to another example ("Example 56"), further to any one of Examples 2 to 6 and 41 to 55, the distal guide includes a fiber guide tube that defines the constraint passage of the distal guide and which includes a receiving portion and a take-off portion, the receiving portion of the distal guide extending along the outer surface of the support portion at a first transverse angular position relative to a top of the support portion and at a first longitudinal angle relative to the longitudinal axis the support portion, and the take-off portion of the distal guide extending along the outer surface of the support portion at a second transverse angular position relative to the top of the support portion that is different than the first transverse angular position and at a second longitudinal angle relative to the longitudinal axis of the support portion that is different than the first longitudinal angle.

According to another example ("Example 57"), further to any preceding example, the transcatheter delivery system includes a delivery catheter and an implantable device, such as a prosthetic valve, where the implantable device includes at least one row of: a plurality of constraint guides included with a cover of the implantable device, a plurality of constraint retainers attached to a frame member of the implantable device, or a plurality of apertures in a cover of the implantable device for receiving a constraint of the transcatheter delivery system to secure the implantable device in a compacted delivery state.

According to another example, ("Example 58"), a transcatheter delivery system for a prosthetic valve includes a support portion configured to support a first frame and a second frame situated in series such that the first frame and the second frame are longitudinally offset from one another. The delivery system further includes a plurality of stake members including a first stake member and second stake member. The delivery system further includes a first constraint disposed about the first frame and operable to maintain the first frame in a delivery configuration, wherein the first constraint is releasably engaged with the first stake member. The delivery system further includes a second constraint disposed about the second frame and operable to maintain the second frame in a delivery configuration, wherein the second constraint is releasably engaged with the second stake member, and wherein the first and second stake members are operable to independent release the first and second constraints.

According to another example, ("Example 59") further to Example 58, the delivery system further includes a plurality of guides including a first guide and a second guide, wherein the first constraint extends through the first guide and the second constraint extends through the second guide.

According to another example, ("Example 60") further to Example 59, the first stake member extends through the first guide.

According to another example, ("Example 61") further to any of Examples 58 and 59, the outer frame is supported at least, at least in part, by the first guide, and wherein the inner frame is supported, at least in part, by the second guide.

According to another example, ("Example 62") further to any of the preceding Examples, the first frame and the second frame are longitudinally offset from one another such that a proximal end of the inner frame is situated distal of a distal end of the outer frame.

According to another example, ("Example 63") a method of delivering a prosthetic valve, includes providing a prosthetic valve that includes an outer frame, and an inner frame nestable within the outer frame. The method further includes providing a transcatheter delivery system that includes a first constraint and a second constraint, and a first stake member secured to the first constraint and a second stake member secured to the second constraint, wherein the prosthetic valve is loaded on the delivery system such that the inner frame and the outer frame are longitudinally offset from one another. The method further includes releasing the first constraint from the first stake member such that the outer frame expands from a delivery configuration to a deployed configuration, and after the outer frame has expanded, advancing the delivery system relative to the outer frame such that the inner frame is advanced relative to the outer frame. The method further includes nesting the inner frame within the outer frame, and thereafter, releasing the first constraint from the first locking element such that the inner frame expands from a delivery configuration to a deployed configuration.

According to another example, ("Example 64") further to Example 63, the inner frame and the outer frame are longitudinally offset from one another such that a proximal end of the inner frame is situated distal of a distal end of the outer frame.

According to another example, ("Example 65") further to any of Examples 63 and 64, the first constraint is release from the first stake member by proximally withdrawing the first stake member.

According to another example ("Example 66"), further to any preceding example the transcatheter delivery system includes a shaft extending through a body portion and support portion of the system, the shaft including an enhanced flexibility portion proximal to the support portion, the enhanced flexibility portion including a distal section having a cut pattern characterized by a first pitch and a proximal section having a cut pattern characterized by a second pitch that is greater than the first pitch.

According to another example, ("Example 67"), further to Example 66, the distal section includes a distal transition portion having cut pattern characterized by a third pitch that is greater than the first pitch.

The foregoing Examples are just that, and should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description explain the principles of the disclosure.

FIG. 5A is a top-down view of a support portion of a delivery catheter, according to some embodiments.

FIG. 5B is a full section view of a delivery catheter taken along a longitudinal axis Xs from the top-down view of FIG. 5A, according to some embodiments.

FIG. 6A is a top-down view of a support portion of a delivery catheter, according to some embodiments.

FIG. 6B is a full section view of a delivery catheter taken along a longitudinal axis Xs from the top-down view of FIG. 6A, according to some embodiments.

FIGS. 7A and 7B show optional features employable for a body portion and a support portion of a delivery catheter, according to some embodiments.

FIG. 14A shows a prosthetic valve in a compacted delivery state, according to some embodiments.

FIG. 14B shows a prosthetic valve partially retracted into a sheath, according to some embodiments.

FIG. 21B shows a sectional view taken along line B-B in FIG. 21A, according to some embodiments.

FIG. 21C shows a sectional view taken along line C-C in FIG. 21A, according to some embodiments.

FIG. 21D shows a sectional view taken along line D-D in FIG. 21A, according to some embodiments.

FIG. 21E shows a sectional view taken along line E-E in FIG. 21A, according to some embodiments.

FIG. 21F shows a sectional view taken along line F-F in FIG. 21A, according to some embodiments.

FIGS. 22A-22D show additional examples of designs for proximal, distal, and intermediate guides, according to some embodiments.

DETAILED DESCRIPTION

Various aspects of the disclosure relate to transcatheter delivery systems that facilitate reduced delivery profiles, promote selective deployment at a desired position, and/or provide reduced crimping/clamping forces on valve leaflet structures, among other additional or alternative features and advantages. Various examples relate to prosthetic valves used for cardiac valve replacement (e.g., for treating a failing or otherwise defective aortic or mitral valve) or other applications associated with native valve or other valve orifices, and related systems, methods, and apparatuses. In some associated treatment methods, the prosthetic valve is utilized to treat valve stenosis (e.g., aortic valve stenosis) and/or valve insufficiency (e.g., aortic valve insufficiency). Although features of transcatheter delivery systems for prosthetic valves are generally shown and described in the present disclosure, similar features and principles of operation are employable with other types of implantable devices, including stents, stent grafts, occluders, and vascular filters, for example, among others.

Unless otherwise indicated, where the terms "distal" and "proximal" are used in the instant disclosure in relation to features of delivery catheters, those terms are generally used with reference to distal being in a direction away from a user (e.g., away from a handle portion) of the delivery catheter and proximal in a direction toward a user (e.g., toward the handle portion).

Unless otherwise indicated, where the terms "distal" and "proximal" are used in the instant disclosure in relation to features of prosthetic valves or other implantable devices, the term "distal" is generally used to refer to an inflow end or a direction that is opposite that of primary flow through the device and proximal is generally used to refer to an outflow end or direction of primary flow through the device.

Figure 1:
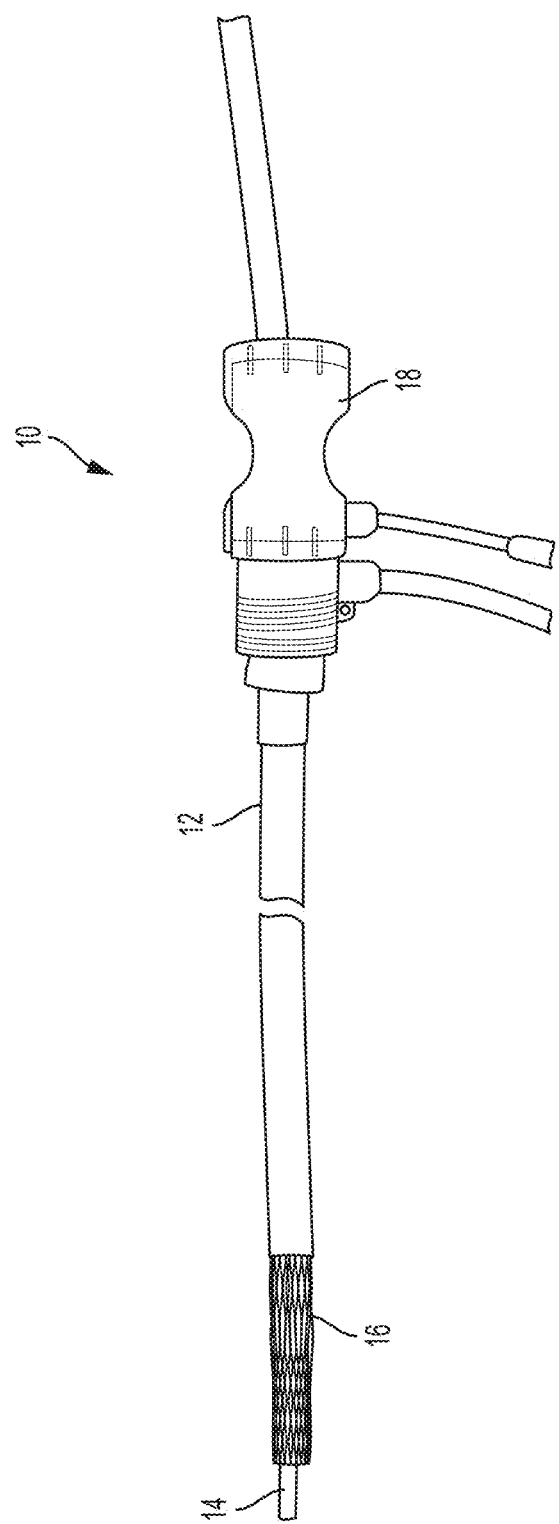
FIG. 1 shows a transcatheter delivery system, according to some embodiments.

FIG. 1 shows a transcatheter delivery system 10, including a sheath 12, a delivery catheter 14, and a prosthetic valve 16 maintained in a collapsed configuration by the delivery catheter 14. As shown, the prosthetic valve 16 is arranged on the delivery catheter 14 in a distally extended position from the sheath 12. Or, in different terms, the prosthetic valve 16 is in an extended position. As previously referenced, the prosthetic valve 16 can be substituted with a variety of self-expanding implantable devices, such as a stent, stent graft, occluder, or vascular filter, for example.

As shown, the sheath 12 is optionally an introducer sheath including a hemostatic valve 18, for example, although any of a variety of additional or alternative features are contemplated.

Figure 2:
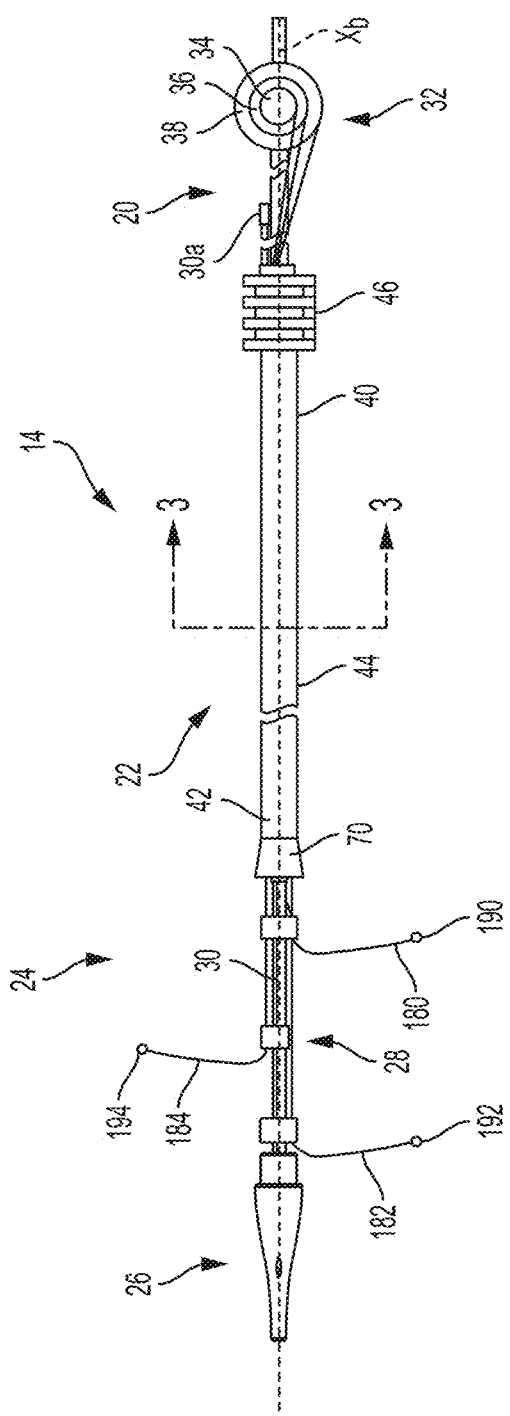
FIG. 2 is a side view of the delivery catheter of a transcatheter delivery system, according to some embodiments.

FIG. 2 is a side view of the delivery catheter 14, according to some embodiments. As shown, the delivery catheter 14 includes an actuation portion 20, a body portion 22, a support portion 24, a tip portion 26, a plurality of constraints 28, and a stake member 30.

In some embodiments, the actuation portion 20 optionally includes a plurality of spindles 32 that are each able to be rotated, including a first spindle 34, a second spindle 36, and a third spindle 38. One or more of the first spindle 34, the second spindle 36, and the third spindle 38 are optionally rotationally coupled to one another and/or are independently rotatable as desired. For reference, the term "coupled" should be read in a broad sense to refer to direct or indirect attachment and to include both fixed and translatable attachment, depending upon context. Various forms of clutches, gears, or other means for controlling relative rotational speed, timing, or other interactions between the spindles 32 are contemplated. Each of the first spindle 34, the second spindle 36 and the third spindle 38 is optionally configured to be used to wind up, or tension, and let out, or de-tension, a constraint received in the body portion 22 of the delivery catheter 14, as is subsequently described. Also, as subsequently described, additional designs for the actuation portion 20 are contemplated.

The body portion 22 defines a central longitudinal axis Xb and has a proximal section 40, a distal section 42, and an intermediate section 44 between the proximal section 40 and the distal section 42, and a connector hub 46. The body portion 22 is of suitable length for a user (not shown) to manipulate the delivery catheter 14 from a location outside the body of a patient into which the prosthetic valve 16 is being implanted. Generally, the body portion 22 is of sufficient flexibility, length, and column strength such that it is suitable for traversing the vasculature or other bodily lumens and conduits within a patient (not shown).

Figure 3:
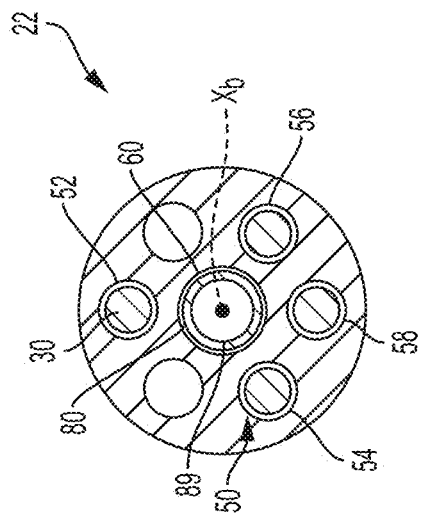
FIG. 3 is a sectional view taken along line 3-3 in FIG. 2 and rotated counterclockwise ninety degrees, according to some embodiments.

FIG. 3 is a sectional view taken along line 3-3 in FIG. 2 and rotated counterclockwise ninety degrees, according to some embodiments. As shown in FIG. 3, the body portion 22 has a plurality of lumens 50 extending within the body portion 22, which can also be described as passages or channels. The plurality of lumens 50 extend the length of the body portion 22 through the proximal section 40, the distal section 42, and the intermediate section 44 (FIG. 2). In some embodiments, the plurality of lumens 50 include a stake member lumen 52, a first constraint lumen 54, a second constraint lumen 56, a third constraint lumen 58, and a central lumen 60, although any number of lumens (e.g., one, six, twelve, etc.), are contemplated. The stake member lumen 52, the first constraint lumen 54, the second constraint lumen 56, and the third constraint lumen 58 are each optionally located at a desired angular position about the central longitudinal axis Xb of the body portion 22.

As shown, the stake member lumen 52 is at a position corresponding to 12 o'clock or 0 degrees, the first constraint lumen 54 is at a position corresponding to 8 o'clock or 120 degrees, the second constraint lumen 56 is at a position corresponding to 4 o'clock or 60 degrees, and the third constraint lumen 58 is at a position corresponding to 6 o'clock, or 90 degrees. In some embodiments, the stake member lumen 52 is positioned on one half of the transverse cross-section of the body portion 22 (e.g., the upper half as shown) and the first constraint lumen 54, the second constraint lumen 56, and the third constraint lumen 58 are positioned on an opposite half of the transverse cross-section of the body portion 22 (e.g., the lower half as shown). Such positioning can assist with balancing the overall design, including reducing unwanted bending and/or enhancing preferential bending/bending flexibility in a desired direction, although a variety of features and considerations may be applicable. Though some examples of angular positions are provided, any number of positions can be employed as desired. As shown, the central lumen 60 may be positioned coaxially with the longitudinal axis Xb of the body portion 22, although, again, any number of positions can be employed as desired.

As shown in FIG. 2, the proximal section 40 is coupled to and supports the actuation portion 20 such that the first spindle 34, the second spindle 36 and the third spindle 38 are rotatable (e.g., transverse to the longitudinal axis Xb of the body portion 22). Though not shown, one or more of the first spindle 34, the second spindle 36, and the third spindle 38 optionally includes a handle or other feature to assist with operation (e.g., rotation) thereof.

The distal section 42 is coupled to the support portion 24 and optionally includes one or more features for assisting with passing the distal section 42 into, out of, and/or through the sheath 12. For example, as shown in FIG. 2, the distal section 42 includes a flare 70, also described as a flange or taper, to provide an increased diametric profile to the distal section 42 adjacent the support portion 24. This increased diametric profile, also described as an outer transverse profile, has a relatively smooth transition to reduce snagging or mechanical friction between the sheath 12 and the distal section 42 when the distal section 42 is slid through, extended from, and/or retracted into the sheath 12 and through the vasculature or other conduits within a patient (not shown).

For reference, transverse outer profile may be calculated at a transverse cross-sectional location of a component by calculating the cross-sectional area defined by the outer surface at that location. For sake of clarity, the cross-sectional area of the transverse outer profile would include the area of any passages, channels, lumens, holes, etc. in the calculation. Alternatively, transverse outer profile may be calculated by taking a maximum diametric dimension defined by a component at the location.

As previously referenced, the intermediate section 44 is of sufficient flexibility, length, and column strength such that it is suitable for traversing the vasculature or other bodily lumens or other conduits within a patient (not shown).

The connector hub 46 is optionally used to secure the body portion 22 to the actuation portion 20 and/or other components and may include a luer connector, seals, and/or other features as desired. In general terms, the plurality of constraints 28 and the stake member 30 optionally pass through the connector hub 46 such that they can be coupled to the actuation portion 20.

Figure 4:
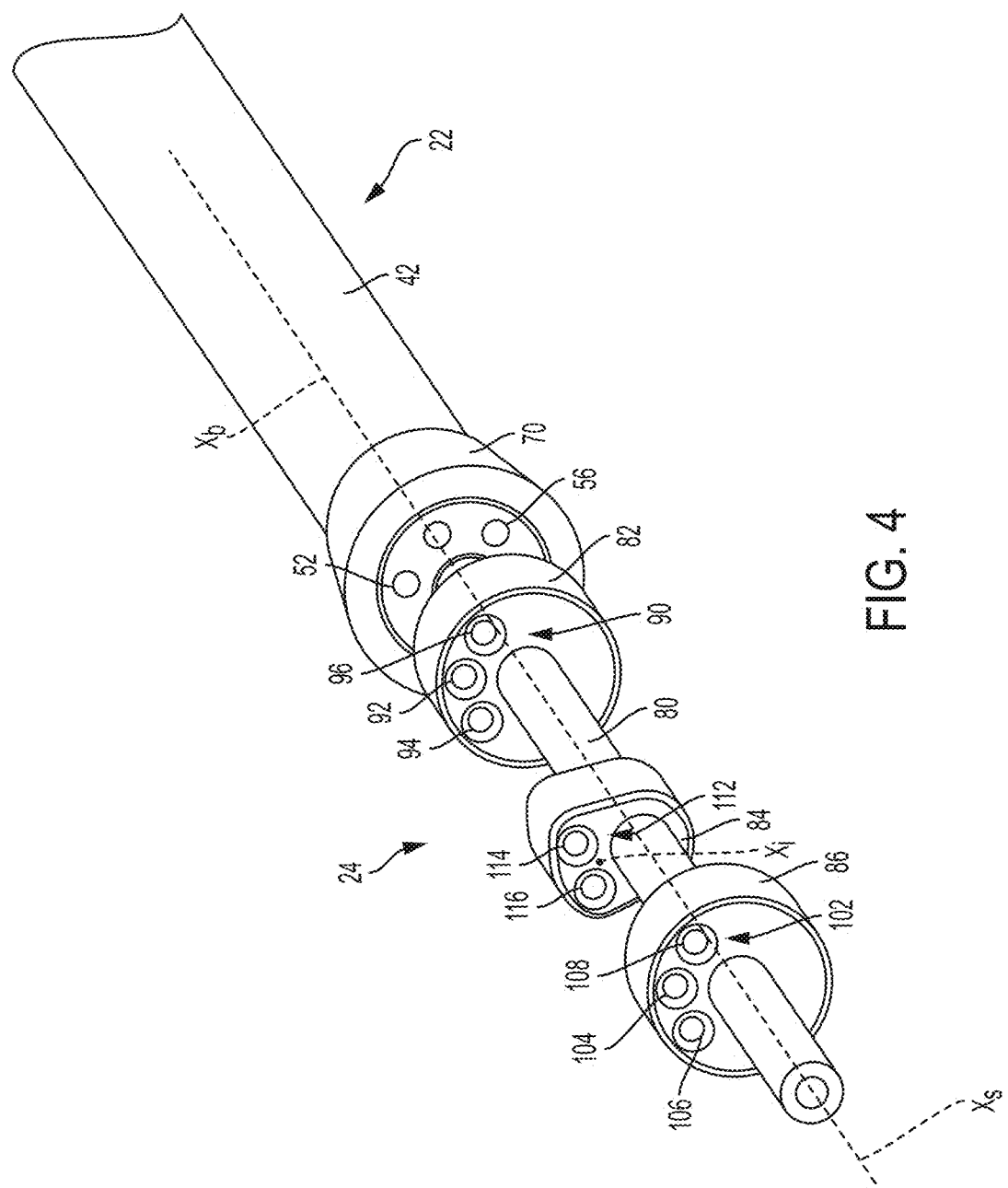
FIG. 4 is an isometric, or perspective, view of a support portion of a delivery catheter, according to some embodiments.

FIG. 4 is an isometric, or perspective, view of the delivery catheter 14 showing the support portion 24 in greater detail, according to some embodiments. The support portion 24 is generally configured to be received in the prosthetic valve 16 (FIG. 1) and to support the prosthetic valve 16 through delivery to, and deployment at a desired treatment location in a body of a patient (not shown). As shown, the support portion 24 extends from the distal section 42 of the body portion 22 and has a central longitudinal axis Xs. The support portion 24 includes a shaft 80, a proximal guide 82, a distal guide 84, and an intermediate guide 86, according to some embodiments. Although three guides 82, 84, 86 are shown, any number of guides (e.g., one, two, four, nine, etc.) are contemplated.

Figure 6C:
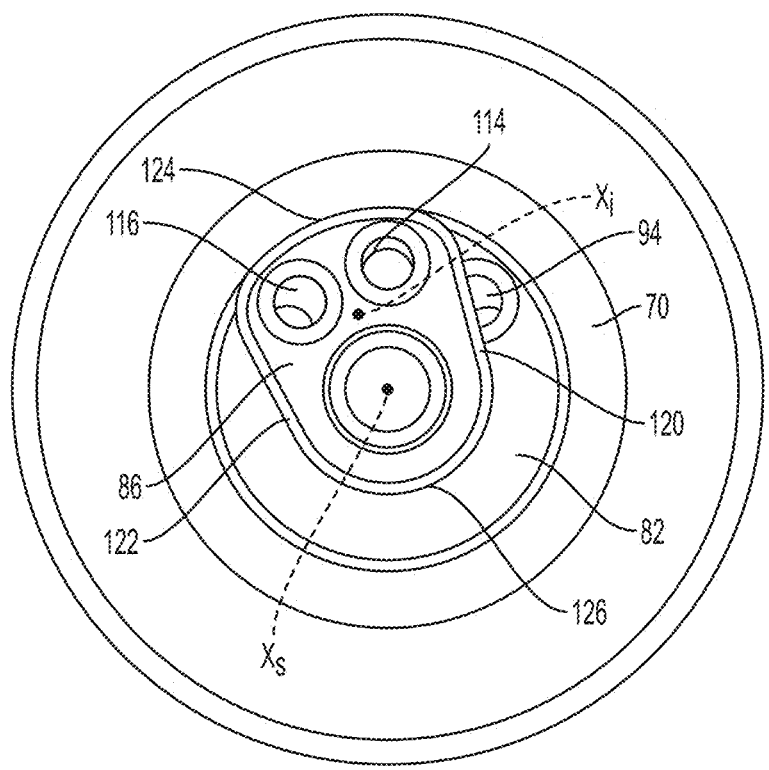
FIG. 6C is a cross-sectional end view taken along line 6C-6C in FIG. 5A, according to some embodiments.

FIG. 5A is a top-down view of the delivery catheter 14 showing the support portion 24 and FIG. 5B is a sectional view of the delivery catheter 14 taken along the longitudinal axis Xs from the top-down view of FIG. 5A. FIG. 6A is a top-down view of the delivery catheter 14 showing the support portion 24 and FIG. 6B is a sectional view of the delivery catheter 14 taken along the longitudinal axis Xs from the top-down view of FIG. 6A. FIG. 6C is a cross-sectional end view taken along line 6C-6C in FIG. 5A for additional reference. The shaft 80 can be flexible, relatively rigid, or combinations thereof. For example, the shaft 80 is optionally relatively more rigid (e.g., being a continuous hypotube) in the support portion 24 and relatively more flexible (e.g., having cuts, reliefs or other features for enhancing flexibility) along the remainder of delivery catheter 14. The shaft 80 is elongate and as shown in FIG. 6B optionally includes a central lumen 89 (e.g., for receiving a guidewire). As shown in FIG. 4 and FIG. 5A, the shaft 80 has a central longitudinal axis (not separately labeled) that is coaxial with the central longitudinal axis Xb of the body portion 22 and/or the central longitudinal axis Xs of the support portion 24. In other examples, however, the shaft 80 may be at a lateral offset (e.g., parallel, but offset from) the central longitudinal axis Xb and/or Xs.

In various embodiments, the shaft 80 is formed as a hollow tube (e.g., hypotube), for example using nitinol, stainless steel, or other metallic or polymeric materials. In various examples, the shaft 80 is configured to receive a guidewire (not shown) for guiding the delivery catheter 14 to a desired treatment location. If desired, however, the shaft 80 may also be formed as a solid member without any internal lumen. The shaft 80 is optionally coupled to the tip portion 26 (e.g., inserted into and press-fit or bonded to the tip portion 26), extends a length of the support portion 24, and may also form part of the body portion 22 (e.g., extending through the central lumen 60 and out of the proximal end 206 of the body portion 22). In different terms, the body portion 22 may also include the shaft 80. The shaft 80 is optionally a single, unitary member, though separate connected components are also contemplated.

As shown in FIGS. 4, 5A, 5B, 6A, and 6B, the proximal guide 82 is cylindrical overall, having a transverse outer profile that is cylindrical, which also corresponds to a transverse outer profile that is circular in transverse cross-section. As the transverse outer profile is cylindrical, the proximal guide 82 generally defines a maximum transverse outer profile along the entire length of the proximal guide 82. However, in other examples, the proximal guide 82 defines a maximum transverse outer profile at one or more transverse cross-sections along the length of the proximal guide 82 and a minimum transverse outer profile at one or more transverse cross-sections along the length of the proximal guide 82. For example, although cylindrical profiles are contemplated, any of a variety of tapers, steps, chamfers and other features is also contemplated.

The proximal guide 82 defines a central longitudinal axis (not separately labeled) that is coaxial with the central longitudinal axis Xs of the support portion 24 and by transitive theory, the central longitudinal axis of the shaft 80, according to some examples.

As shown in FIG. 5B, in some embodiments, the proximal guide 82 includes a central lumen 88 through which the shaft 80 is received, for coupling the proximal guide 82 to the shaft 80. As shown in FIG. 4, the proximal guide 82 also includes a plurality of passages 90, also described as channels or lumens. As shown, the plurality of passages 90 include a stake member passage 92, a first constraint passage 94, and a second constraint passage 96, although greater or fewer (e.g., one, four, ten, etc.) are contemplated. The stake member passage 92, the first constraint passage 94, and the second constraint passage 96 are each optionally located at a desired angular position about the central longitudinal axis Xs of the support portion 24.

As shown, the stake member passage 92 is at an angular position corresponding to 12 o'clock or 0 degrees, the first constraint passage 94 is at an angular position corresponding to 11 o'clock, or −15 degrees, and the second constraint passage 96 is at an angular position corresponding to 1 o'clock or 15 degrees. Though some examples of angular positions are provided, any number of angular positions can be employed as desired.

As seen with reference between FIGS. 4, 5A, 5B, 6A, and 6B, the distal guide 84 is substantially similar to the proximal guide 82. In some examples, the distal guide 84 is also cylindrical overall, having a transverse outer profile that is cylindrical, which also corresponds to a transverse outer profile that is circular in transverse cross-section. As the transverse outer profile is cylindrical, the distal guide 84 generally defines a maximum transverse outer profile along the entire length of the distal guide 84. However, in other examples, the distal guide 84 defines a maximum transverse outer profile at one or more transverse cross-sections along the length of the distal guide 84 and a minimum transverse outer profile at one or more transverse cross-sections along the length of the proximal guide 82. For example, although cylindrical profiles that are circular in transverse cross-section are contemplated, any of a variety of tapers, steps, chamfers and other features are also contemplated.

The distal guide 84 also defines a central longitudinal axis (not separately labeled) that is coaxial with the central longitudinal axis Xs of the support portion 24 and by transitive theory, the central longitudinal axis of the shaft 80 (as well as the proximal guide 82), according to some examples.

In some embodiments, the distal guide 84 includes a central lumen 100 through which the shaft 80 is received, for coupling the distal guide 84 to the shaft 80. As shown in FIG. 4, the distal guide 84 also includes a plurality of passages 102, also described as channels or lumens. As shown, the plurality of passages 102 include a stake member passage 104, a first constraint passage 106, and a second constraint passage 108, although greater or fewer (e.g., one, four, ten, etc.) are contemplated. The stake member passage 104, first constraint passage 106, and second constraint passage 108 are each optionally located at a desired angular position about the central longitudinal axis Xs of the support portion 24.

As shown, the stake member passage 104 is at an angular position corresponding to 12 o'clock or 0 degrees, the first constraint passage 106 is at an angular position corresponding to 11 o'clock, or −15 degrees, and the second constraint passage 108 is at an angular position corresponding to 1 o'clock or 15 degrees. Though some examples of angular positions are provided, any number of angular positions can be employed as desired.

In some embodiments, each of the plurality of passages 90 of the proximal guide 82 is aligned with each of the plurality of passages 102 of the distal guide 84. In other words, the stake member passage 104 is angularly aligned with the stake member passage 92, the first constraint passage 106 with the first constraint passage 94, etc. In other embodiments, one or more of the plurality of passages 90 and the plurality of passages 102 are angularly misaligned, or out of alignment with one another. Moreover, it should be readily appreciated that the proximal guide 82 need not have the same number of passages as the distal guide 84.

In some embodiments, the angular position of the first constraint passage 94 of the proximal guide 82 is angularly offset from the angular position of the second constraint passage 108 of the distal guide 84 by 10 to 350 degrees, although any variety of offsets are contemplated (e.g., 15 to 45 degrees). In some examples, the angular position of the first constraint passage 116 of the intermediate guide 86 is angularly offset from the angular position of the second constraint passage 108 of the distal guide 84 by 10 to 350 degrees, although a variety of offsets are contemplated (e.g., 15 to 45 degrees).

As shown in FIGS. 4, 5A, 5B, 6A, and 6B, the intermediate guide 86 has a reduced transverse outer profile, or a smaller transverse cross-section (e.g., as calculated comparing cross-sectional areas of the shapes of the respective transverse outer profiles) than the proximal guide 82, as well as the distal guide 84.

For example, both the proximal guide 82 and distal guide 84 define a transverse outer profile that is circular in cross-section, and thus defines a cross-sectional area that can be calculated by the simple formula of the number pi multiplied by diameter of the proximal guide 82 and/or distal guide 84 squared. For sake of clarity, the cross-sectional area of the transverse outer profile would include the area of any passages, channels, lumens, holes, etc. in the calculation. And, for more complex transverse outer profiles, such as that of the intermediate guide 86, other mathematical methodology may be employed to calculate the cross-sectional area of the transverse outer profile, according to well-understood principles. Alternatively, the transverse outer profile can be calculated by taking the maximum diametric dimension (in this case, the outer diameter) of the proximal guide 82 and/or distal guide 84.

In some examples, the cross-sectional area of the transverse outer profile of the intermediate guide 86 is at least 20%, at least 30%, at least 40%, at least 50%, at least 60%, or at least 80% less than that of the proximal guide 82 (e.g., the maximum and/or minimum transverse outer profile) and/or distal guide 84 (e.g., the maximum and/or minimum transverse outer profile), or any range of percentages between any of the foregoing percentages. As subsequently described, minimizing the cross-sectional area of the intermediate guide 86 may help reduce crimping forces on the prosthetic valve 16 and/or the overall delivery profile of the prosthetic valve 16 as received on the delivery catheter 14, for example.

The intermediate guide 86 has a more irregular shape, having a transverse outer profile that is generally a rounded and truncated pie-shape. Described in different terms, the intermediate guide 86 has a transverse outer profile that is trapezoidal in shape overall with convex, or outward-facing curves at the top and the bottom and four rounded corners.

As shown, the intermediate guide 86 has a constant transverse cross-section along the length of the intermediate guide 86. As such, the transverse outer profile of the intermediate guide 86 is substantially consistent along the length of the intermediate guide 86. And, in turn, the intermediate guide 86 generally defines a maximum transverse outer profile along the entire length of the intermediate guide 86. However, in other examples, the intermediate guide 86 defines a maximum transverse outer profile at one or more transverse cross-section positions along the length of the intermediate guide 86. For example, any of a variety of tapers, steps, chamfers and other features is also contemplated.

As shown in FIGS. 4 and 6C, the intermediate guide 86 also defines a longitudinal axis Xi that passes longitudinally through a center of mass, or a center of inertia, of the maximum transverse outer profile of the intermediate guide 86. The longitudinal axis Xi is parallel to, and laterally offset from the central longitudinal axes of the proximal guide 82 and the distal guide 84 (which correspond to the central longitudinal axis Xs), according to some examples.

As shown in FIGS. 5B and 6B, in some embodiments, the intermediate guide 86 includes a central lumen 110 through which the shaft 80 is received, for coupling the intermediate guide 86 to the shaft 80. As shown in FIG. 4, the intermediate guide 86 also includes a plurality of passages 112, also described as channels or lumens. As shown, the plurality of passages 112 include a stake member passage 114 and a first constraint passage 116, although greater or fewer (e.g., one, three, ten, etc.) are contemplated. The stake member passage 114 and first constraint passage 116 are each located at a desired angular position about the central longitudinal axis Xs of the support portion 24.

As shown, the stake member passage 114 is at an angular position corresponding to 12 o'clock or 0 degrees and the first constraint passage 116 is at an angular position corresponding to 11 o'clock or −15 degrees. Though some examples of angular positions are provided, any number of angular positions can be employed as desired.

As shown in FIG. 6C, in some examples, the intermediate guide 86 has a first side 120, a second side 122, a top 124, and a bottom 126. As shown, the bottom 126 is positioned closer to the central lumen 110 than the top 124, such that the central lumen 110 is offset between the top 124 and the bottom 126. This offset helps provide a packing, or receiving space for receiving selected portions of the prosthetic valve 16 that may benefit from additional space as part of compression of the prosthetic valve 16 onto the support portion 24 (e.g., a leaflet region 262 as further described).

In some embodiments, each of the proximal guide 82, the distal guide 84, and the intermediate guide 86 is coupled to the shaft 80 (e.g., by welding, crimping, press-fit, adhesives, or other techniques). In some examples the shaft 80 maintains and supports each of the proximal guide 82, distal guide 84, and intermediate guide 86 in a longitudinally-spaced relationship to one another and longitudinally-spaced from the body portion 22 and the tip portion 26. As shown in FIGS. 5A and 5B, in this manner, the support portion 24 defines a plurality of reduced profile sections 150, including a proximal reduced profile section 152 extending between the proximal guide 82 and the distal section 42 of the body portion 22, a first reduced profile section 154 extending between the proximal guide 82 and the intermediate guide 86, a second reduced profile section 156 extending between the intermediate guide 86 and the distal guide 84, and a distal reduced profile section 158 extending between the distal guide 84 and the tip portion 26. As shown, both the first reduced profile section 154 and the second reduced profile section 156 are at locations that are intermediate or between the proximal guide 82 and the distal guide 84.

As shown, each of the reduced profile sections 150 is defined by a transverse outer profile of the shaft 80, which has the same maximum and minimum transverse outer profile through the length of the support portion 24, and which is circular in transverse cross-section and defines a transverse, cross-sectional area determined by pi multiplied by the diameter of the shaft 80 squared, although a variety of shapes are also contemplated for the shaft 80. The reduced profile sections 150 can help provide a variety of advantages, including increased flexibility in the support portion 24, additional space for receiving the prosthetic valve 16 during compression onto the delivery catheter 14, or others. For example, in some embodiments, each of the reduced profile sections 150 has increased bending flexibility relative to adjacent sections of the support portion 24, such as the bending flexibilities of the support portion 24 at the proximal guide 82, distal guide 84, and/or intermediate guide 86, although such feature may be absent in other examples.

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the proximal guide 82 (e.g., the maximum and/or minimum transverse outer profile), such that the proximal reduced diameter section has a transverse outer profile that is at least 20%, at least 30%, at least 40%, at least 50%, at least 60%, or at least 80% less than that of the proximal guide 82 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the distal guide 84 (e.g., the maximum and/or minimum transverse outer profile), such that the proximal reduced diameter section has a transverse outer profile that is at least 20%, at least 30%, at least 40%, at least 50%, at least 60%, or at least 80% less than that of the distal guide 84 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the intermediate guide 86 (e.g., the maximum and/or minimum transverse outer profile), such that the proximal reduced diameter section has a transverse outer profile that is at least 20%, at least 30%, at least 40%, at least 50%, at least 60%, or at least 80% less than that of the intermediate guide 86 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the distal section 42 of the body portion 22 (e.g., the maximum and/or minimum transverse outer profile), such that the proximal reduced diameter section has a transverse outer profile that is at least 20%, at least 30%, at least 40%, at least 50%, at least 60%, or at least 80% less than that of the distal section 42 of the body portion 22 (or any range of percentages between any of the foregoing percentages).

As shown in FIGS. 6A and 6B, the tip portion 26 has a stake member passage 160 and a central lumen 162, and includes a proximal support section 164, and a distal nose section 166. The proximal support section 164 has a reduced transverse outer profile relative to the distal nose section 166 to define a recess for receiving a portion of the prosthetic valve 16. In general terms, the proximal support section 164 is optionally configured to receive an end portion of the prosthetic valve 16 with the adjacent, increased profile of the distal nose section 166 assisting to protect the end of the prosthetic valve 16 (FIG. 1) from snagging or otherwise impeding delivery through the sheath 12 (FIG. 1) and within the patient's body (not shown).

The proximal support section 164 defines a transverse outer profile that is circular in cross-section, and thus defines a cross-sectional area that can be calculated by the simple formula of the number pi multiplied by diameter of the proximal support section 164 squared. Although a circular transverse cross-section is shown and described, any shape for the transverse outer profile of the proximal support section 164 is contemplated. For sake of clarity, the cross-sectional area of the transverse outer profile would include the area of any channels, lumens, holes, etc. in the calculation (i.e., it would be treated as a solid cross-section for determining the transverse outer profile cross-sectional area). As previously referenced, the transverse outer profile can alternative be calculated by taking the maximum diametric dimension.

As shown, the proximal support section 164 has a constant transverse cross-section along the length of the proximal support section 164. As such, the transverse outer profile of the proximal support section 164 is substantially consistent along the length of the proximal support section 164. And, in turn, the proximal support section 164 generally defines a maximum transverse outer profile along the entire length of the proximal support section 164. However, in other examples, the proximal support section 164 defines a maximum transverse outer profile at one or more transverse cross-sectional positions along the length of the proximal support section 164. For example, any of a variety of tapers, steps, chamfers and other features are contemplated which would result in a varying transverse outer profile.

The proximal support section 164 also defines a central longitudinal axis (not separately labeled) that is coaxial with the central longitudinal axis Xs of the support portion 24, according to some examples. As shown in FIGS. 5B and 6B, the shaft 80 is received in the central lumen 162 for coupling the proximal support section 164 to the shaft 80, and thus the support portion 24. As seen best in FIGS. 4, 5A, and 6B, the stake member passage 160 is located at a desired angular position about the central longitudinal axis of the tip portion 26.

As shown, the stake member passage 160 is at an angular position corresponding to 12 o'clock or 0 degrees. Though an example of an angular position is provided, any number of angular positions can be employed as desired. The angular position of the stake member passage 160 optionally corresponds to the angular position of the stake member lumen 52 of the body portion 22, the stake member passage 92 of the proximal guide 82, the stake member passage 104 of the distal guide 84, according to some examples.

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the proximal support section 164 of the tip portion 26 (e.g., the maximum and/or minimum transverse outer profile), such that the proximal reduced diameter section has a transverse outer profile that is at least 20%, at least 30%, at least 40%, at least 50%, at least 60%, or at least 80% less than that of the proximal support section 164 of the tip portion 26 (or any range of percentages between any of the foregoing percentages).

Various additions and/or alterations are contemplated for the delivery catheter 14. For example, FIGS. 7A and 7B show some optional features employable for the body portion 22 and the support portion 24. As shown, the body portion 22 has a step 176 in the distal section 42 for proximally supporting the prosthetic valve 16. Also, the delivery catheter 14 optionally includes a cover 178 (e.g., a thin layer of material, such as ePTFE or a thin heat shrunk tube of PET) over the support portion 24, extending over the proximal guide 82, the distal guide 84, and the intermediate guide 86. As shown, the cover 178 also optionally extends over the proximal support section 164 of the tip portion 26 and the step 176. The cover 178 includes apertures or other openings (not shown) from which the plurality of constraints 28 (FIG. 2) are able to pass. Additionally, as shown in FIGS. 7A and 7B, the proximal guide 82 and the intermediate guide 86 are each tapered proximally improve the ability to withdraw the delivery catheter 14 back through the deployed prosthetic valve 16 and/or into and through the sheath 12.

As shown in FIG. 2, the plurality of constraints 28 comprise a proximal constraint 180, a distal constraint 182, and an intermediate constraint 184. In some embodiments, each of the plurality of constraints 28 is formed as a fiber, strand, wire, combinations thereof or the like, and may be braided, wound, extruded, or otherwise formed of metallic or polymeric materials. In general terms, each of the plurality of constraints 28 may be described as a filament that is elongate and flexible. For reference, the term "filament" is inclusive of both monofilament and multifilament constructs. In some examples, each of the constraints 28 may be formed from braided strands of material, such as UHMWPE or ePTFE. Although three are shown, any number of constraints 28 (e.g., one, two, four, nine, etc.) are contemplated. In some embodiments, the proximal constraint 180 includes a catch 190 in the form of a terminal, closed loop or eyelet, for example. The catch 190 is optionally formed using braiding methods (e.g., by twisting the braid into itself or through a continuous braiding method that forks a single strand into two separates strands and then rebraids them into a single strand to form an eyelet). The distal constraint 182 similarly includes a catch 192 as does the intermediate constraint 184, which includes a catch 194. FIGS. 24A-24C and 24 provide various examples for forming one or more of the plurality of constraints 28.

FIGS. 2, 3, and 6B show the stake member 30, which can also be described as a lock wire, from various views. In some embodiments, the stake member 30 is formed as a wire, strand, fiber or the like, and may be braided, wound, extruded, or otherwise formed of metallic or polymeric materials. In some examples, the stake member 30 is a wire formed of stainless steel, nitinol, or other material. As seen in FIG. 6B, the stake member 30 extends from a proximal end 30a into the proximal section 40 of the body portion 22 into the stake member lumen 52, through the body portion 22, out of the distal section 42 of the body portion 22 from the stake member lumen 52 (FIG. 3), through the stake member passage 92 (FIG. 6B) of the proximal guide 82, through the stake member passage 104 (FIG. 6B) of the distal guide 84, through the stake member passage 114 (FIG. 6B) of the intermediate guide 86, and into the stake member passage 160 (FIG. 6B) of the tip portion 26. The stake member 30 is slidably received in the stake member lumen 52 and respective passages so that the stake member 30 is retractable from the proximal guide 82, the distal guide 84, and the intermediate guide 86, as subsequently described.

Figure 8:
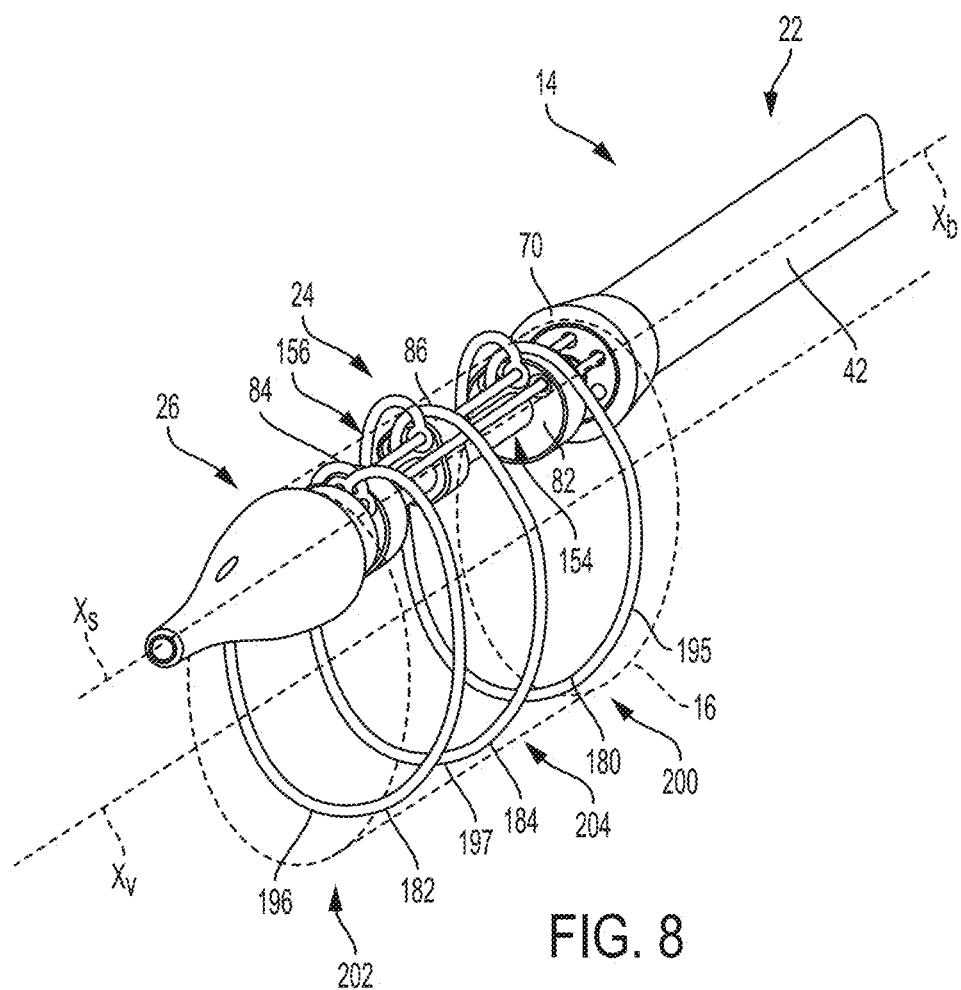
FIG. 8 shows the prosthetic valve in a cylindrical form as received over a support portion of a delivery catheter, according to some embodiments.

FIG. 8 shows the prosthetic valve 16 in a generalized, cylindrical form for ease of visualization as received over the support portion 24 of the delivery catheter 14, with the proximal constraint 180, the distal constraint 182, and the intermediate constraint 184 looped around the prosthetic valve 16, each in a releasable, looped configuration. Assembly of the delivery catheter 14 includes assembly of the prosthetic valve 16 onto the delivery catheter 14 and assembly of the proximal constraint 180, the distal constraint 182, and the intermediate constraint 184 into the respective proximal guide 82, distal guide 84, and intermediate guide 86 and circumferentially around the prosthetic valve 16. As indicated, the prosthetic valve 16 is received over the delivery catheter 14, with the delivery catheter 14 received within the prosthetic valve 16 in a laterally offset position.

Figure 9:
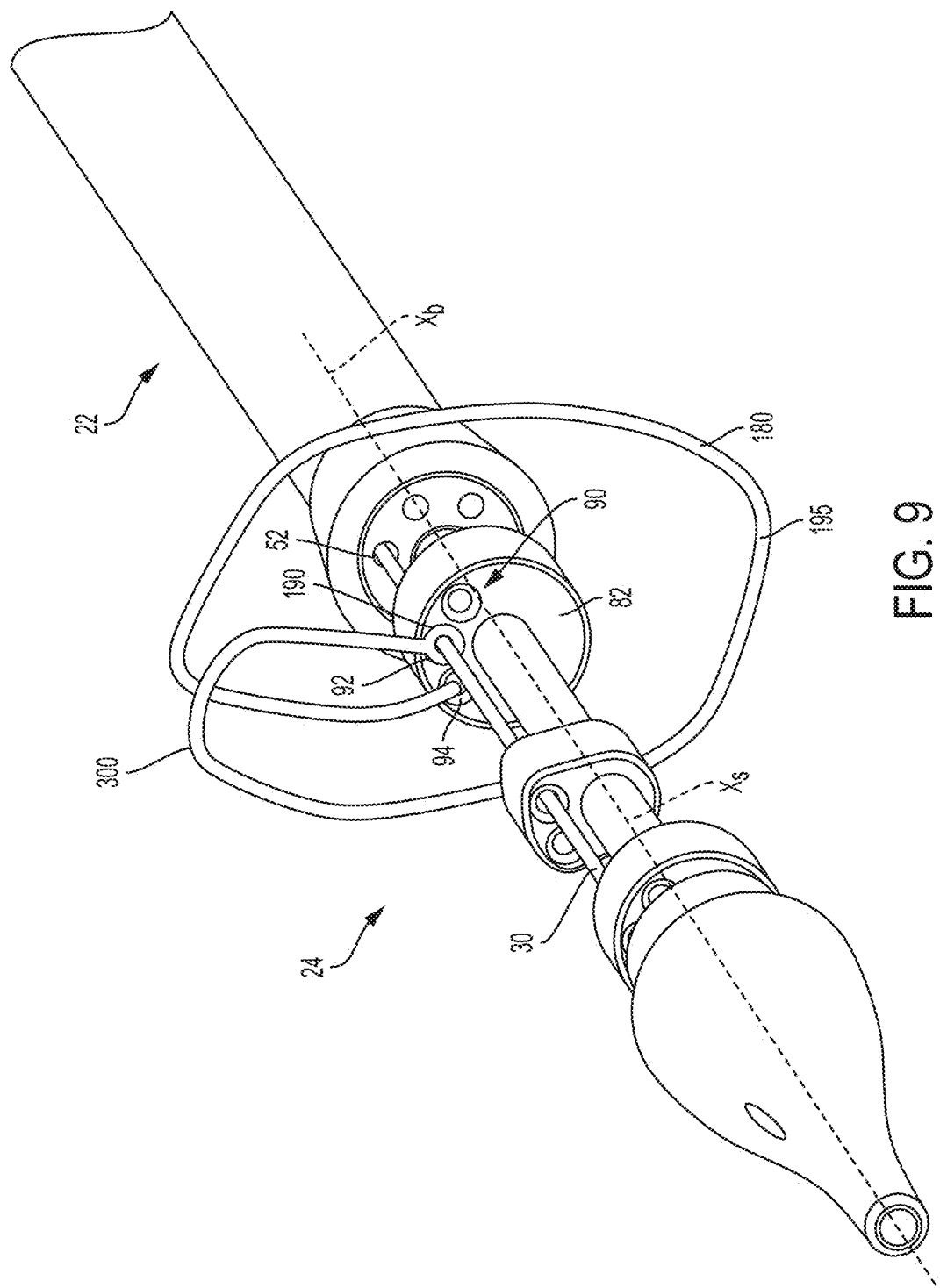
FIG. 9 is an isolated view showing a proximal constraint assembled with a proximal guide and a stake member, according to some embodiments.

FIG. 9 is an isolated view showing the proximal constraint 180 assembled with the proximal guide 82 and the stake member 30. The prosthetic valve 16 and other portions are removed to facilitate understanding how the proximal constraint 180 is secured in a looped configuration, to define a proximal constraining loop 195, according to some embodiments. In some embodiments, the proximal constraint 180 is received by the first spindle 34 (FIG. 2) such that it is windable onto the first spindle 34 and passes into the first constraint lumen 54 of the body portion 22 (FIG. 3). The proximal constraint 180 then passes out of the first constraint lumen 54 (FIG. 3) into one of the plurality of passages 90 (FIG. 4) of the proximal guide 82 (e.g., the first constraint passage 94 as shown), extends through the one of the plurality of passages 90 (e.g., the first constraint passage 94), and distally out of the one of the plurality of passages 90 (e.g., the first constraint passage 94 as shown) and then radially away from the central longitudinal axis Xs of the support portion 24.

The proximal constraint 180 then loops about the support portion 24, crosses over itself, and is secured to the stake member 30 with the stake member 30 received through the catch 190. Proximally tensioning the proximal constraint 180, for example with the first spindle 34 of the actuation portion 20 (FIG. 2), causes the proximal constraining loop 195 to constrict, reducing the diameter of the proximal constraining loop 195 and thus results in a collapsing or constraining force within the proximal constraining loop 195. In turn, release of the tension permits the proximal constraining loop 195 to expand.

Figure 10:
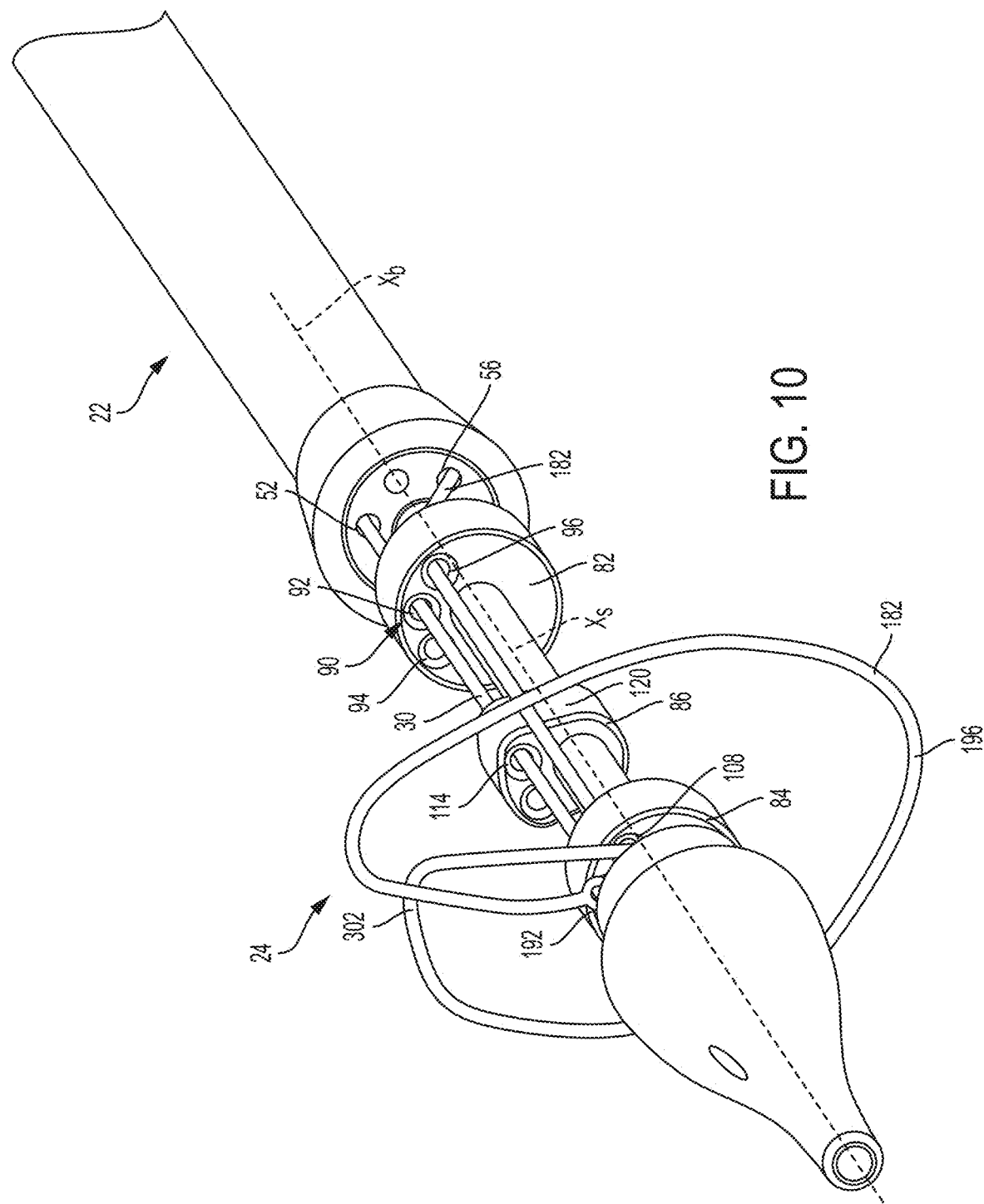
FIG. 10 is an isolated view showing a distal constraint assembled with a distal guide and a stake member, according to some embodiments.

Similarly, FIG. 10 is an isolated view showing the distal constraint 182 assembled with the distal guide 84 and the stake member 30 (again, with the prosthetic valve 16 and other portions removed to facilitate understanding), according to some embodiments. In some embodiments, the distal constraint 182 is received by the second spindle 36 (FIG. 2) such that it is windable onto the second spindle 36 and passes into the second constraint lumen 56 of the body portion 22 (FIG. 3). The distal constraint 182 then passes out of the second constraint lumen 56 (FIG. 3) into one of the plurality of passages 90 of the proximal guide 82 (e.g., the second constraint passage 96 as shown), extends through the one of the plurality of passages 90 (e.g., the second constraint passage 96 as shown), and distally out of the one of the plurality of passages 90 (e.g., the second constraint passage 96 as shown).

The distal constraint 182 then extends past the intermediate guide 86, on one side of the intermediate guide 86 (e.g., the first side 120 as shown) on its way to the distal guide 84.

The distal constraint 182 then enters one of the plurality of passages 102 (FIG. 4) of the distal guide 84 (e.g., the second constraint passage 108 as shown), and distally out of the one of the plurality of passages 102 (e.g., second constraint passage 108). The distal constraint 182 then extends radially away from the central longitudinal axis Xs of the support portion 24, loops about the support portion 24, crosses over itself, and is secured to the stake member 30 with the stake member 30 received through the catch 192 of the distal constraint 182 to define a distal constraining loop 196. Proximally tensioning the distal constraint 182, for example with the second spindle 36 of the actuation portion 20 (FIG. 2), causes the distal constraining loop 196 to constrict, and thus results in a collapsing or constraining force within the distal constraining loop 196 reducing a diameter of the distal constraining loop 196. In turn, release of the tension permits the distal constraining loop 196 to expand.

Figure 11:
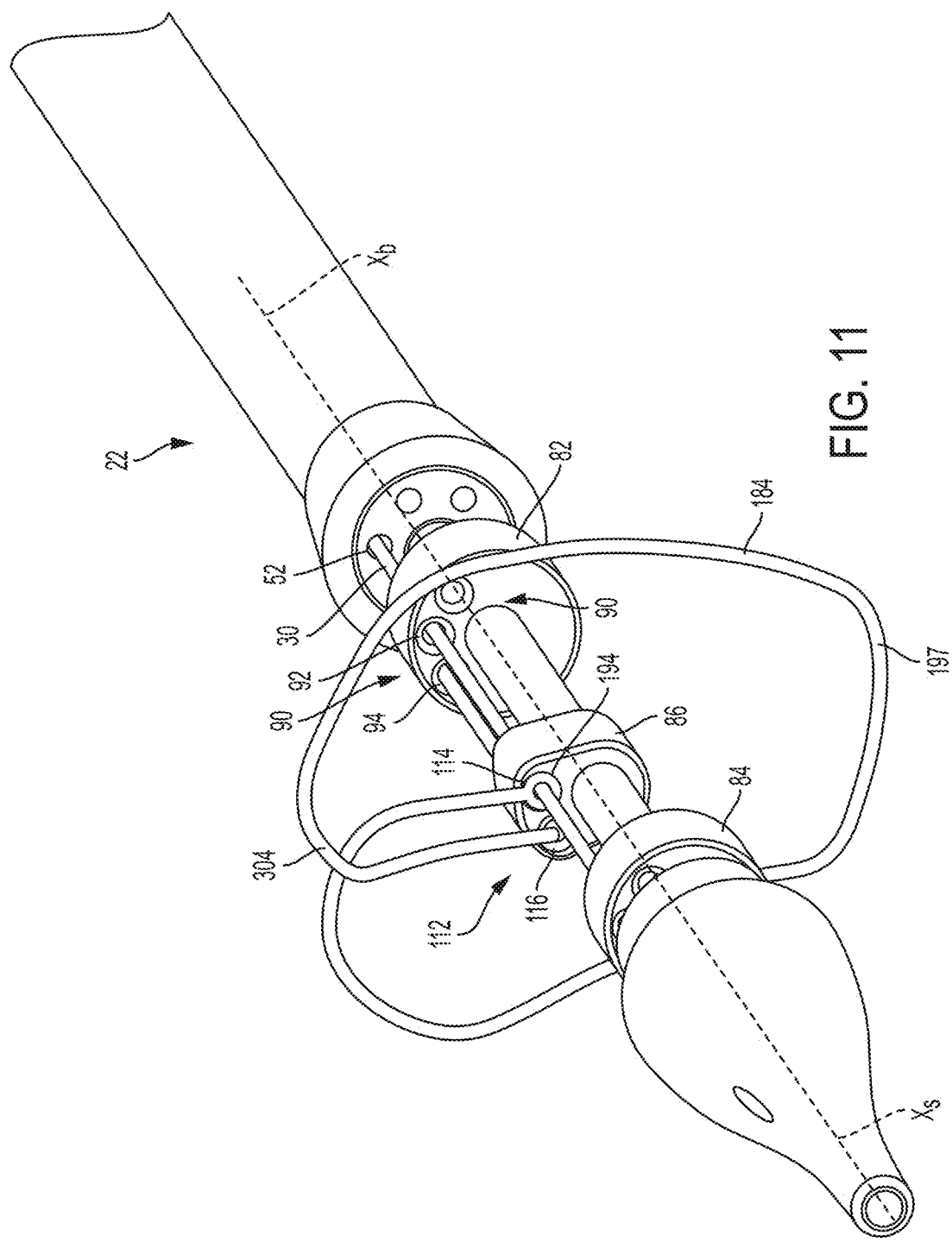
FIG. 11 is an isolated view showing an intermediate constraint assembled with an intermediate guide and a stake member, according to some embodiments.

FIG. 11 is a similar, isolated view showing the intermediate constraint 184 assembled with the intermediate guide 86 and the stake member 30 (again, with the prosthetic valve 16 removed to facilitate understanding), according to some embodiments. In some embodiments, the intermediate constraint 184 is received by the third spindle 38 (FIG. 2) such that it is windable onto the third spindle 38 and passes into the third constraint lumen 58 (FIG. 3) of the body portion 22. The intermediate constraint 184 then passes out of the third constraint lumen 58 into one of the plurality of passages 90 of the proximal guide 82 (e.g., the second constraint passage 96 as shown), extends through the one of the plurality of passages 90 (e.g., the second constraint passage 96 as shown), and distally out of the one of the plurality of passages 90 (e.g., the second constraint passage 96 as shown).

The intermediate constraint 184 then extends into and enters one of the plurality of passages 112 (e.g., the first constraint passage 116 as shown), and distally out of the one of the plurality of passages 112 (e.g., the first constraint passage 116 as shown). The intermediate constraint 184 then extends radially away from the central longitudinal axis Xs of the support portion 24, then loops about the support portion 24, crosses over itself, and is secured to the stake member 30 with the stake member 30 received through the catch 194 of the intermediate constraint 184 to define an intermediate constraining loop 197. Proximally tensioning the intermediate constraint 184, for example with the third spindle 38 of the actuation portion 20 (FIG. 2), causes the intermediate constraining loop 197 to constrict, and thus results in a collapsing or constraining force within the intermediate constraining loop 197 reducing a diameter of the intermediate constraining loop 197. In turn, release of the tension permits the distal constraining loop 196 to expand.

Figure 12:
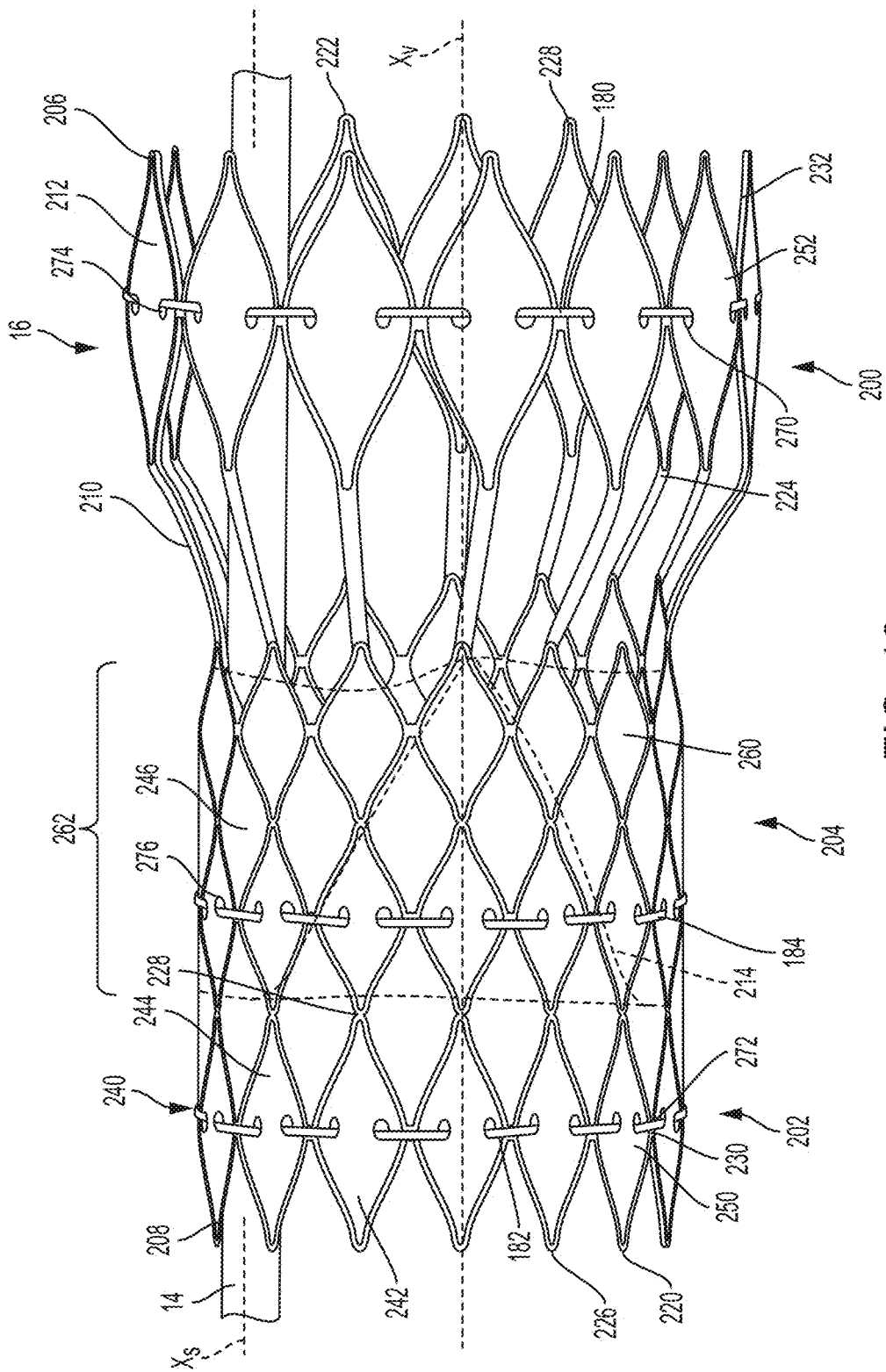
FIG. 12 shows a prosthetic valve received on a delivery catheter, with the prosthetic valve in deployed or expanded state, according to some embodiments.
Figure 13A:
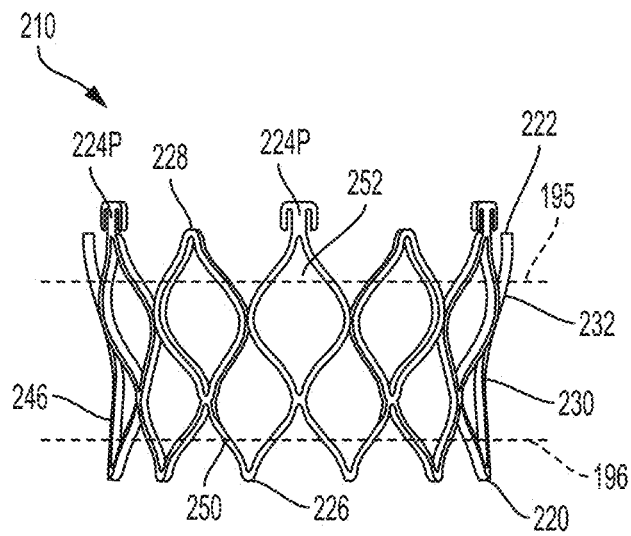
FIGS. 13A to 13D show additional designs for a frame portion that may be used for a prosthetic valve, according to various embodiments.
Figure 13B:
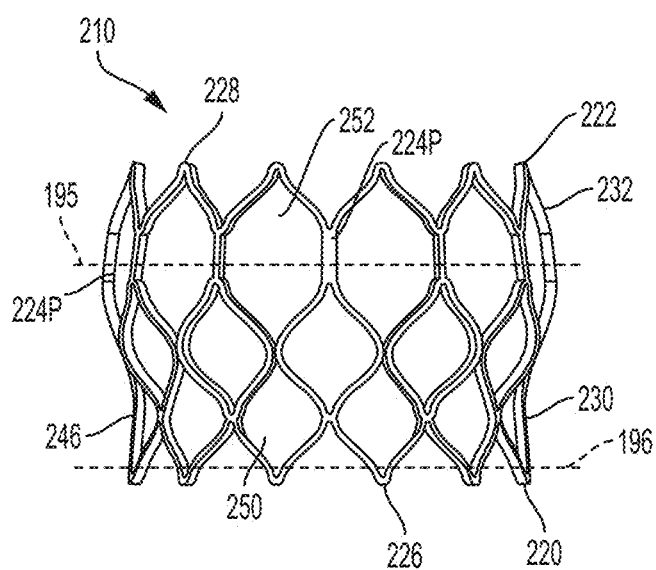
Figure 13C:
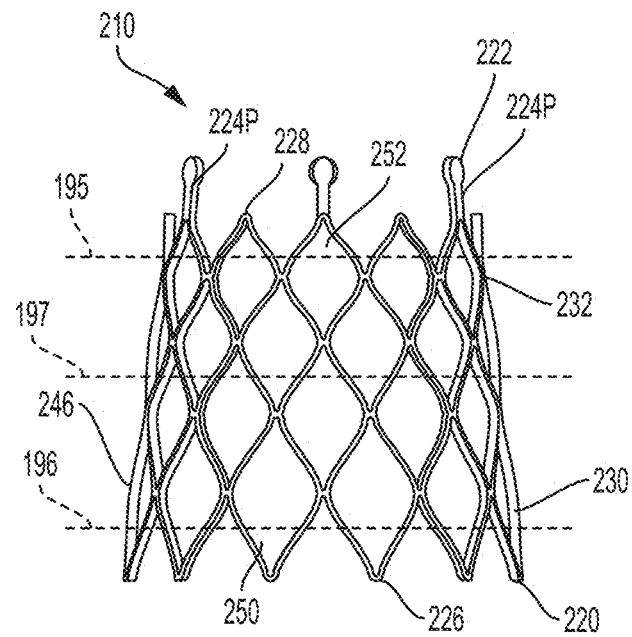
Figure 13D:
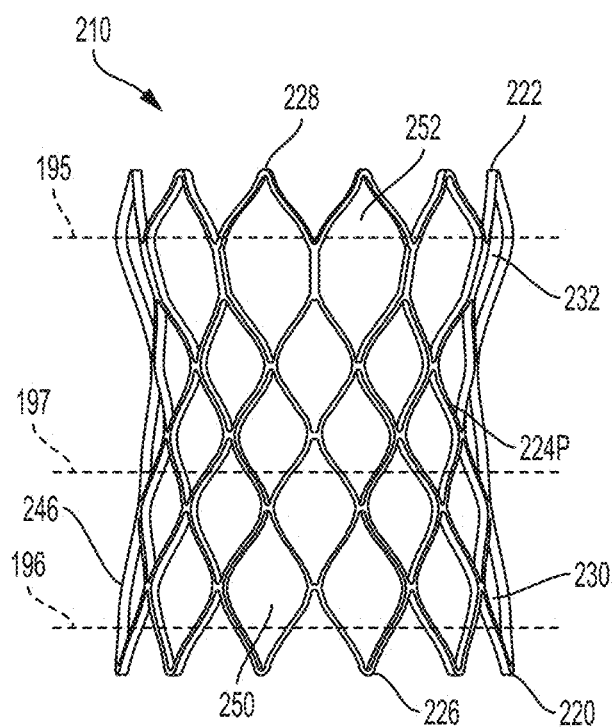

FIG. 12 shows the prosthetic valve 16 received on the delivery catheter 14, with the prosthetic valve in deployed, or expanded state, according to some embodiments. In some examples, the prosthetic valve 16 is a prosthetic heart valve, such as a prosthetic valve for aortic valve or mitral valve replacement/repair. As shown, the prosthetic valve 16 has a central longitudinal axis Xv, a proximal portion 200, also described as an end portion, a distal portion 202, also described as an end portion, and an intermediate portion 204, also described as a mid-portion, and extends between a proximal end 206 and a distal end 208, according to some embodiments. The prosthetic valve 16 includes a frame portion 210 that is self-expanding (e.g., formed of a shape memory alloy, such as nitinol) and a cover 212, and a leaflet construct 214 (hidden, but shown in broken lines) operatively coupled to the frame portion 210 (e.g., directly attached or indirectly attached to the frame portion 210 via the cover 212).

As shown, the frame portion 210 has a distal end 220 and a proximal end 222 and includes a plurality of rows of frame members 224 defining an undulating, alternating pattern of distal-facing apices 226 and proximal-facing apices 228. In some embodiments, the plurality of rows of frame members 224 include a distal row 230 at the distal end 220 of the frame portion 210 and a proximal row 232 at the proximal end 222 of the frame portion 210. The frame portion 210 also includes a plurality of rows of closed cells 240 defined by the plurality of frame members 224, each of the plurality of rows of closed cells 240 having a distal end 242, a proximal end 244, and a mid-portion 246 between the proximal end 244 and the distal end 242. In some examples, the plurality of rows of closed cells 240 includes a distal row of closed cells 250 at the distal end 220 of the frame portion 210 and a proximal row of closed cells 252 at the proximal end 222 of the frame portion 210. FIGS. 13A to 13D show additional designs for the frame portion 210 that may be used for the prosthetic valve 16, according to various embodiments. As shown, each of the designs includes a plurality of commissure attachment regions 224P (such as commissure posts) configured for supporting commissure regions of a leaflet construct.

In some embodiments, the leaflet construct 214 includes a plurality of leaflets 260 (hidden, but labeled with a broken line) that coapt with one another to form a one-way valve. The location or position of the leaflet construct 214 along the length of the prosthetic valve 16 is referenced as a leaflet region 262 or leaflet portion. Various leaflet materials and constructions are contemplated, including the examples that are subsequently described.

In some embodiments, the cover 212 has one or more rows of apertures 270 for receiving one or more of the proximal constraint 180, the distal constraint 182, and the intermediate constraint 184. For example, the rows of apertures 270 optionally include a distal row of apertures 272 (e.g., defined in the cover 212 along the mid-portion 246 of the distal row of closed cells 250), a proximal row of apertures 274 (e.g., defined in the cover 212 along the mid-portion 246 of the proximal row of closed cells 252), and an intermediate row of apertures 276 (defined in the cover 178 along the mid-portion 246 of another one of the plurality of rows of closed cells 240).

FIG. 12 shows a location of the proximal constraint 180, the distal constraint 182, and the intermediate constraint 184 in relation to the prosthetic valve 16, according to some embodiments. As shown, the distal constraint 182, and thus the distal constraining loop 196 (FIG. 10), circumscribes the distal row of closed cells 250 at the mid-portion 246 of the distal row of closed cells 250 and the proximal constraining loop 195 (FIG. 9) circumscribes the proximal row of closed cells 252 at the mid-portion 246 of the proximal row of closed cells 252. As shown, the distal constraining loop 196 circumscribes the distal row of closed cells 250 at a position proximal to the distal-facing apices 226 of the distal row of closed cells 250 and the proximal constraining loop 195 circumscribes the proximal row of closed cells 252 at a position distal to the proximal-facing apices 228 of the proximal row of closed cells 252. In some examples, the intermediate constraining loop 197 (FIG. 11) circumscribes the prosthetic valve 16 at a location between the proximal constraining loop 195 and the distal constraining loop 196 and which also corresponds to the leaflet region 262.

As shown in FIG. 12, in some examples, the distal constraining loop 196 (FIG. 10) is woven through the distal row of apertures 272 such that the distal constraint 182 extends outside over the frame members 224. In some embodiments, the proximal constraint 180 and the intermediate constraint 184 are similarly woven through the proximal row of apertures 274 and intermediate row of apertures 276, respectively, such that the proximal constraining loop 195 (FIG. 9) and the intermediate constraining loop 197 (FIG. 11) extend over the frame members 224. In other examples, the proximal constraint 180, the distal constraint 182, and/or the intermediate constraint 184 are woven through the frame portion 210 using an alternative weaving pattern (e.g., in an over-and-under pattern relative to the frame portion 210 through the rows of closed cells 240).

In some embodiments, the proximal constraint 180 exits the proximal guide 82 passes out of the prosthetic valve 16, encircles the prosthetic valve 16, and defines a crossing-point 300 (indicated generally on FIG. 9 without the prosthetic valve 16 for visualization purposes) where the proximal constraint 180 passes over itself in a cinch arrangement prior to passing back through the prosthetic valve 16 and to the stake member 30. Similarly, in some embodiments, the distal constraint 182 exits the distal guide 84 passes out of the prosthetic valve 16, encircles the prosthetic valve 16, and defines a crossing-point 302 (indicated generally on FIG. 10 without the prosthetic valve 16 for visualization purposes) where the distal constraint 182 passes over itself in a cinch arrangement prior to passing back through the prosthetic valve 16 and to the stake member 30. Again, in some embodiments, the intermediate constraint 184 exits the intermediate guide 86 passes out of the prosthetic valve 16, encircles the prosthetic valve 16, and defines a crossing-point 304 (indicated generally on FIG. 11 without the prosthetic valve 16 for visualization purposes) where the intermediate constraint 184 passes over itself in a cinch arrangement prior to passing back through the prosthetic valve 16 and to the stake member 30.

FIGS. 13A-13D show additional locations for the proximal constraining loop 195, the distal constraining loop 196, and the intermediate constraining loop 197 in accordance with other embodiments of the frame portion 210. As shown the proximal constraining loop 195, the distal constraining loop 196, and the intermediate constraining loop 197 need not each extend over the m id-portion 246 of each of the plurality of rows of closed cells 240. For example, the distal constraining loop 196 may simply circumscribe the distal row of closed cells 250 at a position proximal to the distal-facing apices 226 of the distal row of closed cells 250. Additionally or alternatively, the proximal constraining loop 195 circumscribes the proximal row of closed cells 252 at a position distal to the proximal-facing apices 228 of the proximal row of closed cells 252.

As shown in FIG. 8, the central longitudinal axis Xv of the prosthetic valve 16 is optionally laterally offset from the central longitudinal axis Xs of the support portion 24. In some examples, the prosthetic valve 16 is received over the support portion 24 with the support portion 24 positioned adjacent a commissure post (not shown) of the prosthetic valve 16 and/or at an intersection of two leaflets (not shown) of the prosthetic valve 16. As shown in FIGS. 8 and 12, the prosthetic valve 16 is received over the support portion 24 with the proximal portion 200 over the proximal guide 82, the distal portion 202 over the distal guide 84, and the intermediate portion 204 over the intermediate guide 86. In some embodiments, the leaflet region 262 (FIG. 12) is positioned on the support portion 24 between the proximal guide 82 and the distal guide 84. For example, in some embodiments, the leaflet region 262 does not extend longitudinally beyond the proximal guide 82 and the distal guide 84. As previously referenced, the first reduced profile section 154 and the second reduced profile section 156 are at locations that are intermediate or between the proximal guide 82 and the distal guide 84 and provide additional area for the leaflet construct 214 (FIG. 12) both prior to and during compression of the prosthetic valve 16 onto the support portion 24. Moreover, the relatively reduced profile of the intermediate guide 86 can help provide space for the leaflet construct 214.

FIG. 14A shows the prosthetic valve 16 in a compacted, delivery state with each of the proximal constraining loop 195, the distal constraining loop 196, and the intermediate constraining loop 197 restraining the prosthetic valve 16 in the delivery state. As shown, the proximal constraining loop 195 is positioned along the proximal portion 200 of the prosthetic valve 16 at a location on the frame portion 210 (FIG. 12) that causes the proximal portion 200 to take on a tapered, compressed transverse outer profile, or tapered configuration, that assists with withdrawing and/or extending the prosthetic valve 16 into and/or from the sheath 12 as understood with reference to FIG. 14B. Thus, according to some embodiments, the proximal end 206 of the prosthetic valve 16 defines a reduced transverse outer profile as compared to adjacent portions of the prosthetic valve 16.

Similarly, the distal constraining loop 196 is positioned along the distal portion 202 of the prosthetic valve 16 at a location on the frame portion 210 that causes the proximal portion 200 to take on a tapered, compressed transverse outer profile, or tapered configuration, that assists with extending and/or withdrawing the prosthetic valve 16 from and/or into the sheath 12 as shown in FIG. 14B. By placing the proximal constraining loop 195 and the distal constraining loop 196 at the positions previously described, the proximal constraining loop 195 causes the proximal row of closed cells 252 (FIG. 12) to hinge, or angulate more inward and the distal row of closed cells 250 (FIG. 12) to hinge or angulate more inward. And thus, according to some embodiments, the distal end 208 of the prosthetic valve 16 defines a reduced transverse outer profile as compared to adjacent portions of the prosthetic valve 16 (FIG. 12).

FIGS. 15 to 18B show various features of another support portion 524 that can be utilized with the delivery catheter 14 of the transcatheter delivery system 10, where the support portion 524 utilizes additional or alternative guide configurations to those described for the support portion 24. As previously referenced, any number of guides (e.g., one, two, four, nine, etc.) may be implemented as desired. The various features and components of the support portion 524 may be used interchangeably with any of the components of the support portion 24 previously described (and vice versa).

Figure 15:
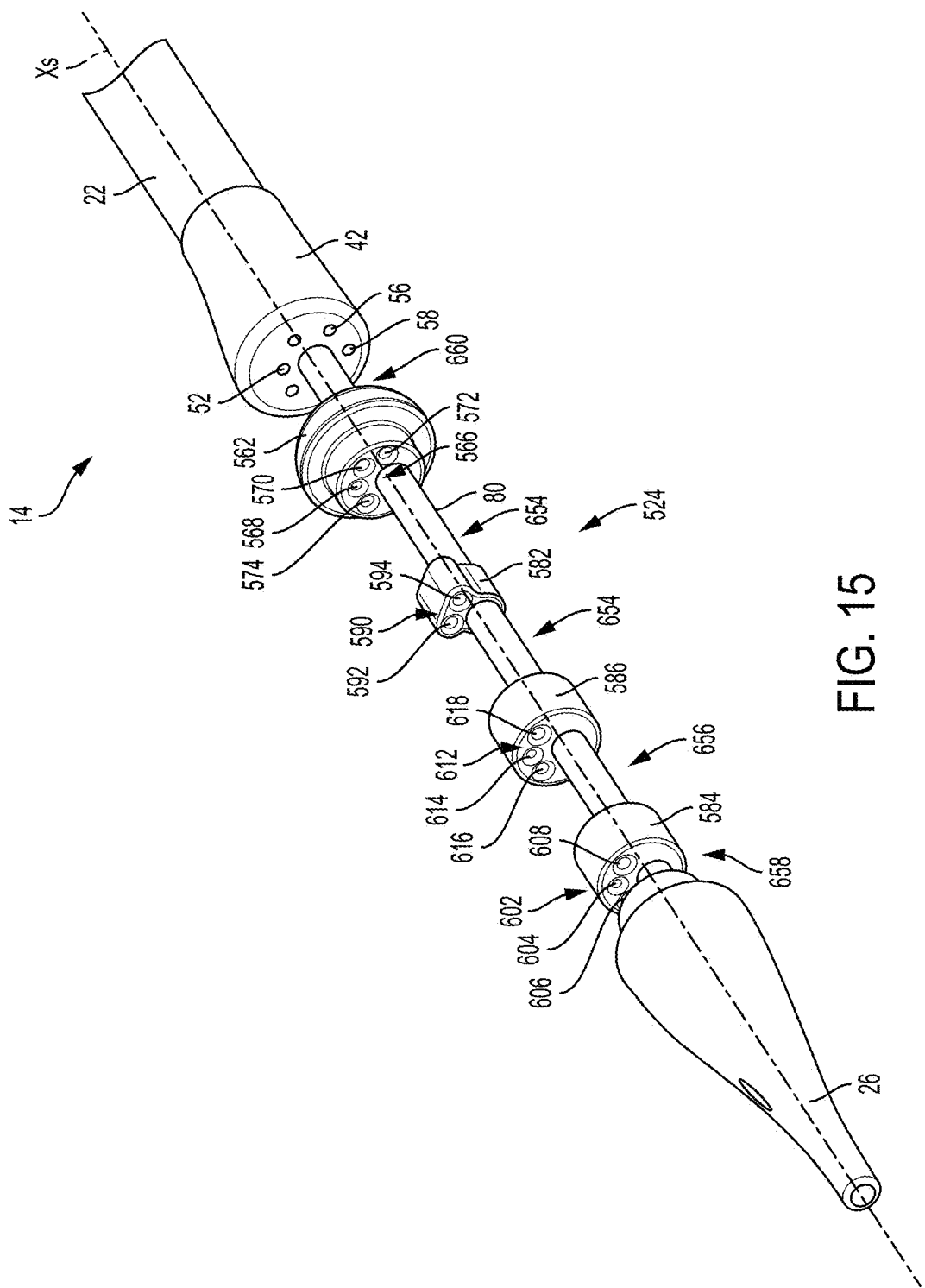
FIGS. 15 to 18B show additional transcatheter delivery system configurations, including additional guide configurations, according to some embodiments.

FIG. 15 is an isometric, or perspective, view of a portion of the delivery catheter 14 showing the support portion 524 in greater detail, according to some embodiments. Like the support portion 24, the support portion 524 is generally configured to be received in the prosthetic valve 16 (FIG. 1) and to support the prosthetic valve 16 through delivery to, and deployment at a desired treatment location in a body of a patient (not shown). As shown, the support portion 524 extends from the distal section 42 of the body portion 22 and has a central longitudinal axis Xs. The support portion 524 includes a portion of the shaft 80, a support guide 562, a proximal guide 582, a distal guide 584, and an intermediate guide 586, according to some embodiments.

In some embodiments, each of the support guide 562, the proximal guide 582, the distal guide 584, and the intermediate guide 586 is coupled to the shaft 80 (e.g., by welding, crimping, press-fit, adhesives, or other techniques) to maintain and support each of the respective guides in a longitudinally-spaced relationship to one another and longitudinally-spaced from the body portion 22 and the tip portion 26.

Figure 17:
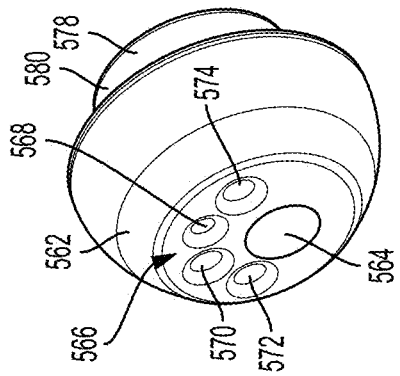
Figure 16:
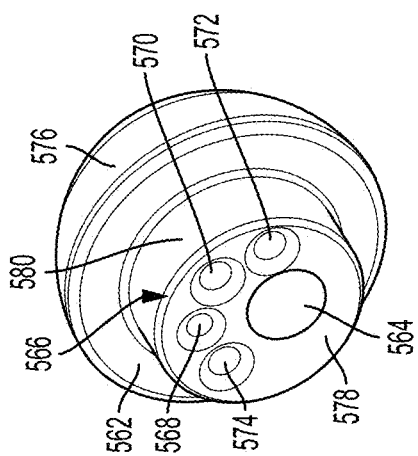

FIG. 16 is a distal-oriented isometric view and FIG. 17 is a proximal-oriented isometric view of the support guide 562. As shown in FIGS. 16 and 17, the support guide 562 includes a central lumen 564 configured to receive the shaft 80 for coupling the support guide 562 to the shaft 80. As shown, the support guide 562 also includes a plurality of passages 566, also described as channels or lumens. As shown, the plurality of passages 566 include a stake member passage 568, a first constraint passage 570, a second constraint passage 572, and a third constraint passage 574, although greater or fewer (e.g., one, four, ten, etc.) are contemplated. The plurality of passages 566 are each optionally located at a desired angular position about the central longitudinal axis Xs of the support portion 524.

As shown in FIGS. 16 and 17, the support guide 562 has a rounded, or hemispherical, or dome-shaped proximal end 576 and a stepped distal end 578, also described as a recess 578, that defines a support surface 580 (e.g., like step 176 shown in FIG. 7B) for receiving an end of the prosthetic valve 16. In general terms, the support surface 580 of the distal end 578 is optionally configured to receive an end portion of the prosthetic valve 16 with the adjacent, increased profile of the distal end 578 assisting to protect the end of the prosthetic valve 16.

In some embodiments, the plurality of passages 566 are generally positioned on opposite radial sides from the first constraint lumen 54, the second constraint lumen 56, and the third constraint lumen 58 of the body portion 22 (e.g., which are positioned on the lower half of the body 22 as shown). Such positioning can assist with balancing the overall design, including reducing unwanted bending and/or enhancing preferential bending/bending flexibility in a desired direction. For example, the various constraints 28 can optionally be tensioned on a side of the delivery catheter 14 opposite the direction the prosthetic valve 16 is to be expanded during deployment. Though some examples of angular positions are provided, any number of positions can be employed as desired.

Figure 18B:
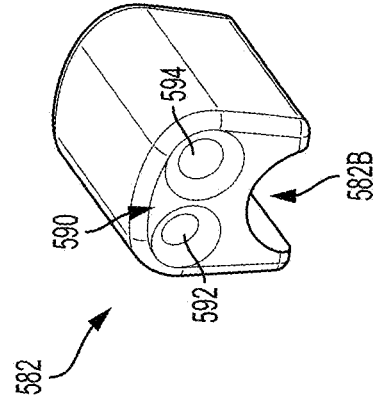
Figure 18A:
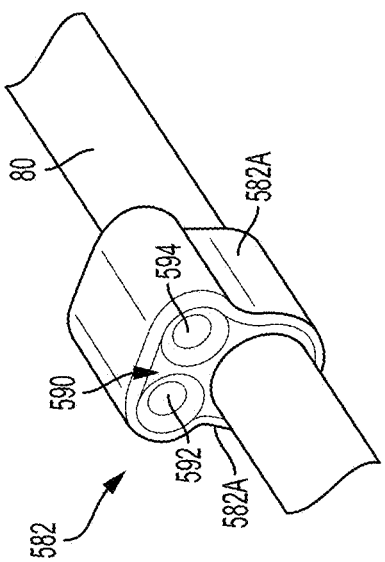

FIG. 18A is an isometric view of the proximal guide 582, according to some embodiments. As shown in FIG. 18A, the proximal guide 582 has substantially the same configuration as the intermediate guide 86 of the support portion 24. In turn, the distal guide 584 and the intermediate guide 586 are shown to each have substantially the same configuration as the distal guide 84 of the support portion 24 (or the proximal guide 82 of the support portion 24).

In some embodiments, the proximal guide 582 includes a central lumen 588 through which the shaft 80 is received, for coupling the proximal guide 582 to the shaft 80. As shown, the proximal guide 582 also includes a plurality of passages 590, also described as channels or lumens. As shown, the plurality of passages 590 include a stake member passage 592 and a first constraint passage 594, although greater or fewer (e.g., one, four, ten, etc.) are contemplated. The stake member passage 592 and the first constraint passage 594 are each optionally located at a desired angular position about the central longitudinal axis Xs of the support portion 524.

Some features of the proximal guide 582 may vary from the design of the intermediate guide 86. For example, as shown in FIGS. 15 and 18A, the proximal guide 582 optionally includes recessed or cut back areas 582A such that additional material is removed relative to the design of the intermediate guide 86, which can help further reduce the outer profile of the proximal guide 582 from that described in association with the intermediate guide 86. Additionally or alternatively, as shown in FIG. 18B, the proximal guide 582 optionally defines an open shaft receiver 582B (rather than a closed lumen as shown in FIG. 18A) for receiving the shaft 80 (FIG. 15). This feature, the open shaft receiver 582B may also achieve reduced material relative to the intermediate guide 86. Where the open shaft receiver 582B is present, rather than the shaft 80 being received in a closed lumen such as the central lumen 588 (e.g., as in FIGS. 15 and 18A), the proximal guide 582 receives the shaft 80 in the open shaft receiver 582B and may be welded along the edges and/or ends to secure the proximal guide 582 to the shaft 80.

As shown in FIG. 15, the distal guide 584 is substantially similar to, or the same design as, the intermediate guide 586, which are both, in turn, similar to the proximal guide 82 and the distal guide 84 of the support portion 524 in design. As shown, the distal guide 584 and the intermediate guide 586 are each cylindrical overall, having a transverse outer profile that is cylindrical, which also corresponds to a transverse outer profile that is circular in transverse cross-section.

In some embodiments, the distal guide 584 includes a plurality of passages 602, also described as channels or lumens. As shown, the plurality of passages 602 include a stake member passage 604, a first constraint passage 606, and a second constraint passage 608, although greater or fewer (e.g., one, four, ten, etc.) are contemplated. The stake member passage 604, the first constraint passage 606, and the second constraint passage 608 are each optionally located at a desired angular position about the central longitudinal axis Xs of the support portion 524.

In some embodiments, the stake member passage 604 is angularly aligned with the stake member passage 592. In some embodiments, one or more of the plurality of passages 590 and the plurality of passages 602 are angularly misaligned, or out of alignment with one another. Moreover, it should be readily appreciated that the proximal guide 582 may have the same number of passages as the distal guide 584 or a different number (as shown).

As shown, the proximal guide 582 has a reduced transverse outer profile, or a smaller transverse cross-section (e.g., as calculated comparing cross-sectional areas of the shapes of the respective transverse outer profiles) than the distal guide 584 and the intermediate guide 586. In some examples, the cross-sectional area of the transverse outer profile of the proximal guide 582 is at least 20%, at least 30%, at least 40%, at least 50%, at least 60%, or at least 80% less than that of the distal guide 584 (e.g., the maximum and/or minimum transverse outer profile) and/or intermediate guide 586 (e.g., the maximum and/or minimum transverse outer profile), or any range of percentages between any of the foregoing percentages. Minimizing the cross-sectional area may help reduce crimping forces on the leaflet area of the prosthetic valve 16 and/or the overall delivery profile of the prosthetic valve 16 as received on the delivery catheter 14, for example.

As shown in FIG. 15, the intermediate guide 586 includes a central lumen 610 through which the shaft 80 is received, for coupling the intermediate guide 586 to the shaft 80. The intermediate guide 586 also includes a plurality of passages 612, also described as channels or lumens. As shown, the plurality of passages 612 include a stake member passage 614, a first constraint passage 616, and a second constraint passage 618, although greater or fewer (e.g., one, three, ten, etc.) are contemplated. The stake member passage 614, the first constraint passage 616, and the second constraint passage 618 are each located at a desired angular position about the central longitudinal axis Xs of the support portion 524.

In some embodiments, the stake member passage 604 is angularly aligned with the stake member passage 614, the first constraint passage 606 is angularly aligned with the first constraint passage 616, and the second constraint passage 608 is angularly aligned with the second constraint passage 618. In other embodiments, one or more of the plurality of passages 602 and the plurality of passages 612 are angularly misaligned, or out of alignment with one another. Moreover, it should be readily appreciated that the intermediate guide 586 may have a different number of passages than the distal guide 584 in other examples.

In some embodiments, the stake member passage 568 is angularly aligned to each of the stake member passages 592, 604, 614, as well as the stake member passage 160 of the tip portion 26 (FIG. 6B). In some embodiments, the first constraint passage 570 is angularly aligned to the first constraint passage 594. In some embodiments, the second constraint passage 572 is angularly aligned to the first constraint passage 616. In some embodiments, the third constraint passage 574 is angularly aligned to the second constraint passages 608, 618.

As shown in FIG. 15, the support portion 524 defines a plurality of reduced profile sections 650, including a proximal reduced profile section 652 extending between the proximal guide 582 and the support guide 562, a first reduced profile section 654 extending between the proximal guide 582 and the intermediate guide 586, a second reduced profile section 656 extending between the intermediate guide 586 and the distal guide 584, and a distal reduced profile section 658 extending between the distal guide 584 and the tip portion 26. Additionally, a proximate reduced profile section 660 is defined between the support guide 562 and the distal section 42 of the body portion 22. As shown, both the first reduced profile section 654 and the second reduced profile section 656 are at locations that are intermediate or between the proximal guide 582 and the distal guide 584.

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the support guide 562 (e.g., the maximum and/or minimum transverse outer profile), such that the proximal reduced diameter section has a transverse outer profile that is at least 20%, at least 30%, at least 40%, at least 50%, at least 60%, or at least 80% less than that of the support guide 562 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the proximal guide 582 (e.g., the maximum and/or minimum transverse outer profile), such that the proximal reduced diameter section has a transverse outer profile that is at least 20%, at least 30%, at least 40%, at least 50%, at least 60%, or at least 80% less than that of the proximal guide 582 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the distal guide 584 (e.g., the maximum and/or minimum transverse outer profile), such that the proximal reduced diameter section has a transverse outer profile that is at least 20%, at least 30%, at least 40%, at least 50%, at least 60%, or at least 80% less than that of the distal guide 584 (or any range of percentages between any of the foregoing percentages).

In some examples, the cross-sectional area of the transverse outer profile of the shaft 80 (e.g., the maximum and/or minimum transverse outer profile) is at least 20%, at least 30%, at least 40%, at least 50%, at least 60%, or at least 80% less than that of the intermediate guide 586 (e.g., the maximum and/or minimum transverse outer profile), such that the proximal reduced diameter section has a transverse outer profile that is at least 20%, at least 30%, at least 40%, at least 50%, at least 60%, or at least 80% less than that of the intermediate guide 586 (or any range of percentages between any of the foregoing percentages).

In some embodiments, the stake member 30 is received in each of the stake member passages 160, 568, 592, 604, 614 to secure the respective constraints 28 in loops for constraining the prosthetic valve 16. Though the constraints 28 are not shown in FIG. 15, reference can be made to FIGS. 8 to 11 with regard to the constraint features referenced below in association with assembly and operation of the support portion 524.

In contrast to the described-configuration with the support portion 24, in some embodiments implementing the support portion 524, the proximal constraint 180 passes through and out of the second constraint lumen 56 (FIG. 3) into and through one of the passages 566 of the support guide 562 (e.g., the first constraint passage 570). The proximal constraint 180 then passes into and through one of the plurality of passages 590 of the proximal guide 582 (e.g., the first constraint passage 594), distally out of the one of the plurality of passages 590 (e.g., the first constraint passage 594) and then radially away from the central longitudinal axis Xs of the support portion 524 to loop about the support portion 524, cross over itself, and be secured to the stake member 30 with the stake member 30 received through the catch 190.

Similar to the support portion 24, proximally tensioning the proximal constraint 180, for example with the first spindle 34 of the actuation portion 20 (FIG. 2), causes the proximal constraining loop 195 to constrict, reducing the diameter of the proximal constraining loop 195 and thus results in a collapsing or constraining force within the proximal constraining loop 195. In turn, release of the tension permits the proximal constraining loop 195 to expand.

In contrast to the described-configuration with the support portion 24, in some embodiments implementing the support portion 524, the distal constraint 182 passes through and out of the third constraint lumen 58 and into and through one of the passages 566 of the support guide 562 (e.g., the second constraint passage 572). The distal constraint 182 then passes outside of the proximal guide 582 and then into and through one of the plurality of passages 612 of the intermediate guide 586 (e.g., the second constraint passage 618) and then into and through one of the plurality of passages 602 of the distal guide 584 (e.g., the second constraint passage 608) to extend radially away from the central longitudinal axis Xs of the support portion 524. The distal constraint 182 loops about the support portion 524, crosses over itself, and is secured to the stake member 30 with the stake member 30 received through the catch 192 of the distal constraint 182 to define a distal constraining loop 196. Proximally tensioning the distal constraint 182, for example with the second spindle 36 of the actuation portion 20 (FIG. 2), causes the distal constraining loop 196 to constrict, and thus results in a collapsing or constraining force within the distal constraining loop 196 reducing a diameter of the distal constraining loop 196. In turn, release of the tension permits the distal constraining loop 196 to expand.

In contrast to the described-configuration with the support portion 24, in some embodiments implementing the support portion 524, the intermediate constraint 184 passes out of the first constraint lumen 54 (FIG. 3) and passes into and through one of the passages 566 of the support guide 562 (e.g., the third constraint passage 574). The intermediate constraint 184 then passes outside of the proximal guide 582 to the intermediate guide 586 and into one of the plurality of passages 612 of the intermediate guide 586 (e.g., the first constraint passage 616 as shown). The intermediate constraint 184 then extends radially away from the central longitudinal axis Xs of the support portion 524, then loops about the support portion 524, crosses over itself, and is secured to the stake member 30 with the stake member 30 received through the catch 194 of the intermediate constraint 184 to define an intermediate constraining loop 197. Proximally tensioning the intermediate constraint 184, for example with the third spindle 38 of the actuation portion 20 (FIG. 2), causes the intermediate constraining loop 197 to constrict, and thus results in a collapsing or constraining force within the intermediate constraining loop 197 reducing a diameter of the intermediate constraining loop 197. In turn, release of the tension permits the distal constraining loop 196 to expand.

Various methods of assembling and operating the transcatheter delivery system 10 are contemplated. Substantially the same methods are optionally used, regardless of whether the support portion 24 or the support portion 524 is employed. Additionally, substantially the same methods can be used for the transcatheter delivery system 510, or additional example transcatheter delivery systems described below (e.g., transcatheter delivery system 1010), to those methods of assembling and operating described below.

In some examples, a method of assembling the transcatheter delivery system 10 includes arranging the prosthetic valve 16 on the support portion 24 of the delivery catheter 14 such that the central longitudinal axis Xv of the prosthetic valve 16 is laterally offset from the central longitudinal axis Xs of the support portion 24 and a leaflet region 262 of the prosthetic valve 16 is located between the proximal guide 82 and the distal guide 84 of the support portion 24 as previously described. The method also includes compacting the prosthetic valve 16 into a radially compressed delivery configuration such that the leaflet region 262 is received over the intermediate guide 86 and in between the proximal guide 82 and the distal guide 84. The proximal constraint 180, the distal constraint 182, and the intermediate constraint 184 are secured around the prosthetic valve 16 and to the delivery catheter 14 with the stake member 30 as previously described. The prosthetic valve 16 is constrained in the radially compressed delivery configuration with the proximal constraining loop 195 defined by the proximal constraint 180, the distal constraining loop 196 defined by the distal constraint 182, and the intermediate constraining loop 197 defined by the intermediate constraint 184. The prosthetic valve 16 in the compacted, delivery state, or configuration, can be received inside the sheath 12 and then extended from the sheath 12 during a medical procedure for delivering the prosthetic valve 16 into a body of a patient. For reference, FIG. 17B shows the prosthetic valve 16 partially retracted into the sheath 12.

Various methods of replacing a natural valve of in a body of a patient with the transcatheter delivery system 10 are contemplated. Some examples include positioning the prosthetic valve 16 at a desired location in a patient using the transcatheter delivery system 10, where the prosthetic valve 16 is mounted on the support portion 24 of the transcatheter delivery system 10 and maintained in a collapsed, delivery configuration by the proximal constraining loop 195, the distal constraining loop 196, and the intermediate constraining loop 197 as previously described. In some examples, the method includes releasing the proximal constraining loop 195 by decreasing tension on the proximal constraint 180 as previously described, such that the proximal portion 200 of the prosthetic valve 16 self-expands, releasing the distal constraining loop 196 by decreasing tension on the distal constraint 182 as previously described, such that the distal portion 202 of the prosthetic valve 16 self-expands, and releasing the intermediate constraining loop 197 by decreasing tension on the intermediate constraint 184 as previously described, such that the intermediate portion 204 of the prosthetic valve 16 self-expands.

In some examples, the proximal constraining loop 195, the distal constraining loop 196, and/or the intermediate constraining loop 197 are released concurrently. In some examples, the proximal constraining loop 195, the distal constraining loop 196, and/or the intermediate constraining loop 197 are released sequentially. Release of the proximal constraining loop 195, the distal constraining loop 196, and the intermediate constraining loop 197 as previously described permits the prosthetic valve 16 to self-expand to an enlarged diameter as shown in FIG. 12. Following expansion, the stake member 30 is able to be slid proximally so that the catch 190 of the proximal constraint 180, the catch 192 of the distal constraint 182, and the catch 194 of the intermediate constraint 184 are released. Then, according to some embodiments, the proximal constraint 180, the distal constraint 182, and the intermediate constraint 184 can be tensioned and pulled from around the prosthetic valve 16 and back to the delivery catheter 14 to release the proximal constraint 180, the distal constraint 182, and the intermediate constraint 184 from the prosthetic valve 16 and, thus, the prosthetic valve 16 from the delivery catheter 14.

In some other examples, the stake member 30 is additionally or alternatively releasably received through (e.g., threaded through) one or more of the frame portion 210 and/or the cover 212 of the prosthetic valve 16 similarly to the plurality of constraints 28 to help secure the prosthetic valve 16 to the delivery catheter 14 prior to release from the delivery catheter 14. The prosthetic valve 16 is then optionally released from the delivery catheter 14 by pulling the stake member 30 out of the proximal guide 82, the distal guide 84, and the intermediate guide 86, as well as the portions of the prosthetic valve 16 into which the stake member 30 is threaded to release the prosthetic valve 16.

Figure 19:
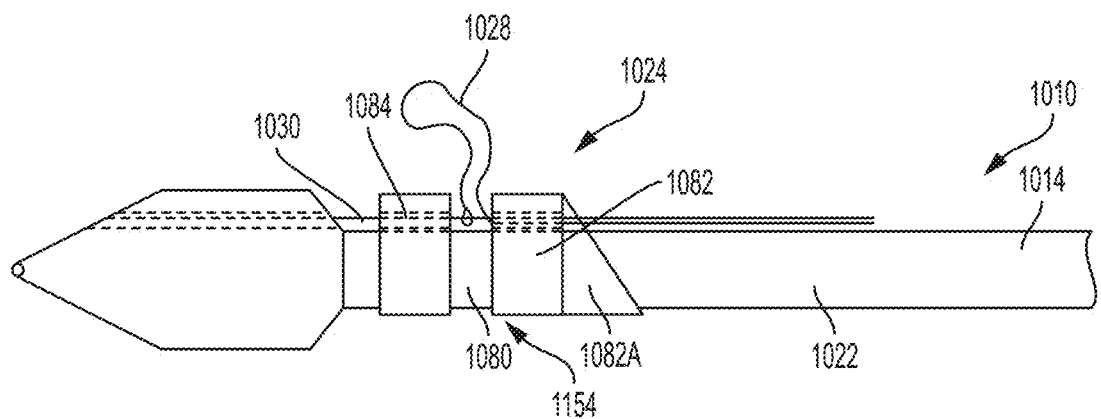
FIGS. 19 and 20 show partial side views of additional embodiments of a transcatheter delivery system, according to some embodiments.
Figure 20:
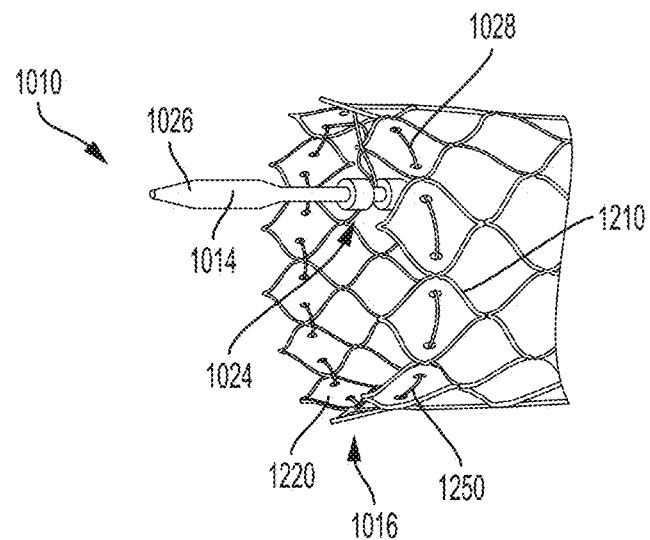

FIGS. 19 and 20 show partial side views of another transcatheter delivery system 1010 having features and components that may be used interchangeably with any of the components of the transcatheter delivery system 10 (and vice versa). For ease of understanding, similar features as those of the transcatheter delivery system 10 are labeled for the transcatheter delivery system 1010 with "1000" added to the corresponding feature reference number. From the foregoing example, it should be apparent that the transcatheter delivery system 10 can be modified for use with an endoprosthesis, such as a stent graft, as shown in FIG. 20.

The transcatheter delivery system 1010 can include a sheath (not shown), such as sheath 12, a delivery catheter 1014, which can be similar to delivery catheter 14, and an implantable device 1016, which can be a stent graft as shown in FIG. 20, or another implantable device, such as prosthetic valve 16, having one or more portions that are maintained in a collapsed configuration by the delivery catheter 1014. It should be noted that the sheath (not shown) or other features, such as constraining sleeves or jackets (not shown), can additionally or alternatively be employed along one or more portions of the implantable device 1016 to assist with maintaining the implantable device 1016 in a collapsed configuration.

Similar to the delivery catheter 14, the delivery catheter 1014, includes an actuation portion (not shown), which can be similar to actuation portion 20, a body portion 1022, a support portion 1024, a tip portion 1026, one or more constraints 1028, which can be similar to the plurality of constraints 1028, and a stake member 1030, which can also be described as a lock wire and which can be similar to the stake member 30. As shown, the transcatheter delivery system 1010 includes a single constraint 1028, although more are contemplated.

As shown, the support portion 1024 is generally configured to be received in the implantable device 1016 and to support the implantable device 1016 through delivery to, and deployment at a desired treatment location in a body of a patient (not shown). As shown, the support portion 1024 includes a shaft 1080, which can be similar to the shaft 80, a proximal guide 1082, which can be similar to the proximal guide 82, and a distal guide 1084, which can be similar to the distal guide 84. As shown, the support portion 1024 does not include an intermediate guide, such as the intermediate guide 86, but such an option is contemplated. The proximal guide 1082 optionally includes a taper, such as an angled portion 1082a that eases retraction of the proximal guide 1082 into a sheath, such as sheath 12 (FIG. 1).

As shown, a first reduced profile section 1154 (e.g., similar to the first reduced profile section 154) is at a location that is intermediate or between the proximal guide 1082 and the distal guide 1084 and can provide additional area for the implantable device 1016 and/or assist with ensuring that the stake member 1030 has sufficient bending strength to facilitate anchoring the constraint 1028 to the stake member 1030 while tensioning the constraint 1028 in a similar manner to the plurality of constraints 28.

As shown in FIG. 20, similarly to the plurality of constraints 28, the constraint 1028 is received through portions of the implantable device 1016 (e.g., through a distal row of closed cells 1250 at a distal end 1220 of a frame portion 1210 of the implantable device 1016). As shown, the constraint 1028 is optionally routed in an "under the frame" configuration in which the constraint 1028 are routed under the frame portion 1210 of the implantable device 1016. In some examples, this routing pattern can help reduce the frictional forces encountered by the constraint 1028 and facilitate reduced tensioning forces used with the constraint 1028.

Although not treated in further detail, it should be readily understood that operation of the transcatheter delivery system 1010 and the constituent components for such operation can be taken from any of the examples and options described in association with the transcatheter delivery system 10, and vice versa.

Figure 21A:
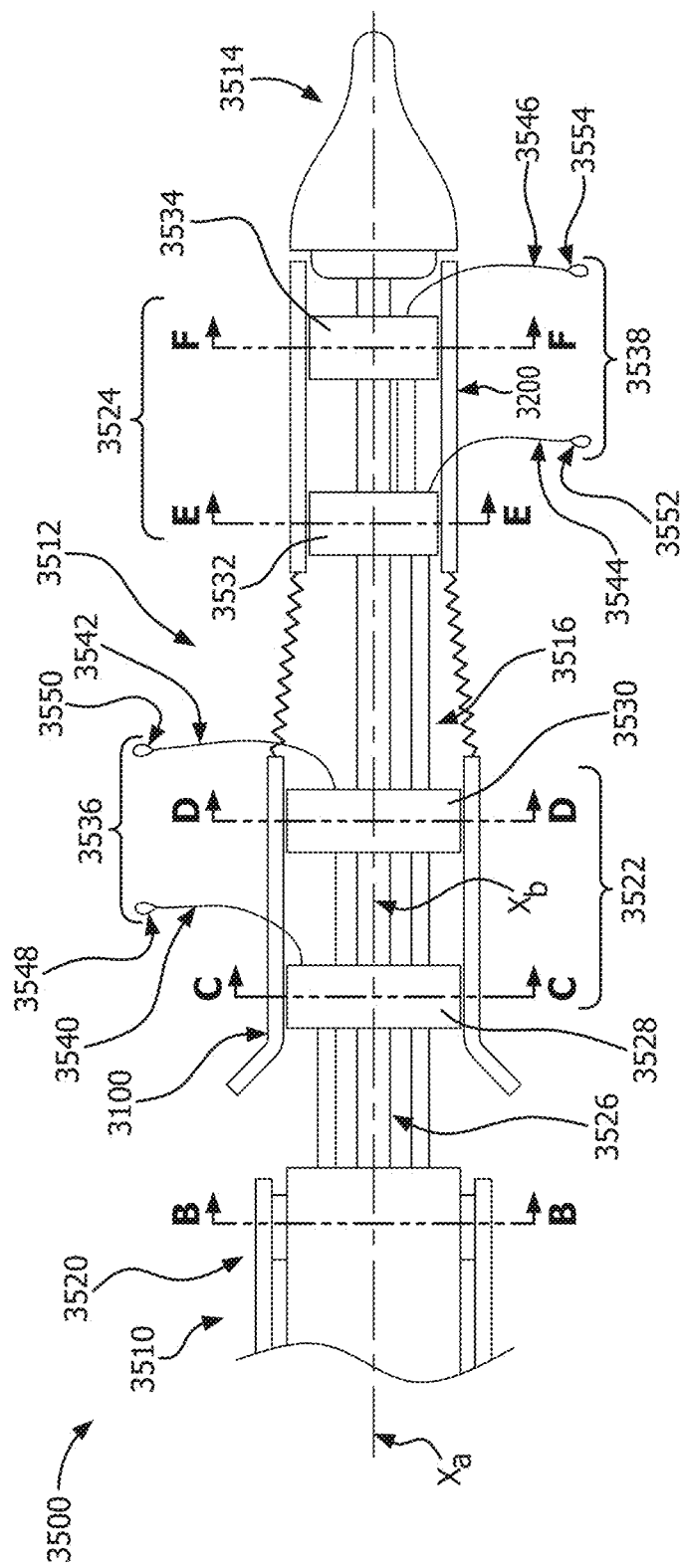
FIG. 21A shows a side view of a transcatheter delivery system, according to some embodiments.

FIG. 21A is a side view of a transcatheter delivery system 3500 includes a delivery catheter 3510 for delivering and deploying a multi-frame implantable device 3000. The multi-frame implantable device 3000 is shown including an outer frame 3100, an inner frame 3200 longitudinally offset from, and optionally nestable within the outer frame following delivery, and a flexible interconnection 3300 between the outer frame 3100 and the inner frame 3200 that is invertible upon nesting the inner frame within the outer frame, although this is an example only and nesting need not be present in all examples. In some examples, the multi-frame implantable device is a prosthetic valve configured for use in repairing or replacing a mitral valve, although a variety of implantable devices are contemplated. The inner frame 3200 is optionally a leaflet frame (i.e., is configured to support a leaflet construct) and the outer frame 3200 is optionally a reinforcing frame (e.g., being configured to reinforce or otherwise support the inner frame). In other examples, the inner frame serves as a reinforcing frame and the outer frame serves as a leaflet frame.

In a similar manner to previously described examples (e.g., delivery catheter 14), the delivery catheter 3510 includes a body portion 3510, a support portion 3512, a tip portion 3514, and one or more constraints, such as a first pair of constraints 3536 and a second pair of constraints 3538, wherein the first pair of constraints 3536 are associated with the first pair of guides 3522 and wherein the second pair of constraints 3538 are associated with the second pair of guides 3524.

In various examples, each pair of constraints is adapted and arranged to interface with a respective one of the outer frame 3100 and the inner frame 3200. The first pair of constraints 3536 generally includes a proximal constraint 3540 and a distal constraint 3542. It will be appreciated that the first pair of constraints 3536 may additionally include an intermediate constraint situated between the proximal and distal constraints 3540 and 3542, as desired, though one is not illustrated. The body portion 3510 defines a central longitudinal axis Xa and has a proximal section (not shown, but which may be similar to other examples, such as the proximal section 40) and a distal section 3520. The body portion 3510 is of suitable length for a user (not shown) to manipulate the delivery device 3500 from a location outside the body of a patient into which the implantable device (not shown in FIG. 21A) is being implanted. Generally, the body portion 3510 is of sufficient flexibility, length, and column strength such that it is suitable for traversing the vasculature or other bodily lumens and conduits within a patient.

FIG. 21B is a sectional view taken along line B-B in FIG. 21A, according to some embodiments. As shown in FIG. 21B, the body portion 3510 has a plurality of lumens 3511 extending within the body portion 3510, which can also be described as passages or channels. In the same manner as prior examples, the plurality of lumens 3511 extend the length of the body portion 3510 through the proximal and distal sections of the delivery catheter. In some embodiments, the lumens 3511 include two or more stake member lumens, such as first stake member lumen 3513 and second stake member lumen 3515. Additionally, in some embodiments the lumens 3511 include a first constraint lumen 3517, a second constraint lumen 3519, a third constraint lumen 3521, and a fourth constraint lumen 3523, although a number of additional lumens (e.g., eight, ten, twelve, etc.), are contemplated. In some embodiments, the lumens 3511 further include a central lumen 3525. In various examples, the first and second stake member lumens 3513 and 3515, as well as the first constraint lumen 3517, the second constraint lumen 3519, the third constraint lumen 3521, and the fourth constraint lumen 3523 are each optionally located at a desired angular position about the central longitudinal axis Xa of the body portion 3510.

As shown, the first stake member lumen 3513 is at a position corresponding to 12 o'clock or 0 degrees, the second stake member lumen 3515 is at a position corresponding to 2 o'clock, or 60 degrees, the first constraint lumen 3517 is at a position corresponding to 4 o'clock or 120 degrees, the second constraint lumen 3519 is at a position corresponding to 6 o'clock or 180 degrees, the third constraint lumen 3521 is at a position corresponding to 8 o'clock or 240 degrees, and the fourth constraint lumen 3523 is at a position corresponding to 10 o'clock, or 270 degrees. Though some examples of angular positions are provided, any number of positions can be employed as desired. As shown, the central lumen 3525 may be positioned coaxially with the longitudinal axis Xa of the body portion 3510, although, again, any number of positions can be employed as desired.

The distal section 3520 of the body portion 3510 is coupled to the support portion 3512 and optionally includes one or more features for assisting with passing the distal section 3520 into, out of, and/or through a constraining sheath. For example, the distal section may include a flare, flange, or taper, to provide an increased diametric profile to the distal section 3520 adjacent the support portion 3512. This increased diametric profile, also described as an outer transverse profile, has a relatively smooth transition to reduce snagging or mechanical friction between a constraining sheath and the distal section 3520 when the distal section 3520 is slid through, extended from, and/or retracted into such a constraining sheath and through the vasculature or other conduits within a patient (not shown).

The support portion 3512 is generally configured to be received in the implantable device 3000 and to support the implantable device 3000 through delivery to, and deployment at a desired treatment location in a body of a patient (not shown). As shown, the support portion 3512 extends from the distal section 3520 of the body portion 3510 and has a central longitudinal axis Xb. In various examples, the central longitudinal axis Xb of the support portion 3512 is parallel with the central longitudinal axis Xa of the body portion 3510. In some examples, the central longitudinal axis Xb is coaxial with the central longitudinal axis Xa. The support portion 3512 includes a shaft 3526. In some examples, the shaft 3526 supports the one or more constraints of the plurality of constraints 3516. The shaft 3526 may be generally the same as include similar features to those of the shaft 80 that have been previously or are subsequently described (e.g., including an enhanced flexibility portion). In various embodiments, the shaft 3526 is a flexible elongate element and may optionally include a central lumen, such as for receiving a guidewire, as those of skill will appreciate.

In various examples, the support potion 3512 further includes a first pair of guides 3522 and a second pair of guides 3524, as discussed further below.

In various embodiments, the shaft 3526 is formed as a hollow tube (e.g., hypotube), for example using nitinol, stainless steel, or other metallic or polymeric materials. In various examples, the shaft 3526 is configured to receive a guidewire (not shown) for guiding the delivery device 3500 to a desired treatment location within the patient's anatomy. If desired, however, the shaft 3526 may also be formed as a solid member without any internal lumen. The shaft 3526 is optionally coupled to the tip portion 3514 (e.g., inserted into and press-fit or bonded to the tip portion 3514), extends a length of the support portion 3512, and is coupled to the body portion 3510 (e.g., extending through the central lumen 3525 and out of the proximal end of the body portion 3510). The shaft 3526 is optionally a single, unitary member, though separate connected components are also contemplated.

In various examples, each pair of guides 3522 and 3524 is adapted and arranged to interface with one or more of the constraints 3516. The first pair of guides 3522 generally includes a proximal guide 3528 and a distal guide 3530. It will be appreciated that the first pair of guides 3522 may additionally include an intermediate guide situated between the proximal and distal guides 3528 and 3530, as desired, though one is not illustrated. In some examples, the second pair of guides 3524 generally includes a proximal guide 3532 and a distal guide 3534. It will be appreciated that the second pair of guides 3524 may likewise additionally include an intermediate guide situated between the proximal and distal guides 3532 and 3534 as desired.

As shown in FIGS. 21C and 21D, the proximal and distal guides 3528 and 3530 of the first pair of guides 3522 are generally cylindrical overall, having transverse outer profiles that are cylindrical, which also corresponds to a transverse outer profile that is circular in transverse cross-section. It will be appreciated that although cylindrical profiles are contemplated, any of a variety of tapers, steps, chamfers and other features is also contemplated. In some examples the proximal and distal guides 3528 and 3530 are configured to support the inner frame 3200.

In various examples, each of the proximal and distal guides 3528 and 3530 of the first pair of guides 3522 defines a central longitudinal axis (not separately labeled) that is coaxial with the central longitudinal axis Xa of the support portion 3512 and by transitive theory, the central longitudinal axis of the shaft 3526, according to some examples.

As shown in FIG. 21C, in some embodiments, the proximal guide 3528 includes a central lumen 3527 through which the shaft 3526 is received, for coupling the proximal guide 3528 to the shaft 3526. As shown, the proximal guide 3528 also includes a plurality of passages 3529, also described as channels or lumens. In various examples, the plurality of passages 3529 includes one or more stake member passages, such as first stake member passage 3533 and second stake member passage 3535. Additionally, in some embodiments the passages 3529 include a first constraint passage 3537, a second constraint passage 3539, a third constraint passage 3541, and a fourth constraint passage 3543, although a number of additional passages (e.g., eight, ten, twelve, etc.), are contemplated. In various examples, the first and second stake member passages 3533 and 3535, as well as the first constraint passage 3537, the second constraint passage 3539, the third constraint passage 3541, and the fourth constraint passage 3543 are each optionally located at a desired angular position about the central longitudinal axis Xb of the support portion 3512.

As shown, the stake member passages and the constraint member passages correspond in angle and in offset with the stake member lumens and the constraint member lumens of the body portion 3510, discussed above. For example, the first stake member passage 3533 corresponds with the first stake member lumen 3513 in that the first stake member passage 3533 is at an angular position corresponding to 12 o'clock or 0 degrees.

As seen with reference between FIGS. 21C and 21D, the distal guide 3530 is substantially similar to the proximal guide 3528. In some examples, the distal guide 3530 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide 3530 also defines a central longitudinal axis (not separately labeled) that is coaxial with the central longitudinal axis Xa of the support portion 3512 and by transitive theory, the central longitudinal axis of the shaft 3526 (as well as the proximal guide 3528), according to some examples.

As shown in FIG. 21D, in some embodiments, the distal guide 3530 includes a central lumen 3545 through which the shaft 3526 is received, for coupling the distal guide 3530 to the shaft 3526. As shown, the distal guide 3530 also includes a plurality of passages 3547, also described as channels or lumens. In various examples, the plurality of passages 3547 include one or more stake member passages, such as first stake member passage 3553 and second stake member passage 3555. Additionally, in some embodiments the passages 3547 include a first constraint passage 3557, a second constraint passage 3559, a third constraint passage 3561, and a fourth constraint passage 3563, although a number of additional passages (e.g., eight, ten, twelve, etc.), are contemplated. In various examples, the first and second stake member passages 3553 and 3555, as well as the first constraint passage 3557, the second constraint passage 3559, the third constraint passage 3561, and the fourth constraint passage 3563 are each optionally located at a desired angular position about the central longitudinal axis Xb of the support portion 3512.

As shown, the stake member passages and the constraint member passages correspond in angle and in offset with the stake member lumens and the constraint member passages of the proximal guide 3528, discussed above. For example, the first stake member passage 3553 corresponds with the first stake member passage 3533 in that the first stake member passage 3553 is at an angular position corresponding to 12 o'clock or 0 degrees.

In various embodiments, each of the passages 3529 of the proximal guide 3528 is aligned with a corresponding passage of the plurality of passages 3547 of the distal guide 3530. In other words, the first stake member passage 3533 is angularly aligned with the first stake member passage 3553, and the first constraint passage 3537 with the first constraint passage 3557, etc., as mentioned above. It will be appreciated, however, that one or more of the plurality of passages 3529 and the plurality of passages 3547 may be angularly misaligned, or out of alignment with one another. Moreover, the distal guide 3530 need not have the same number of passages as the proximal guide 3528, as discussed below.

As shown in FIGS. 21E and 21F, the proximal and distal guides 3532 and 3534 of the second pair of guides 3524 are generally cylindrical overall, having transverse outer profiles that are cylindrical, which also corresponds to a transverse outer profile that is circular in transverse cross-section. It will be appreciated that although cylindrical profiles are contemplated, any of a variety of tapers, steps, chamfers and other features is also contemplated. In some examples, a diameter of the proximal and distal guides 3532 and 3534 of the second pair of guides 3524 is generally less than a diameter of the proximal and distal guides 3528 and 3530 of the second pair of guides 3524. In some examples such a configuration provides that the inner frame 3200 can be proximally retracted (e.g., telescoped) into an interior region defined by the outer frame 3100. That is, by providing proximal and distal guides 3532 and 3534 that have a smaller diameter, the inner frame 3200 can be reduced to a smaller cross sections suitable for being received within the outer frame 3100. In some examples the proximal and distal guides 3532 and 3534 are configured to support the inner frame 3200.

In various examples, each of the proximal and distal guides 3532 and 3534 of the second pair of guides 3524 defines a central longitudinal axis (not separately labeled) that is coaxial with the central longitudinal axis Xa of the support portion 3512 and by transitive theory, the central longitudinal axis of the shaft 3526, according to some examples.

As shown in FIG. 21E, in some embodiments, the proximal guide 3532 includes a central lumen 3565 through which the shaft 3526 is received, for coupling the proximal guide 3532 to the shaft 3526. As shown, the proximal guide 3532 also includes a plurality of passages 3567, also described as channels or lumens. In various examples, the plurality of passages 3567 include second stake member passage 3575, a first constraint passage 3577, and a second constraint passage 3579, although a number of additional passages (e.g., eight, ten, twelve, etc.), are contemplated. In various examples, the second stake member passage 3575, as well as the first constraint passage 3577 and the second constraint passage 3579, are each optionally located at a desired angular position about the central longitudinal axis Xb of the support portion 3512.

As shown, the stake member passage and the constraint member passages correspond in angle and in offset with the stake member passages and the constraint member passages of the distal guide 3530, discussed above. For example, the second stake member passage 3575 corresponds with the second stake member passage 3555 in that the second stake member passage 3575 is at an angular position corresponding to 2 o'clock or 60 degrees.

As seen with reference between FIGS. 21E and 21F, the distal guide 3534 is substantially similar to the proximal guide 3532. In some examples, the distal guide 3534 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide 3534 also defines a central longitudinal axis (not separately labeled) that is coaxial with the central longitudinal axis Xa of the support portion 3512 and by transitive theory, the central longitudinal axis of the shaft 3526 (as well as the proximal guide 3532), according to some examples.

As shown in FIG. 21F, in some embodiments, the distal guide 3534 includes a central lumen 3581 through which the shaft 3526 is received, for coupling the distal guide 3534 to the shaft 3526. As shown, the distal guide 3534 also includes a plurality of passages 3583, also described as channels or lumens. In various examples, the plurality of passages 3583 include second stake member passage 3585, a first constraint passage 3587, and a second constraint passage 3589, although a number of additional passages (e.g., eight, ten, twelve, etc.), are contemplated. In various examples, the second stake member passage 3585, as well as the first constraint passage 3587 and the second constraint passage 3589, are each optionally located at a desired angular position about the central longitudinal axis Xb of the support portion 3512.

As shown, the stake member passage and the constraint member passages correspond in angle and in offset with the stake member passages and the constraint member passages of the proximal guide 3532, discussed above. For example, the second stake member passage 3585 corresponds with the second stake member passage 3575 in that the second stake member passage 3585 is at an angular position corresponding to 2 o'clock or 60 degrees.

As shown in FIG. 21A, the plurality of constraints 3516 comprises a first pair of constraints 3536 and a second pair of constraints 3538, wherein the first pair of constraints 3536 are associated with the first pair of guides 3522 and wherein the second pair of constraints 3538 are associated with the second pair of guides 3524. In various examples, each pair of constraints is adapted and arranged to interface with a respective one of the outer frame 3100 and the inner frame 3200. The first pair of constraints 3536 generally includes a proximal constraint 3540 and a distal constraint 3542. It will be appreciated that the first pair of constraints 3536 may additionally include an intermediate constraint situated between the proximal and distal constraints 3540 and 3542, as desired, though one is not illustrated. The second pair of constraints 3538 generally includes a proximal constraint 3544 and a distal constraint 3546. It will be appreciated that the second pair of constraints 3538 may likewise additionally include an intermediate constraint situated between the proximal and distal constraints 3544 and 3546, as desired, though one is not illustrated.

In some embodiments, each of the plurality of constraints 3516 is formed as a fiber, strand, wire, combinations thereof or the like, and may be braided, wound, extruded, or otherwise formed of metallic or polymeric materials. For example, each of the constraints 3516 may be formed from braided strands of material, such as UHMWPE or ePTFE. Although three are shown, any number of constraints (e.g., one, two, four, nine, etc.) are contemplated. In some embodiments, the proximal constraint 3540 includes a catch 3548 in the form of a terminal, closed loop or eyelet, for example. The catch 3548 is optionally formed using braiding methods (e.g., by twisting the braid into itself or through a continuous braiding method that forks a single strand into two separates strands and then rebraids them into a single strand to form an eyelet). The distal constraint 3542 similarly includes a catch 3550, as does the proximal constraint 3544, which includes catch 3552. Distal constraint 3546 includes a catch 3554.

The transcatheter delivery system 3510 can include a sheath (not shown), such as sheath 12, a delivery catheter 3514, which can be similar to delivery catheter 14, and an implantable device, which can be a valve or another implantable device having one or more portions that are maintained in a collapsed configuration by the delivery catheter 3514. It should be noted that the sheath (not shown) or other features, such as constraining sleeves or jackets (not shown), can additionally or alternatively be employed along one or more portions of the implantable device (not shown) to assist with maintaining the implantable device in a collapsed configuration. The delivery catheter 3514 also includes two or more stake members, which can also be described as a lock wire and which can each be similar to the stake member 30.

Figure 21G:
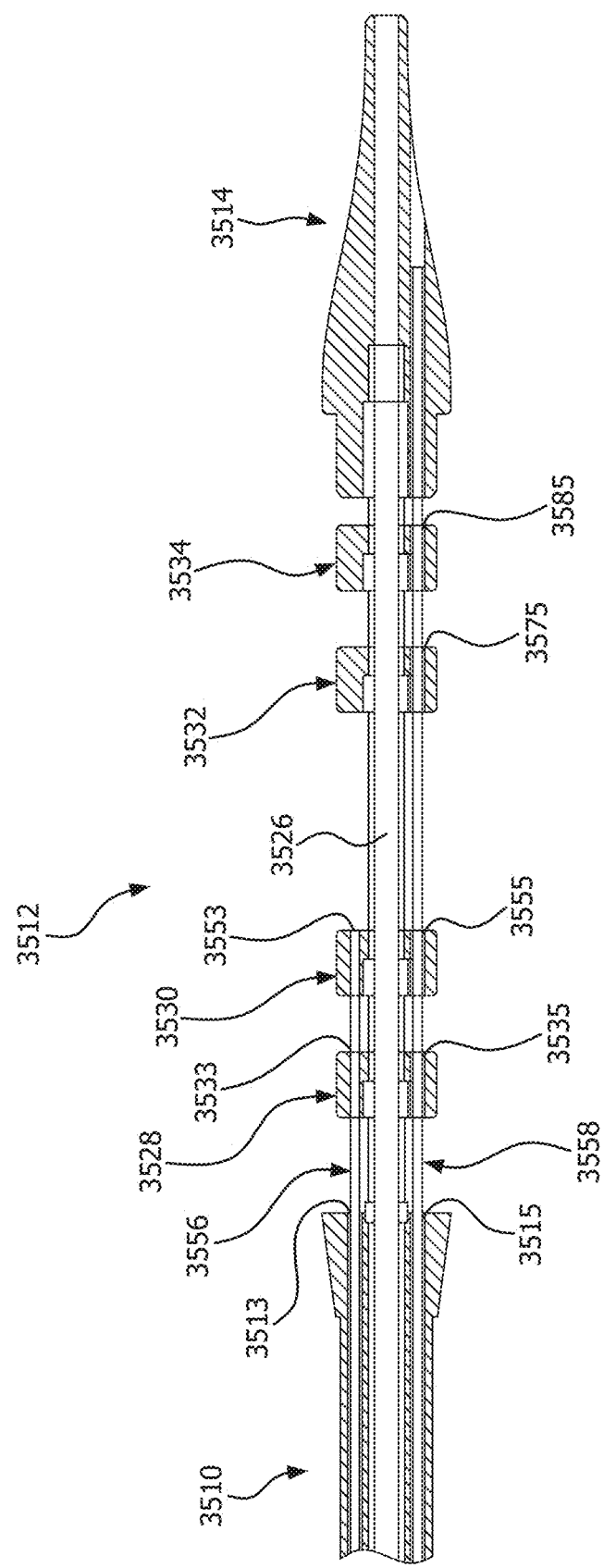
FIG. 21G shows a full section view of a transcatheter delivery system taken along a longitudinal axis of the system, according to some embodiments.

In various examples, the stake members include a first stake member 3556 and a second stake member 3558. The first stake member 3556 is generally associated with securing or otherwise engaging with the first pair of constraints (not shown) and the first pair of guides 3522, while the second stake member 3558 is generally associated with securing or otherwise engaging with the second pair of constraints (not shown) and the second pair of guides 3084. For example, as shown in FIG. 21G, the first stake member 3556 extends through first stake member lumen 3513 of the body portion 3510 and into the first stake member passages 3533 and 3553 of proximal and distal guides 3528 and 3530 of the first pair of guides 3522. Likewise, as shown in FIG. 21G, the second stake member 3558 extends through second stake member lumen 3515 of the body portion 3510, through second stake member passages 3535 and 3555 of the proximal and distal guides 3528 and 3530 of the first pair of guides 3522, and into the second stake member passages 3575 and 3585 of the proximal and distal guides 3532 and 3530 of the second pair of guides 3524.

Figure 21H:
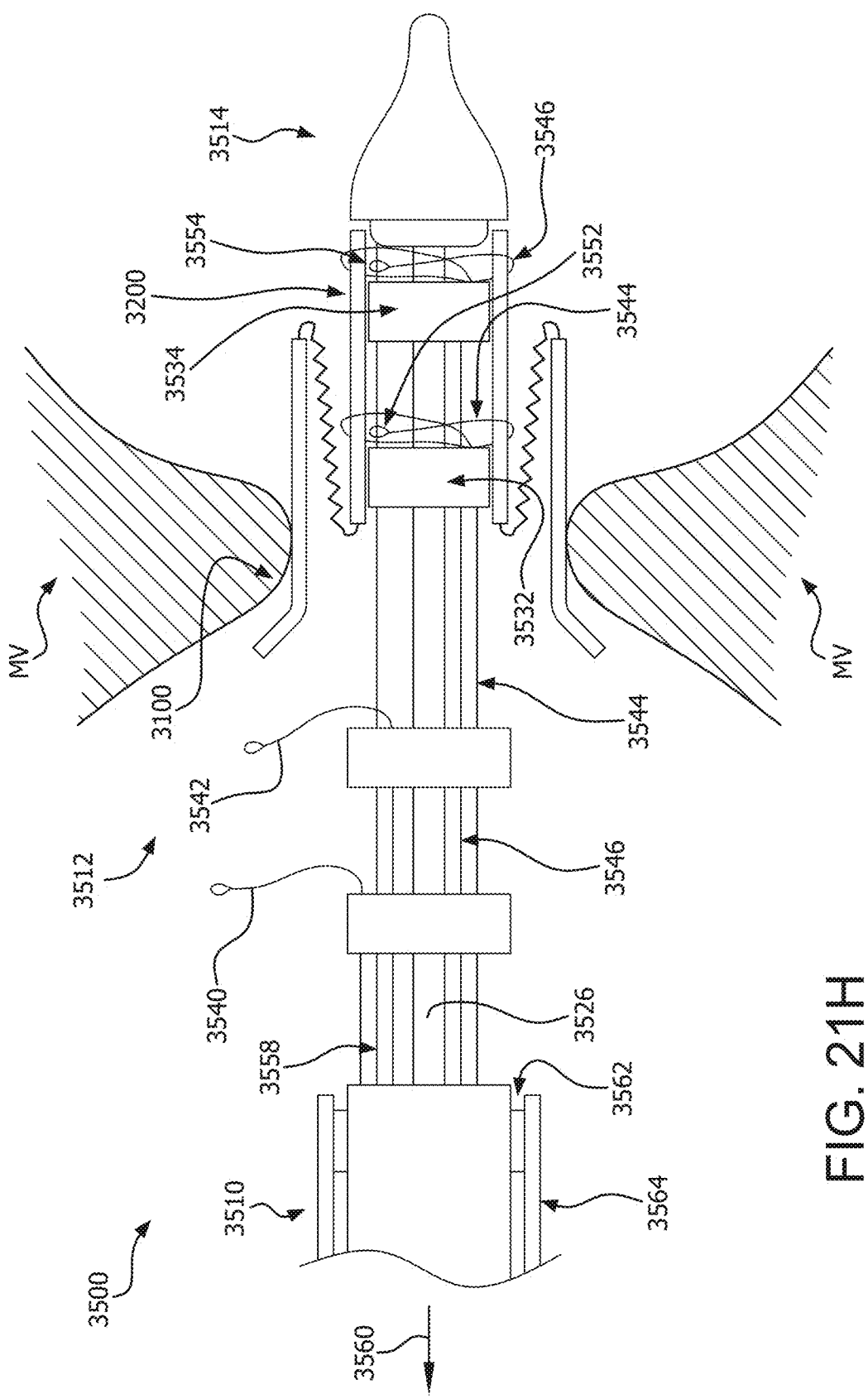
FIG. 21H shows an example of a delivery operation, according to some embodiments.

Turing now to FIG. 21H, a nonlimiting delivery operation in accordance with the above discussed examples and embodiments is illustrated and described. As shown, the first pair of constraints 3536 (e.g., proximal and distal constraints 3540 and 3542) has been released from the first stake member 3556 such that the outer frame 1100 is operable to expand and engage a valve annulus of a mitral valve, for example. However, as shown, proximal and distal constraints 3544 and 3546 remain coupled with second stake member 3558 and the leaflet frame 3200.

Though not illustrated as such in FIG. 21H, it will be understood that in actuality, each of the proximal and distal constraints 3544 and 3546 are coupled (e.g., woven or otherwise passed through) portions of the inner frame 3200.

With the outer frame 3100 unconstrained and the leaflet frame 3200 at least partially constrained by one or more of the proximal and distal constraints 3544 and 3546, the delivery device 3500 can be proximally withdrawn in the direction of arrow 3560 (e.g., proximally translated) relative to the valve annulus and the outer frame 3100 such that the inner frame 3200 is proximally withdrawn into the interior region defined by the outer frame 3100, as discussed herein. In various examples, the delivery device 3500 is proximally withdrawn until the inner frame 3200 becomes nested within the outer frame 3100, as discussed herein.

In some examples, after releasing the first pair of constraints 3536 from the first stake member 3556 and the outer frame 1100, and before proximally withdrawing the delivery device 3500 and the inner frame 3200, a tension in one or more of the proximal and distal constraints 3544 and 3546 may be reduced, thereby enabling one or more of the inner frame 3200 to partially deploy. Thus, in such examples, the delivery device 3500 is operable to partially deploy the inner frame 3200 prior to proximally withdrawing the delivery device 3500 and the inner frame 3200.

It should be appreciated that while the above discussed examples and embodiments include a delivery system including a plurality of stake members, the delivery system may be operable with a single stake member. For instance, in some examples the stake member may engage and retain each of a first constraint extending about the outer frame 3100 and a second constraint extending about the inner frame 3200. In such examples the stake member is generally routed through one or more guides such that proximally retracting proximal end of the stake member results in a distal end of the stake member advancing proximally along the support portion of the delivery system such that the constraint extending about the outer frame 1100 can be released prior to releasing the constraint extending about the leaflet frame 1200.

FIGS. 22A-22D show additional design concepts for the proximal guide 82, the distal guide 84, and/or the intermediate guide 86, as well as the proximal guide 1082 and/or the distal guide 1084, in the form of a guide 2082. In various examples, the guide 2082 includes a filament formed into at least one loop adapted to wrap around and couple to an outer circumference of a shaft 2080 (e.g., support portion) and to define at least one constraint passage between the shaft 2080 and the filament. Similar to the previously-described guide designs, the constraint passage of the guide 2082 is configured to receive a constraint (e.g., a fiber) that extends longitudinally through the constraint passage and is then directed transversely/radially outward to form a releasable, looped configuration to define a constraining loop (e.g., the proximal constraining loop 195). In various examples, the looped filament design for the guide 2082 can help provide ease of manufacturability, a reduced overall guide profile for a higher level of diametric compaction of a device over the guide, and resistance to deflection of the stake member when placed under load by the constraint (e.g., when the constraint is tensioned).

FIG. 22A is a perspective view of the guide 2082 mounted on a section of a shaft 2080 (e.g., support portion 24 of shaft 80 or support portion 1024 of shaft 1080) of a transcatheter delivery system (e.g., the transcatheter delivery system 10 or the transcatheter delivery system 1010).

FIG. 22B is a bottom view of the guide 2082 as mounted on the shaft 2080. As shown, the guide 2082 includes one or more turns of a filament (e.g., a wire, fiber, braid, bead, or hypotube) wrapped or otherwise disposed around the shaft 80. In various examples, the filament forming any of the guides resiliently retain their shape, although less resilient, more flexible filaments may be employed as desired.

FIG. 22C is an end view of the guide 2082, according to some embodiments. As shown, the guide 2082 defines a central longitudinal axis (not separately labeled) that is coaxial with the central longitudinal axis of the shaft 2080, according to some examples. As shown, the guide 2082 includes a central lumen 2088 through which the shaft 2080 is received, for coupling the guide 2082 to the shaft 2080.

As shown in FIGS. 22A and 22B, the guide 2082 defines a plurality of turns, or revolutions around the shaft 2080, including a first base turn 2090 (also described as a securing loop), a first eyelet turn 2092 (also described as a guide loop), second eyelet turn 2094 (also described as a guide loop), and a second base turn 2096 (also described as a securing loop), although any number of revolutions, turns, rings, loops, or passes around the shaft 2080 are contemplated. Though the guide 2082 is shown as a single, continuous length of material extending about the guide 2082 multiple times along a helical path, or other longitudinal and circumferential path, in other examples separate turns (e.g., separate rings or loops) are also contemplated for each of the turns 2090, 2092, 2094, 2096. As shown, the first base turn 2090 and the second base turn 2096 are each cylindrical overall and may be relatively tightly engaged to the outer circumference of the shaft 80 (e.g., to help secure the guide 2082 to the shaft 2080).

The first eyelet turn 2092 has an eccentric profile relative to the shaft 2080 and defines a stake member passage 2092A, also described as a stake member passage 2092A. The second eyelet turn 2094 has an eccentric profile relative to the shaft 2080 and defines a constraint passage 2094A. The stake member passage 2092A is configured to receive a stake member, such as the stake member 30 or the stake member 1030 similarly to stake member passages of any of the proximal, intermediate, or distal guides previously described. The constraint passage 2094A is configured to receive a constraint, such as one of the plurality of constraints 28 or one of the plurality of constraints 1028, similarly to constraint passages of any of the proximal, intermediate, or distal guides previously described.

The stake member passage 2092A and the constraint passage 2094A are each optionally located at a desired angular position about the central longitudinal axis of the shaft 2080. For example, the stake member passage 2092A and the constraint passage 2094A are optionally located at the same angular location, and serve a similar function, to the stake member passage 92 and the first constraint passage 94, respectively, of the transcatheter delivery system 10 or similar features of the transcatheter delivery system 1010.

As shown, the stake member passage 2092A is at an angular position corresponding to 12 o'clock or 0 degrees and the constraint passage 2094A is at an angular position corresponding to 11 o'clock, or −15 degrees. Though some examples of angular positions are provided, any number of angular positions can be employed as desired.

The guide 2082 has a maximum transverse outer profile at one or more transverse cross-sections along the length of the guide 20882 and a minimum transverse outer profile at one or more transverse cross-sections along the length of the guide 2082. For example, the guide 2082 optionally defines a maximum transverse outer profile at the first eyelet turn 2092 and/or the second eyelet turn 2094, and a minimum transverse outer profile at the first base turn 2090 and/or at the second base turn 2096, although any of a variety of outer profiles are contemplated, including tapers, steps, chamfers and other features. Generally, the arrangement of the first eyelet turn 2092 and the second eyelet turn 2094 is selected to minimize overall profile, thus helping to facilitate maximum diametric compaction of a device around the guide 2082.

The configuration associated with the guide 2082 can be employed for the proximal guide 82 and/or the intermediate guide 86 as desired. For example, a second guide of the same or similar design to that of the guide 2082 can be implemented such that both the proximal guide 82 and the intermediate guide 86 have a design corresponding to the design of the guide 2082. In use, where a design such as that shown in FIG. 22C is utilized for the proximal guide 82 of the transcatheter delivery system 10, rather than passing through a second constraint passage, such as the second constraint passage 96, the distal constraint 182 may simply bypass, or extend next to the guide 2082, extending alongside the stake member passage 2092A.

FIG. 22D shows an end view of a variation of the guide 2082, where the position of the stake member passage 2092A is at a similar angular position to that shown in FIG. 22C, but the constraint passage 2094A is at an angular position corresponding to 1 o'clock, or +15 degrees. Though some examples of angular positions are provided, any number of angular positions can be employed as desired. The arrangement shown in FIG. 22D can be employed as a replacement for that previously described for the distal guide 84 of the transcatheter delivery system 10. The constraint passage 2094A as shown in FIG. 22D is optionally employed in a similar manner as the second constraint passage 108 of the distal guide 84.

The guide 2082 is optionally formed and attached to the shaft 2080 using any of a variety of methods, including wrapping or winding a filament (e.g., wire) around the shaft 2080 with sufficient tension such that the guide 2082 remains at a desired location with a desired orientation on the shaft 2080. If desired, heat treatments, adhesives, or other methods may be employed to facilitate securing the guide 2082 to the shaft. Additionally, the guide 2082 can be formed separately from the shaft 2080 with an inner diameter smaller than the outer diameter of the shaft 2080, and then be expanded, placed over the shaft, and allowed to recoil such that a bias/spring force assists with coupling the guide 2082 and shaft 2080. Multiple guides like the guide 2082 may be attached to the shaft 2080 using any of these techniques. The guide 2082 may be formed of any of a variety of metallic or polymeric materials, including shape memory materials, nickel titanium alloys, stainless steel alloys, fluoropolymers, and others.

FIGS. 22A-22F show more design concepts for the proximal guide 82, the distal guide 84, and/or the intermediate guide 86, as well as the proximal guide 1082 and/or the distal guide 1084, in the form of a guide 2182.

Figure 23B:
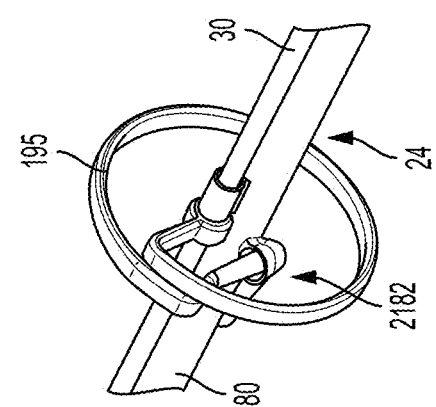
FIGS. 23A-23F show additional examples of designs for proximal, distal, and intermediate guides, according to some embodiments.
Figure 23C:
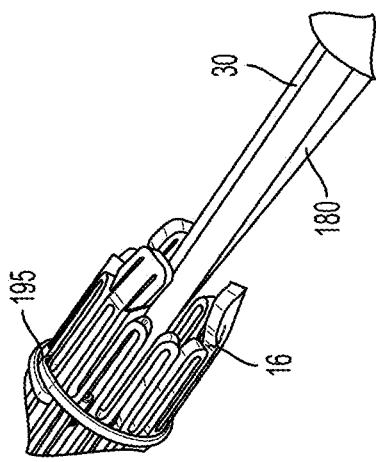

In the examples shown, the guide 2182 is generally described in association with use in place of the proximal guide 82 of the transcatheter delivery system 10. From this example, it should be readily understood that any of the proximal, intermediate or distal guides previously described in association with the transcatheter delivery system 10 or transcatheter delivery system 1010 may be configured in the same or similar manner as the guide 2182. As with the other guide configurations, the guide 2182 is configured to receive a constraint (e.g., the proximal constraint 180 as shown in FIG. 23B) that extends longitudinally through the constraint passage and is then redirected transversely/radially outward by the guide 2182 to form a releasable, looped configuration to define a constraining loop (e.g., the proximal constraining loop 195 as shown in FIGS. 23A-23C).

Figure 23A:
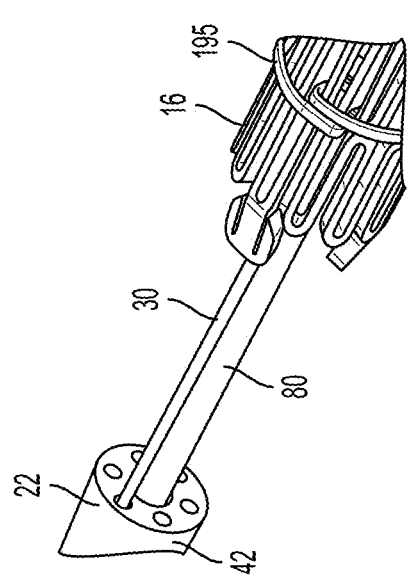

FIG. 23A shows an area where the guide 2182 (hidden in FIG. 23A) could be located with regard to the transcatheter delivery system 10 (e.g., as a proximal guide located under the prosthetic valve 16 for maintaining the proximal constraining loop 195). FIG. 23B is the same arrangement as 22A, but from a reverse angle. FIG. 23C shows the guide 2182 with the prosthetic valve 16 not shown for ease of visualization of the interaction between the guide 2182 and the proximal constraining loop 195 and the guide 2182 and the stake member 30 in use.

Figure 23D:
Figure 23E:
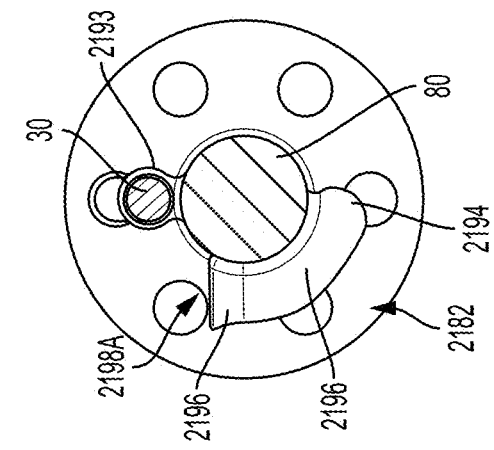
Figure 23F:
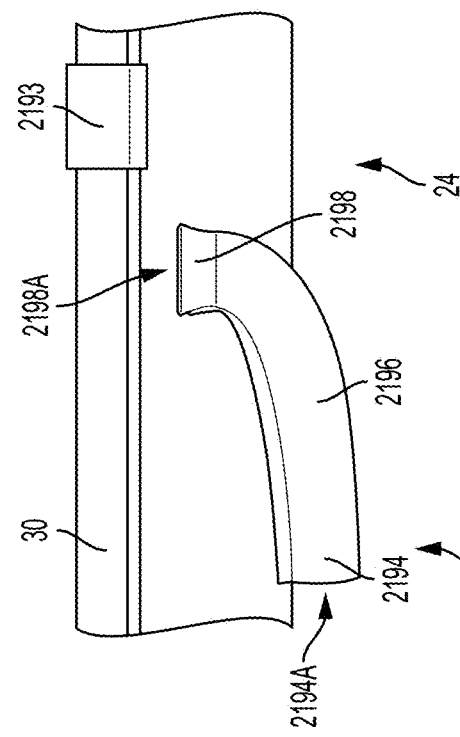

FIG. 23D is a top view of the region of the support portion 24 proximate the guide 2182. FIG. 23E is an end view of the support portion 24 proximate the guide 2182 showing the distal section 42 of the body portion 22, and FIG. 23F is a side view of approximately the same region as FIG. 23D. In FIG. 23E, the transverse angular position relative to the top of the support portion 24 corresponding to "12 o'clock" is labeled for ease of reference. For reference, the proximal constraint 180 is not shown in FIGS. 23D-23F for ease of visualization.

As shown, the guide 2182 includes a fiber guide tube 2192 and optionally includes a stake guide tube 2193, which can also be described as a lock wire guide tube 2193. The fiber guide tube 2192 and the stake guide tube 2193 are optionally formed separately and located proximate one another as shown. Each of the fiber guide tube 2192 and the stake guide tube 2193 is optionally individually formed as a continuous tubular member, such as a hypotube. The fiber guide tube 2192 and the stake guide tube 2193 are optionally formed of similar or dissimilar materials as desired, including any of a variety of metallic or polymeric materials. In some examples, the fiber guide tube 2192 and the stake guide tube 2193 are formed of hypotube material. The fiber guide tube 2192 and the stake guide tube 2193 may be formed integrally with the shaft 80, or may be separate formed and coupled to the shaft 80 using any of a variety of fastening mechanisms, including welding, adhesives, fasteners, or others.

As shown, the fiber guide tube 2192 includes a receiving portion 2194, a transition portion 2196, and a take-off portion 2198, where the receiving portion 2194 is located proximal to the take-off portion 2198, and the transition portion 2196 is located between the receiving portion 2194 and the take-off portion 2198 along the shaft 80. As shown, the receiving portion 2194 extends along the outer circumference, or surface of the shaft 80 at a first transverse angular position relative to the top of the support portion 24, and extends at a first, longitudinal angle relative to the longitudinal axis of the shaft 80 and the support portion 24. For example, the receiving portion 2194 optionally extends at a first longitudinal angle at, or close to zero degrees (plus or minus 15 degrees) as measured relative to the longitudinal axis of the shaft 80. The receiving portion 2194 is located at a first transverse angular position about the outer surface of the shaft 80. For example, the receiving portion 2194 is optionally at a first transverse angular position of zero degrees, or 6 o'clock relative to a coordinate system in which the top of the shaft 80 is at zero degrees, or 12 o'clock.

The transition portion 2196 of the fiber guide tube 2192 extends, or wraps around a portion of the outer circumference of the shaft 80, and thus the support portion 24, in a longitudinal and circumferential fashion (e.g., helically substantially helically, or otherwise curving/extending along the surface of the support portion 24), changing the longitudinal angle and transverse angular position of the fiber guide tube 2192 between the receiving portion 2194 and the take-off portion 2198.

The take-off portion 2198 extends along the outer circumference, or surface of the shaft 80 at a second transverse angular position, and extends at a second longitudinal angle. For example, the take-off portion 2198 is optionally at a second longitudinal angle at, or close to 90 degrees (plus or minus 15 degrees) as measured relative to the longitudinal axis of the shaft 80. The take-off portion 2198 is located at a second transverse angular position about the outer surface of the shaft 80 of 135 degrees, or 9 o'clock relative to a coordinate system in which the top of the shaft 80 is zero degrees, or 12 o'clock.

In some examples, the first longitudinal angle and the second longitudinal angle are offset by 45 degrees or more, such as by 90 degrees, and the first transverse angular position and the second transverse angular position are offset by 45 degrees or more, such as by 90 degrees.

In operational terms, the fiber guide tube 2192 is configured to receive a constraint (e.g., the proximal constraint 180) at a first longitudinal angle of extension (e.g., at or close to the first longitudinal angle of the receiving portion 2194) at the first transverse angular position about the circumference of the shaft 80. The fiber guide tube 2192 then guides, or transitions the direction of extension of the constraint to a second longitudinal angle of extension corresponding to the second longitudinal angle of the take-off portion 2198 at the second transverse angular position about the circumference of the shaft 80.

In some examples, the first longitudinal angle of extension and the second longitudinal angle of extension of the constraint as it passes through the fiber guide tube 2192 are offset from one another by 45 degrees or more, such as by 90 degrees, and similarly the first transverse angular position and the second transverse angular position are offset by 45 degrees or more, such as by 90 degrees.

In the example of FIGS. 22C-22F, the fiber guide tube 2192 is configured to receive a constraint in a generally longitudinally extending direction with a first longitudinal angle of extension of zero or within 15 degrees of zero, at a first transverse angular position corresponding to 90 degrees or 6 o'clock. The fiber guide tube 2192 transitions, or guides the direction of extension of the constraint to a generally perpendicularly extending direction, at a second longitudinal angle of extension of 90 degrees, or within 15 degrees thereof, at a second transverse angular position corresponding to 135 degrees or 9 o'clock. However, the fiber guide tube 2192 can be readily modified to provide any of a variety changes in longitudinal angles of extension and transverse angular positions to a constraint (e.g., the proximal constraint 180) as the constraint passes through the fiber guide tube 2192.

In some examples, the take-off portion 2198 defines an outlet 2198A of the fiber guide tube 2192 which is outwardly flared. The outward flared configuration can assist with avoiding chafing and facilitating smooth actuation of a constraint passing through the fiber guide tube 2192. Similarly, the receiving portion 2194 optionally defines an inlet 2194A of the fiber guide tube 2192 which is outwardly flared. Again, the outward flared configuration of the inlet 2194A can assist with avoiding chafing and facilitating smooth actuation of a constraint passing through the fiber guide tube 2192.

The stake guide tube 2193 similarly extends along the outer circumference, or surface of the shaft 80 at a desired transverse angular position and extends at a desired longitudinal angle. In the example shown, the transverse angular position is zero degrees or 12 o'clock and the longitudinal angle is zero degrees, although a variety of transverse angular positions and longitudinal angles are contemplated. As with the stake member passages of the guides previously described (e.g., stake member passage 92 of the proximal guide 82), the stake guide tube 2193 is configured to receive the stake member 30, and will generally be positioned at a location to do so.

As shown in FIG. 23D, the stake guide tube 2193 is optionally distally offset from the fiber guide tube 2192 a desired amount (e.g., between 1 mm and 10 mm), which can help avoid overlapping or self-interference of the constraint (e.g., the proximal constraint 180) as it forms a constraining loop (e.g., the proximal constraining loop 195). The operation of the proximal, distal, and intermediate guide examples previously provided applies equally to the guide 2182, and it should be understood the configuration of FIGS. 23A-23F is optionally employed as an alternative the configurations previously described.

Figure 25:
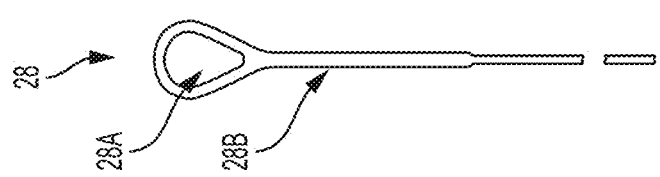
FIGS. 24A-24C and 25 show various examples of options for forming one or more of a plurality of constraints, according to some embodiments.
Figure 24C:
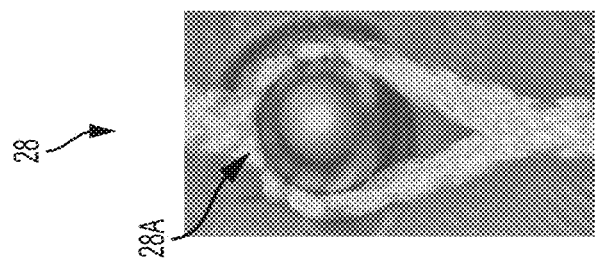
Figure 24B:
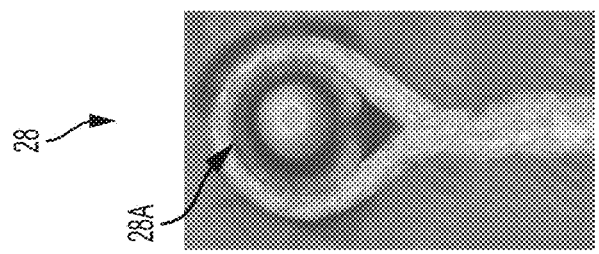
Figure 24A:
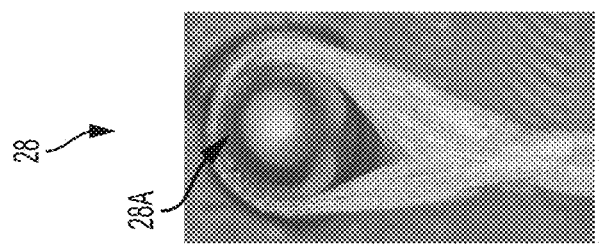

FIGS. 24A-24C and 24 show various options for one or more of the plurality of constraints 28, according to some embodiments. As shown, one of the plurality of constraints 28 may be secured in a looped fashion (e.g., into an eye splice) to form a catch 28A (e.g., such as the catch 190). FIG. 24A shows an example of an eye splice where a first number of strands have been looped back and braided into themselves, FIG. 24B shows another example with a greater number of strands that have been looped back and braided into themselves, and FIG. 24C shows still another example where the catch 28A is formed via a continuous braiding method that forks a single strand into two separates strands and then re-braids them into a single strand to form the catch 28A where the strand has been separated. As shown in FIG. 25, with the examples of FIGS. 24A and 24B, the catch 28A is optionally formed using an eye splice method in which a desired length of the respective one of the plurality of constraints 28 is re-braided, or "buried," into itself to form a buried length 28B of material. As previously referenced, the constraint 1028 may take a similar form as one or more of the plurality of constraints 28. It has been found that these types of formation techniques not only provide strong constraints and catches, but also provide the small diametric profiles generally required in delivery systems for implantable devices.

FIGS. 26-31 show additional examples of features for the frame portion 210 usable for securing one of the plurality of constraints 28 to the frame portion 210 of the prosthetic valve 16. Consistent with concepts previously described, frame portion 1210 can include similar features and the constraint 1028 can be similarly secured to the frame portion 1210 as desired. As shown in FIG. 26A, one or more of the plurality of rows of frame members 224 (e.g., the distal row 230 and/or the proximal row 232 shown in FIG. 12) optionally includes a plurality of circumferentially-oriented eyelets 224A. In some examples, the plurality of circumferentially-oriented eyelets 224A are formed in the proximal row 232 in the proximal-facing apices 228 at the proximal end 222 of the frame portion 210. Again, these features can additionally or alternatively be located elsewhere in the frame design (e.g., proximate the distal end 220). Additionally, although the plurality of circumferentially-oriented eyelets 224A are shown in each of the proximal-facing apices 226, such an arrangement need not always be the case (e.g., the circumferentially-oriented eyelets 224A may be in fewer than all of the proximal-facing apices 226 in a particular row). Various methods are usable to form the plurality of circumferentially-oriented eyelets 224A. For example, the plurality of circumferentially-oriented eyelets 224A are optionally formed using a transverse lasing process, a transverse drilling process, a casting process, combinations thereof and other technique as desired.

Figure 26B:
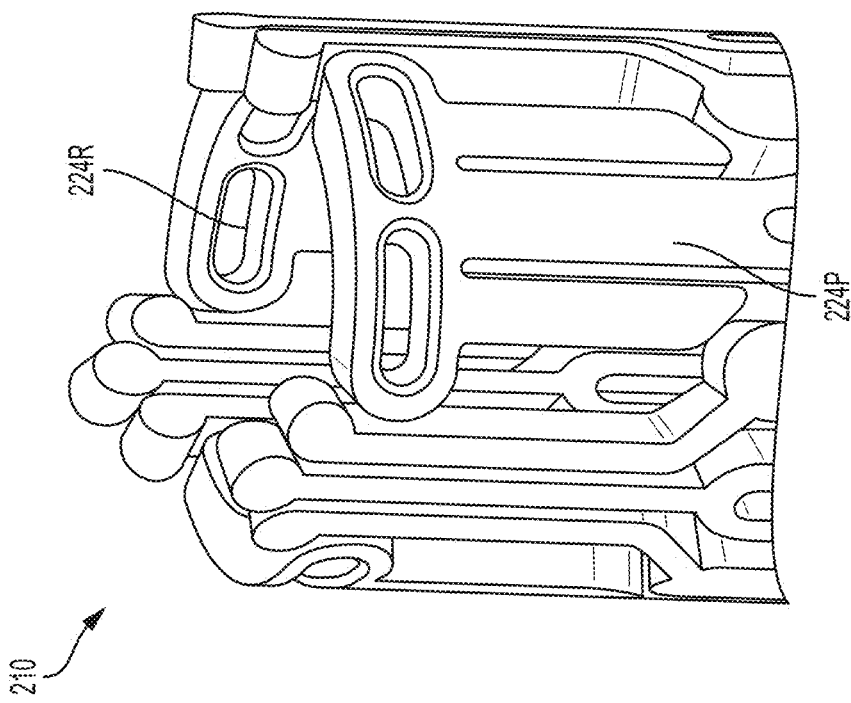
FIGS. 26A-31 show examples of features usable for securing constraints to a frame portion of an implantable device, according to some embodiments.
Figure 26A:
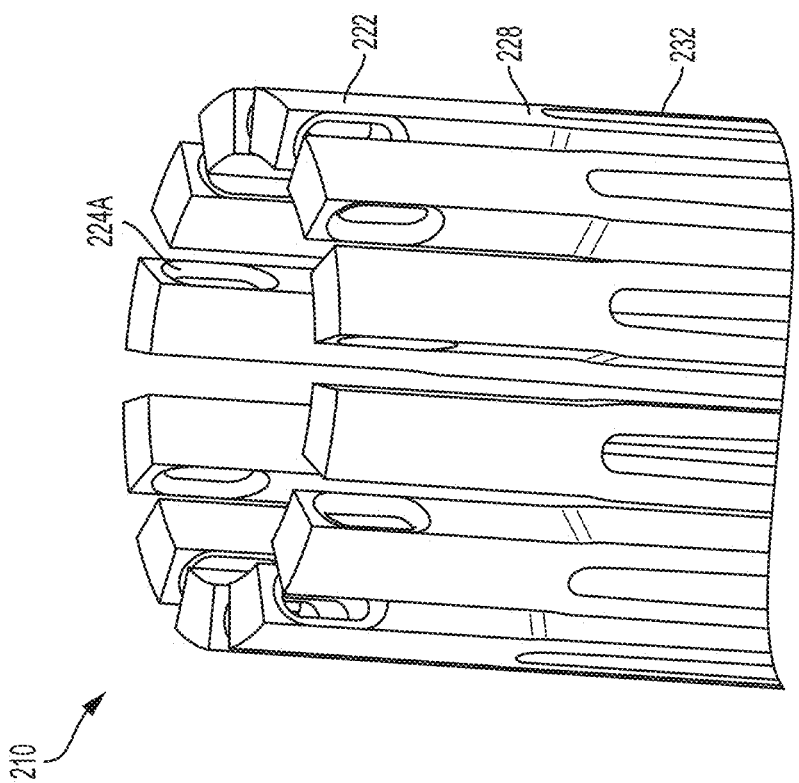

FIG. 26B shows a plurality of radially-oriented eyelets 224R formed at the proximal end 222 of the frame portion 210 (e.g., in a commissure attachment region 224P (e.g., commissure post) of the frame portion 210). As shown, the radially oriented-eyelets 224R have smoothed edges (e.g., via electro polishing). In some examples, one of the plurality of constraints 28 is able to be woven through the radially-oriented eyelets 224R to help provide guide the constraint 28 as it extends about the frame portion 210. The radially-oriented eyelets 224R are optionally formed via lasing, or other manufacturing option as desired.

Figure 26C:
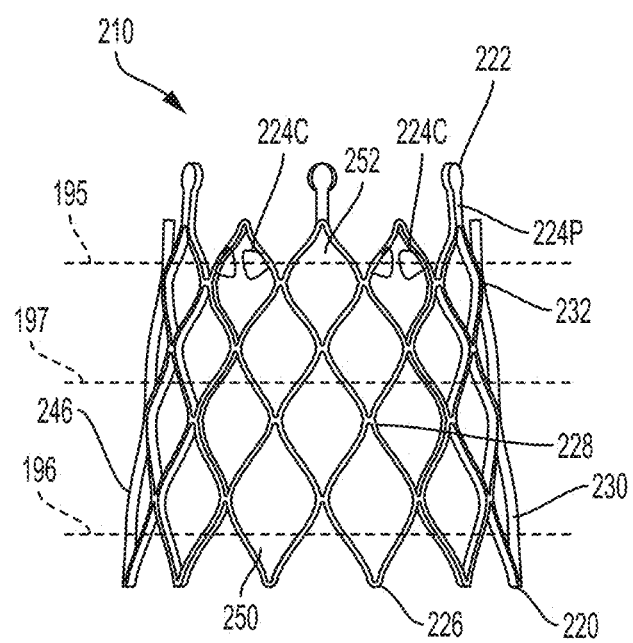
Figure 26E:
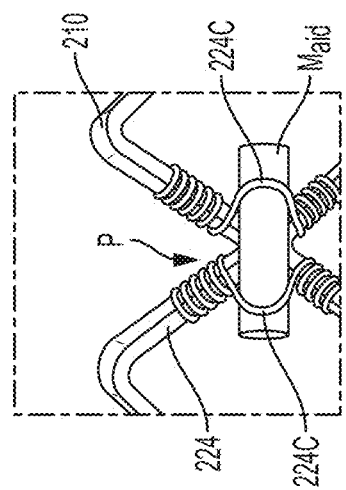
Figure 26D:
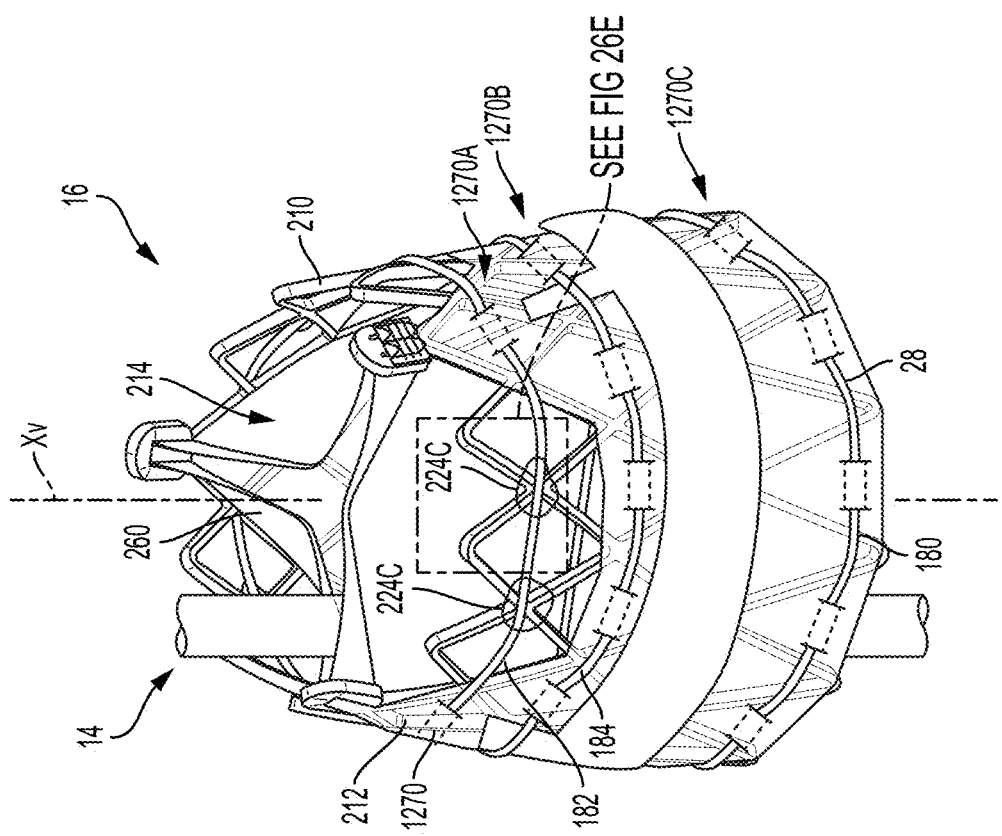

FIG. 26C shows a frame portion with a plurality of constraint retainers 224C (also described as constraint guides) secured to the frame portion 210. FIG. 26D shows the prosthetic valve 16 with the constraint retainers 224C and FIG. 26E is a close up view of the constraint retainers 224C as formed with a manufacturing aid Maid. As shown, the prosthetic valve 16 includes one or more constraint retainers 224C formed as a loop of material coupled to the frame portion 210. In some embodiments, the constraint retainers 224C are each formed by one or more loops of material, such as polymeric material (e.g., ePTFE fiber), metallic material (e.g., nitinol), or any other material that is biocompatible and suitable for implantation with the prosthetic valve 16. In some examples, the constraint retainers 224C are formed of filamentary material, such as a filament, strand, or a wire (e.g., polymeric or metallic). The constraint retainers 224C are optionally wound about the frame portion 210 to attach the constraint retainers 224C to the frame portion 210.

In some examples, one or more of the constraint retainers 224C are formed of a biocorridible or biodegradable material that biocorrodes or bioabsorbs over time following implantation. Like the afore-mentioned features, the constraint retainers 224C are optionally employed to help secure one or more of the plurality of constraints 28 in place and help prevent slipping off the proximal end the frame portion 210.

FIG. 26E illustrates two of the constraint retainers 224C which have been formed by wrapping filaments around the frame members 224 a plurality of times to secure the filaments to the frame members 224 and to form one or more loops suitable for receiving one of the constraints 28. As previously described, the filaments forming the constraint retainers 224C can be metallic (e.g., nitinol) polymeric (e.g., ePTFE) or any other biocompatible material. In some examples, the filaments are formed of biocompatible, biocorrodible/biodegradable material such that the filaments degrade and are absorbed or pass out of the body after a desired time frame. If desired, the loops of the constraint retainers 224C can also be bonded (e.g., in addition or as an alternative to the wrapping securement mechanism) to specific points the frame members 224 using a suitable adhesive or other bonding agent, for example.

Figure 26G:
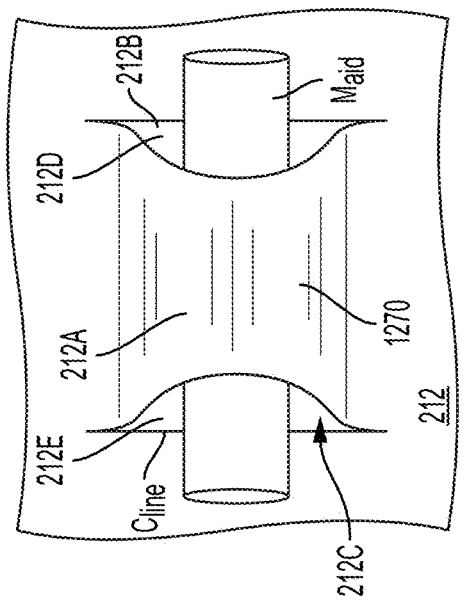
Figure 26F:
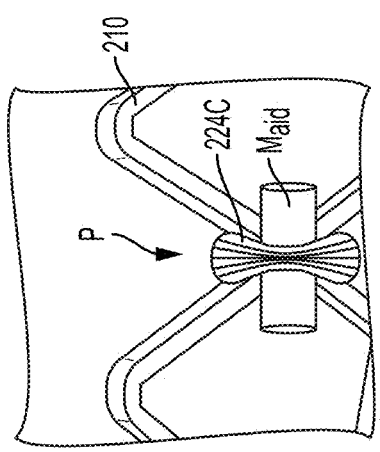

FIG. 26F illustrates a constraint retainer 224C formed by wrapping a filament around the frame portion 210 at an intersection location, or intersection point, such as intersection location P. The constraint retainer 224C is formed by wrapping a filament around the frame members 224 at the intersection P one or more times to secure the filament to the frame members 224 and to form one or more loops suitable for receiving one of the constraints 28. As previously described, the constraint retainer 224C can be metallic (e.g., nitinol) polymeric (e.g., ePTFE) or other material. In some examples, the constraint retainer 225C is formed of biocompatible, biocorrodible/biodegradable material such that the constraint retainer 224C degrades and is absorbed or passes out of the body after a desired time frame. If desired, the constraint retainer 224C can be wrapped and bonded to specific points on the frame members 224 (e.g., in addition or as an alternative to the wrapping securement mechanism) using a suitable adhesive or other bonding agent, for example.

In some examples, a method of forming the prosthetic valve 16 with the constraint retainers 224C includes the following steps:

Obtaining a manufacturing aid Maid for placement through each of the loops of the constraint retainer 224C, where the manufacturing aid Maid should have a desired diameter to achieve an appropriate level of interference of the constraint 28 with the constraint retainer 224C upon removal of the manufacturing aid Maid, should be able to withstand bonding temperatures for any bonding agent used with the filament forming the constraint retainer 224C, and should not bond to the material forming the constraint retainer 224C, or should otherwise be configured such that the manufacturing aid Maid is able to be effectively removed from the constraint retainer 224C (e.g., a potential manufacturing aid Maid may be a PEEK rod);

Wrapping a filament around the frame members 224 one or more times to secure the filament to the frame members 224 and to form the constraint retainer 224C over the manufacturing aid Maid;

Preparing the frame portion 210, filament, and manufacturing aid Maid for optional bonding (e.g., by heating in an oven to reflow the adhesive(s) and/or sinter winding(s); and Removing the manufacturing aid Maid from the constraint retainer 224C. In some examples, the manufacturing aid Maid may be loosened or freed from the constraint retainer 224C using a slender rod (or needle) to trace the outer diameters of the manufacturing aid Maid to break the manufacturing aid Maid free from the filament prior to pulling the manufacturing aid Maid out of the constraint retainer 224C (e.g., with a tweezers). Generally, the same process may be used to form any number of constraint retainers 224C as desired.

Although the constraint retainers 224C are shown at the position corresponding to the proximal constraint 180, the constraint retainers 224C can be positioned as desired on the frame portion 210, and may be used with any of the plurality of constraints 28 as desired.

FIGS. 25D and 25G illustrate constraint guiding, or constraint retention features for the prosthetic valve 16 that can be provided in addition to or as an alternative to the rows of apertures 270 and constraint retainers 224C, according to some examples. For example, as shown in FIG. 26D, the prosthetic valve 16 optionally includes a plurality of constraint guides 1270, which may operate similarly to the constraint retainers 224C to receive constraints 28 for delivery and deployment of the prosthetic valve 16. It should also be understood that any combination of constraint retention features is employed as desired and, as shown in FIG. 26D, the prosthetic valve 16 also optionally includes one or more constraint retainers 224C formed as loops of material coupled to the frame portion 210 (e.g., secured to one or more of the plurality of frame members 224) as previously described.

Like the constraint retainers 224C, the constraint guides 1270 help retain one or more of the constraints 28 passing around the prosthetic valve 16. The constraint guides 1270 can be described as tunnels, external bands, or belt loops, through which the constraints 28 are able to be slidably or otherwise received. As shown, the constraint guides 1270 are formed by bands or layers of material that define spaces, gaps, or tunnels between layers of material (e.g., between layers of the cover 212). The constraints 28 pass through these gaps and are retained between the layers of material. This type of arrangement can be contrasted to those in which constraint 28 is threaded in-and-out of the rows of apertures 270, from the interior to the exterior of the prosthetic valve 16. In different terms, as shown in FIG. 26D the constraint guides 1270 do not result in the constraint 28 passing behind the cover 212 into the interior of the prosthetic valve 16.

Generally, the approach implemented by the constraint guides 1270 is to embed, or retain one of the constraints 28 within portions of the cover 212, rather than having the constraint 28 simply wrapped around the periphery of the prosthetic valve 16 or laced through an interior and exterior path of the prosthetic valve 16 through the rows of aperture 270.

The constraint guides 1270 can provide a variety of desirable features, including one of more of the following: reduced perivalvular leakage due to elimination of biopsies (e.g., openings or apertures) through the cover 212 of prosthetic valve 16 (e.g., in contrast to some examples using the apertures 270); improved durability of the prosthetic valve 16 due to less perforations; improved deployment reliability (e.g., release and/or tensioning of the constraint 28) due to reduced friction between constraint 28 and the prosthetic valve 16; improved compatibility and reliability of the prosthetic valve 16 due to reduction of interference/interaction of vessel walls with the constraint 28; reduced likelihood of snagging/pinching the constraint 28 as the constraint 28 is not captured or otherwise trapped between frame members 224 of the frame portion 210 (e.g., as can happen when the constraint 1272 is threaded in-and-out of the apertures 270 and/or the frame portion 210); and improved durability of the constraint 28, due to less wear from the frame portion 210 engaging the constraint 28 (e.g., pinching the constraint 28) when the prosthetic valve 16 is compressed, or diametrically compacted. These are just a few examples of optional advantages according to various embodiments.

Generally, the constraint guides 1270 receive one or more constraints 1272 that pass into and out of the constraint guides 1270 in a circumferential path extending around the frame portion 210. The one or more constraints 28 are thus able to be used for retaining the frame portion 210, and thus the prosthetic valve 16, in a diametrically compacted, delivery configuration and then permitting the prosthetic valve 16 to be transitioned to a diametrically enlarged, deployed configuration upon releasing tension in the one or more constraints 1272 using an associated delivery system (such as those previously or subsequently described).

As shown in FIG. 26D, the prosthetic valve 16 includes a plurality of rows of the constraint guides 1270, such as a proximal row of constraint guides 1270A, one or more intermediate rows of constraint guides 1270B, and a distal row of constraint guides 1270C. Each of the rows of constraint guides 1270 is positioned as desired for a corresponding constraint 28 to form a loop at a desired level along the prosthetic valve 16. For example, the cover 212 optionally includes a plurality of separate constraint guides 1270 each spaced circumferentially apart from one another about the circumference of the frame portion 210 in a row, with one of the constraints 28 passing through each of the plurality of constraint guides 1270 forming a single, circumferentially-aligned row. Although, in some examples, each of a plurality of separate constraint guides 1270 in a row is circumferentially-aligned about the circumference of the frame portion 210, in other examples a row is not circumferentially-aligned, but instead is helically aligned, or defines another path about the circumference of the frame portion 210 and cover 212 as desired.

Generally, the proximal row of constraint guides 5270a slidably receive a proximal constraint 1272a that is passed through the proximal row of constraint guides 5270a and which can be tensioned to collapse, or radially compress, the prosthetic valve 16 onto a delivery catheter as previously described. Similarly, the intermediate constraint guides 5270b and the distal constraint guides 5270c each slidably receive an intermediate constraint 1272b and a distal constraint 1272c, respectively, that are each is passed through the constraint guides 5272 and which can be tensioned to collapse, or radially compress, the prosthetic valve 16. As shown, the proximal constraint 1272a is optionally passed through constraint retainers 224C associated with the frame portion 210, for example. For reference, a single row may include multiple constraint guide designs, such as designs consistent with constraint guide 1270, constraint retainer 224C, or apertures 270.

FIG. 26G is an enlarged view of a portion of the prosthetic valve 16 including one of the constraint guides 1270. As shown in FIG. 26G, a manufacturing aid Maid is inserted through the constraint guide 1270. Each of the constraint guides 1270 is optionally formed similarly to the constraint guide 1270 shown in FIG. 26G. As shown in FIG. 26G, the constraint guide 1270 includes an outer layer 212A of material and base layer 212B of material that combine to form a loop and define a tunnel 212C, or gap, extending between the outer layer 212A and the base layer 212B within a thickness of the cover 212. The tunnel 212C extends between a first opening 212D and a second opening 212E in the outer surface of the cover 212.

As described below, the outer layer 212A and the base layer 212B are optionally formed as layers of the cover 212, where some methods of forming the constraint guides 1270 include making cut lines Cline through the outer layer 212A on either side of the tunnel 212C. In other embodiments, the outer layer 212A is formed as a discrete flap, or piece of material that is subsequently secured to the cover 212 to define the tunnel 212C, as well as a portion of the outer surface of the cover 212.

FIG. 26D also illustrates one potential preferred position for the support portion of any of the examples herein with regard to a prosthetic valve according to any of the examples herein. In particular, the support portion (e.g., any of support portions 24, 524, 1024, as well as 3512, 4024, 5024, 6024 subsequently described) is shown positioned adjacent the frame portion 210 (next to a commissure post or other commissure attachment region 224P) between adjacent leaflets 260 of the leaflet construct 214. The location between adjacent leaflets 260 is optionally termed a "commissure line," location. As shown, the support portion is pinned, secured, or otherwise maintained by the delivery catheter at the commissure line adjacent to one of the commissure attachment regions 224P (e.g., a commissure post) by the delivery catheter due to the tension on the constraints (whether in the collapsed, delivery configuration or the expanded, deployed configuration).

With additional reference to FIG. 26D, the frame portion 210 generally defines a circumference extending along a transverse path around the central longitudinal axis Xv of the prosthetic valve 16. As previously referenced, the cover 212 is coupled to the frame portion 210 and includes the constraint guides 1270. In some examples, each constraint guide 1270 defines a tunnel 212C, such as that shown in FIG. 26D, that extends transversely to the central longitudinal axis Xv of the prosthetic valve 16 between the first opening 212D and second opening 212E in the outer surface of the cover 212.

Some methods of forming the prosthetic valve 16 with constraint retainers 224C include one or more of the following steps:

- Applying one or more layers of inner cover material to form the base layer 212B onto a mandrel, where the inner cover material includes an outwardly-facing adhesive;
- Positioning the frame portion 210 over the base layer 212B;
- Preparing one or more layers of outer cover material to form the outer layer 212A, where the outer cover material optionally includes an inwardly facing adhesive;
- Cutting the outer layer 212A along the cut lines Cline on either side of the tunnel 212C that will be formed at locations corresponding to each constraint guide 1270;
- Positioning the outer layer 212A over the frame portion 210, the base layer 212B and the outer layer 212A combining to form the cover 212, where the cut lines Cline, or holes through the outer layer 212A are positioned at the desired locations for the constraint guides 1270;
- Obtaining a manufacturing aid Maid for placement through each of the tunnels 212C (i.e., through the cut lines Cline on either side of the tunnels 212C), where the manufacturing aid Maid should have a desired diameter to achieve an appropriate level of interference of the constraint 28 with the constraint guide 1270 upon removal of the manufacturing aid Maid, may have a length corresponding to that of individual tunnels 212C or be longer, continuous element for placement through multiple tunnels 212C, should be able to withstand bonding temperatures of the base layer 212B and the outer layer 212A, and should not bond to the base layer 212B and/or outer layer 212A, or should otherwise be configured such that the manufacturing aid Maid is able to be effectively removed from the tunnel 212C (e.g., a potential manufacturing aid Maid may be a PEEK rod);
- Threading the manufacturing aid Maid through the tunnels 212C between the base layer 212B and the outer layer 212A;
- Preparing the frame portion 210, base layer 212B, outer layer 212A, and manufacturing aid Maid for bonding and bonding one or more of the foregoing (e.g., by overwrapping with a sacrificial compression layer and heating in an oven to reflow the adhesive(s) and/or sinter layer(s)); and
- Removing the manufacturing aid Maid from the tunnel 212C. In some examples, the manufacturing aid Maid may be loosened or freed from the tunnel 212C by using a slender rod (or needle) to trace the outer diameter of the manufacturing aid Maid to break the manufacturing aid Maid free from the base layer 212B and/or outer layer 212A prior to pulling the manufacturing aid Maid out of the tunnel 212C (e.g., with a tweezers). Generally, the same process may be used to form any number of the tunnels 212C as desired.

Although some examples have been provided, any of the foregoing constraint guide features may be used alone or combined into a single prosthetic valve design as desired.

Figure 28:
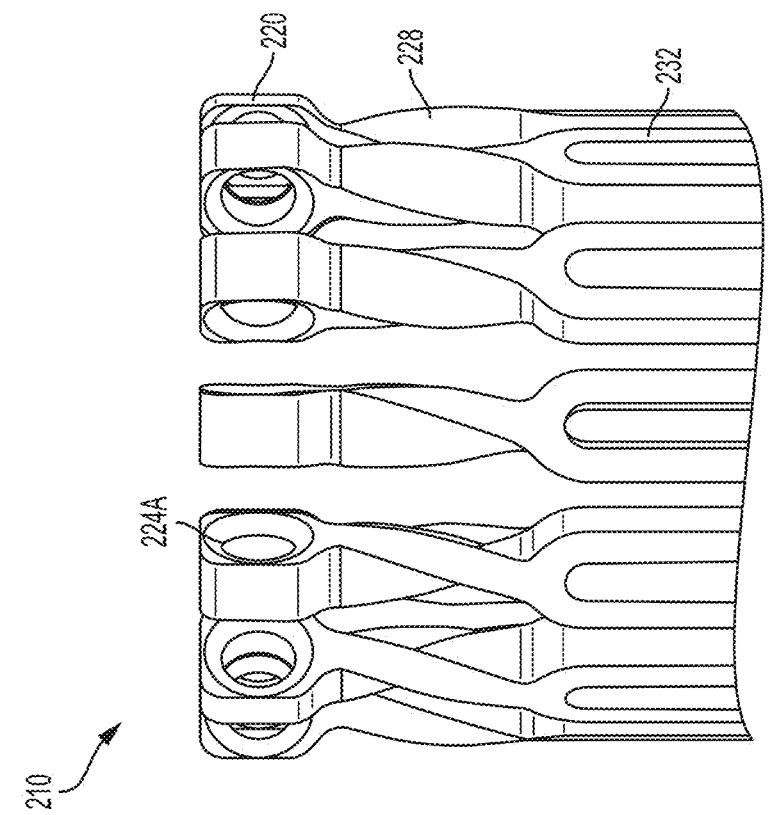
Figure 27:
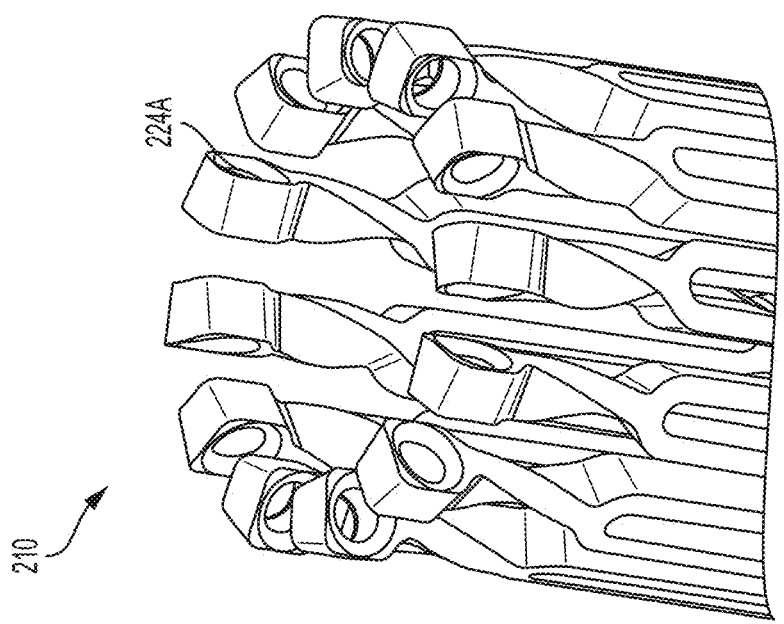
Figure 29:
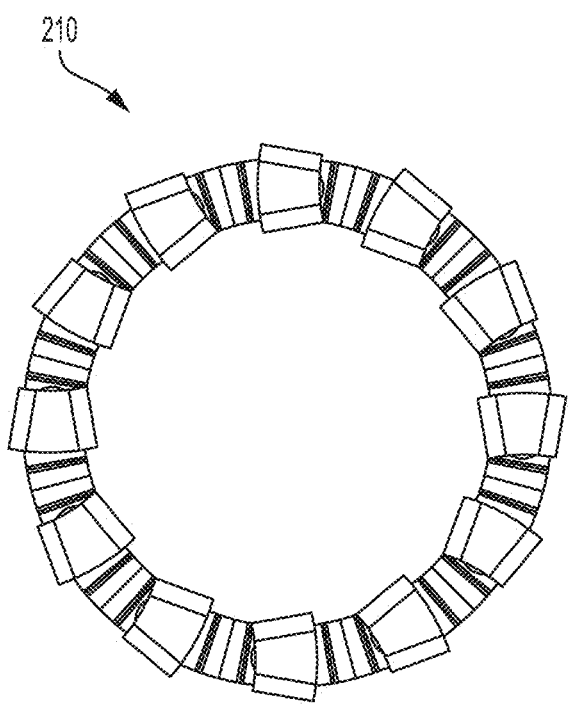
Figures 30, 31:
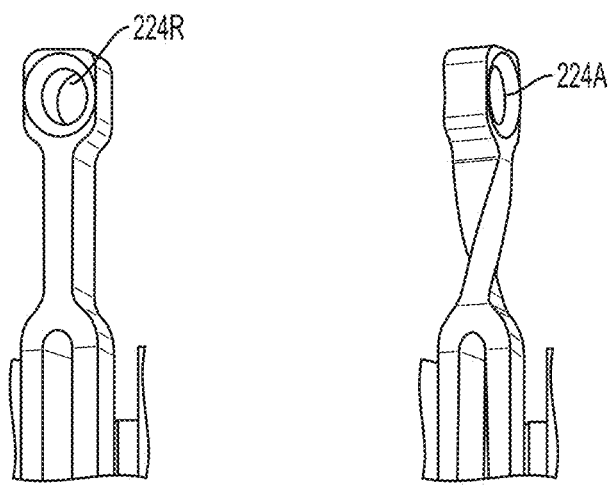

It should also be understood that various modifications to the features of the various frame portions usable for securing one of the plurality of constraints 28 to the frame portion are contemplated. For example FIGS. 26-30 are illustrative of additional features for securing one of the plurality of constraints 28 to the frame portion 210. As shown, radially-oriented eyelets can be formed and then transitioned into circumferentially-oriented eyelets. FIGS. 26-30 are illustrative of plurality of circumferentially-oriented eyelets 224A formed using such a technique. FIG. 27 is an isometric view of a proximal part of the frame portion 210, FIG. 28 is a front view of the proximal part of the frame portion 210, FIG. 29 is an end view of the proximal part of the frame portion 210, and FIG. 30 and FIG. 31 illustrate a manner of formation of one of the plurality of circumferentially-oriented eyelets 224A according to FIGS. 27-31. For example, as shown, the plurality of circumferentially-oriented eyelets 224A can optionally be formed by first forming a radially-formed eyelet 224R in a radial direction (FIG. 30) and then twisting the frame portion 210 (e.g., the distal-facing apices 226) to re-orient the radially-formed eyelet 224R circumferentially to define one of the plurality of circumferentially-oriented eyelets 224A (FIG. 31). This, twisted form may be heat set, set by cold working, or set by any of a variety of methods as desired depending upon application and material used.

Various advantages may be realized by securing one or more of the plurality of constraints 28 (or the constraint 1028) using circumferentially-oriented eyelets 224A, such as the plurality of circumferentially-oriented eyelets 224A of any of the foregoing examples. As one potential advantage, tension forces may be reduced via a reduction in friction forces that might otherwise be exhibited by features for securing constraints to a prosthetic valve (e.g., by reducing the amount of surface area contacted by a constraint). Moreover, surface profile may be reduced by having the constraint pass "within" the body of the frame 210 and reliability in deployment and compaction may be increased.

Figure 32:
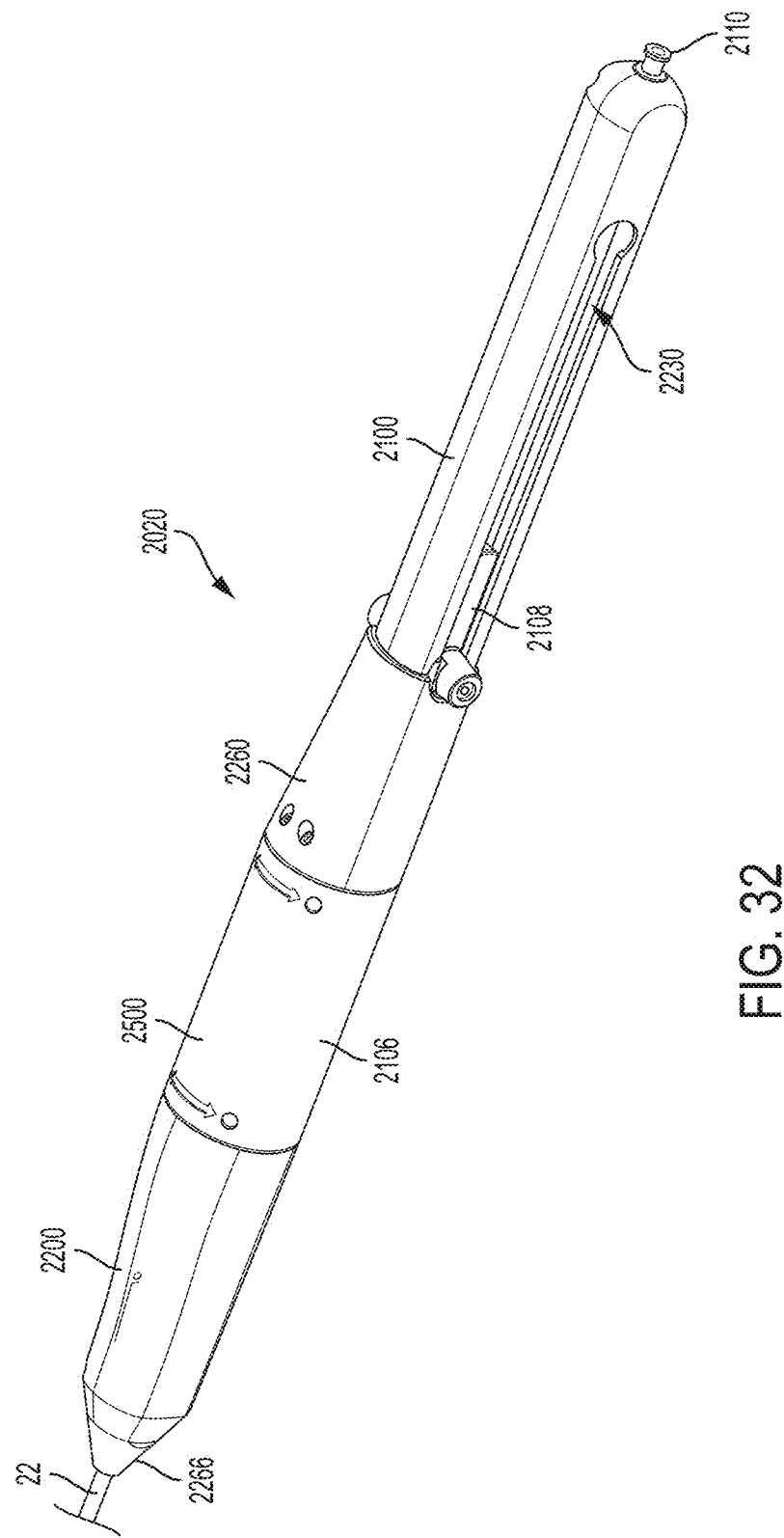
FIG. 32 is an isometric view of an actuation portion of a delivery catheter in an assembled state, according to some embodiments.
Figure 33:
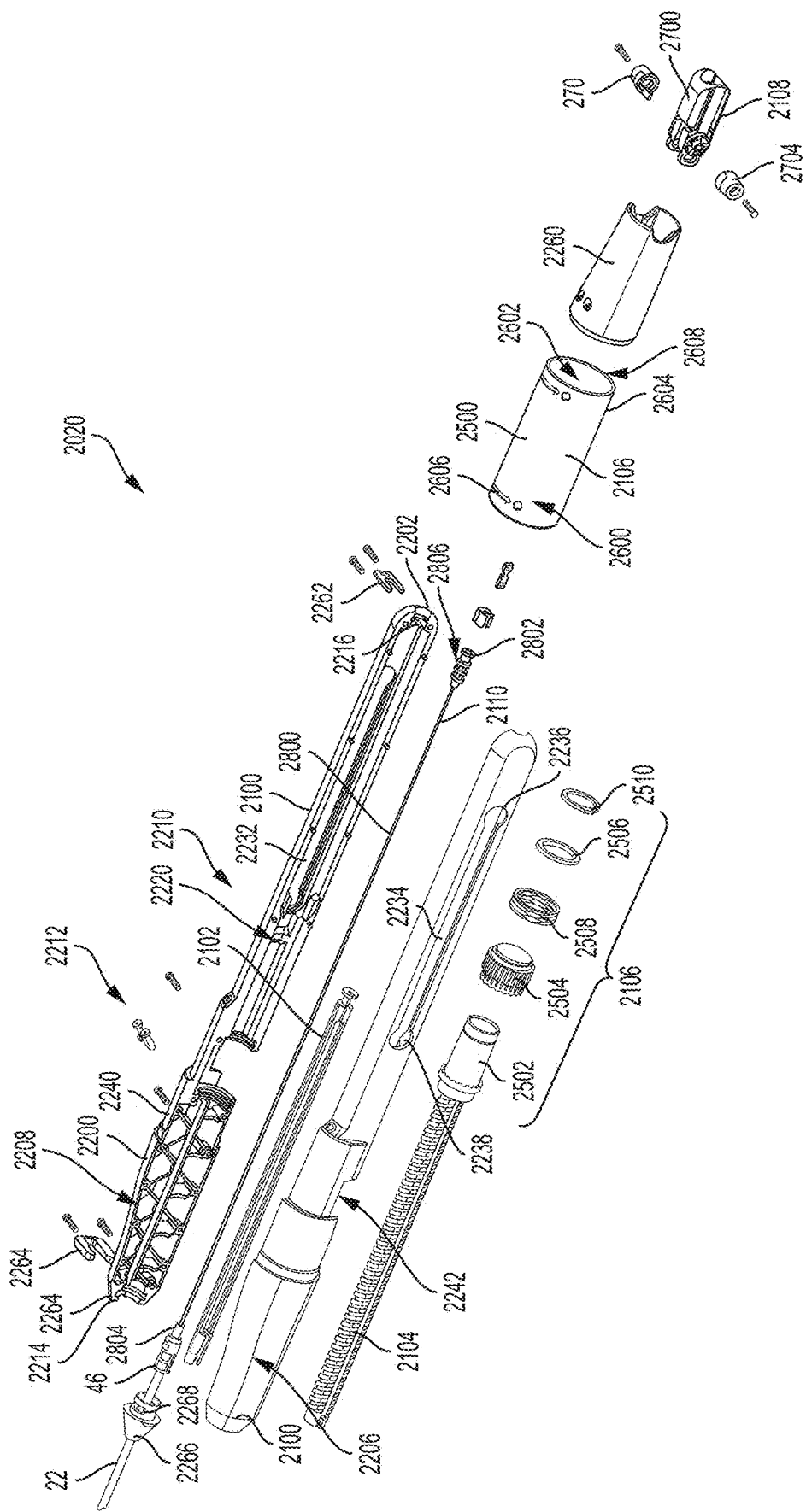
FIG. 33 is an isometric view of the actuation portion of FIG. 32 in a disassembled state, according to some embodiments.

As indicated above, the delivery catheter 14 and delivery catheter 1014 can be used with a variety of actuation portions, or actuators. FIGS. 31-42 are illustrative of possible features of another actuation portion 2020 that may be employed for the delivery catheter 14 or the delivery catheter 1014 as desired. FIG. 32 is an isometric view of the actuation portion 2020 in an assembled state and FIG. 33 is an isometric view of the actuation portion 2020 in a disassembled state, often described as an exploded view. In alternate terms, the actuation portion 2020 can also be described as a deployment handle or a deployment handle assembly, according to various embodiments.

As shown in FIGS. 31 and 32, the actuation portion 2020 includes a housing assembly 2100, a rack assembly 2102 (FIG. 33), a drive assembly 2104, an actuation assembly 2106, a release assembly 2108, and a catheter subassembly 2110. In general terms, the actuation portion 2020 is configured to permit actuation (tensioning and de-tensioning or releasing) of the plurality of constraints 28 (FIG. 2), release and retraction of the plurality of constraints 28 via retraction of the stake member 30 (FIG. 2) to release the plurality of constraints 28 and retraction of the plurality of constraints 28 from the prosthetic valve 16 (FIG. 14A), and can also optionally include a full release of the body portion 22 of the delivery catheter 14 from the actuation portion 2020. In various examples, the actuation portion 2020 is configured to actuate (tension or de-tension the plurality of constraints 28 concurrently, all at one time, although separate and/or sequential actuation (e.g., as described in association with the actuation portion 20) is also contemplated.

As shown in FIG. 33, the housing assembly 2100 includes a body portion 2200 that extends from a proximal end 2202 to a distal end 2204, defines an outer surface 2206, an inner surface 2208, a proximal section 2210 near the proximal end 2202, a distal section 2212 near the distal end 2204, a distal clip slot 2214 near the distal end 2204, and a proximal clip slot 2216 near the proximal end 2202, and forms an inner cavity 2220 for housing various components of the actuation portion 2020. As shown, the body portion 2200 is optionally of a clamshell design for ease of manufacture and assembly. For example, the body portion 2200 can include two halves or longitudinal sections that are able to be assembled together (e.g., using fasteners such as screws), although a variety of configurations are contemplated.

As shown, the proximal section 2210 defines a release assembly track 2230 (FIG. 32) formed by a first elongate slot 2232 and a second elongate slot 2234 formed opposite the first elongate slot 2232 and each extending longitudinally along the proximal section 2210. Each of the first elongate slot 2232 and the second elongate slot 2234 has a proximal enlarged end 2236 and a distal enlarged end 2238. In turn, the distal section 2212 defines an actuation assembly support 2240 on the outer surface 2206 and an actuation assembly window 2242 in the form of an opening through the body portion 2200 (e.g., on a lower side of the body portion 2200).

As shown in FIG. 33, the housing assembly 2100 also optionally includes a knob support 2260 that is coaxially received over the distal section 2212 and secured to the body portion 2200 (e.g., using fasteners such as screws), a proximal lock clip 2262 insertable into the body portion 2200 at the proximal end 2202 of the body portion 2200, a distal lock clip 2264 insertable into the body portion 2200 at distal end 2204 of the body portion 2200, and a nose cone 2266 having a clip slot 2268 and which is receivable in the distal end 2204 of the body portion 2200.

Figure 34:
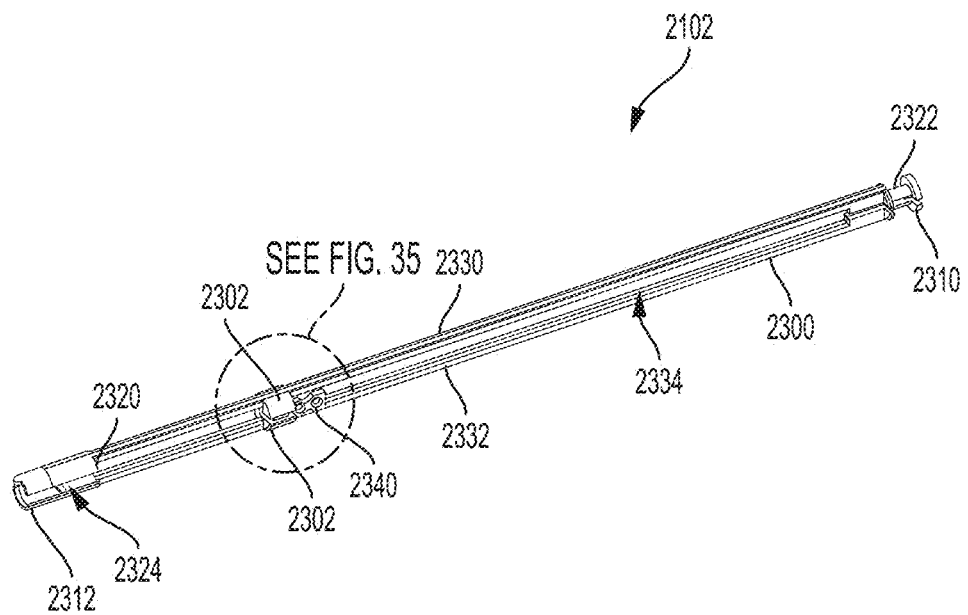
FIG. 34 is an isometric view of an assembly of an actuation portion and FIG. 35 is an enlarged view of the circled portion of FIG. 34, according to some embodiments.
Figure 35:
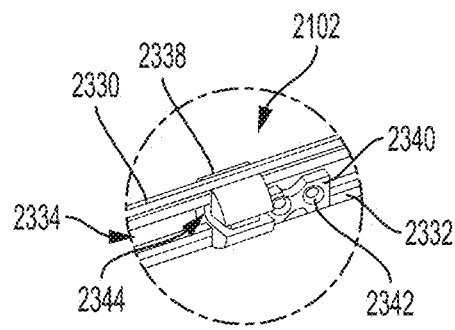

FIG. 34 is an isometric view of the rack assembly 2102 and FIG. 35 is an enlarged view of the circled portion of FIG. 34, according to some embodiments. As shown, the rack assembly 2102 includes a slide rail 2300 and a slider 2302. As shown, the slide rail 2300 extends from a proximal end 2310 to a distal end 2312, forms a stop 2320 at the distal end 2312, and a retraction feature 2322 at the proximal end 2310. The distal end 2312 also optionally includes a slot 2324, also described as a pocket, into which the proximal end 30a of the stake member 30 (FIG. 2) can be secured. The slot 2324 can also be configured to receive and permit the plurality of constraints 28 (FIG. 2) to pass through the slot 2324 as desired. The slide rail 2300 has an upper track 2330 and a lower track 2332 extending between the stop 2320 and the retraction feature 2322, the upper track 2330 and the lower track 2332 being separated by a gap 2334.

As shown, the slider 2302 is slidably received between the upper track 2330 and the lower track 2332 within the gap 2334 such that the slider 2302 can move proximally and distally within the gap 2334. The slider 2302 includes a carrier 2338 and a clip 2340 including a plurality of apertures 2342 configured to receive and secure the plurality of constraints 28. The slider 2302, and in particular the carrier 2338, also defines a distal engagement face 2344 for moving the slider 2302 proximally and distally within the gap 2334. As shown, the clip 2340 is removably secured to the carrier 2338 (e.g., using a slip fit, friction fit, interference fit, or other attachment mechanism).

Figure 36:
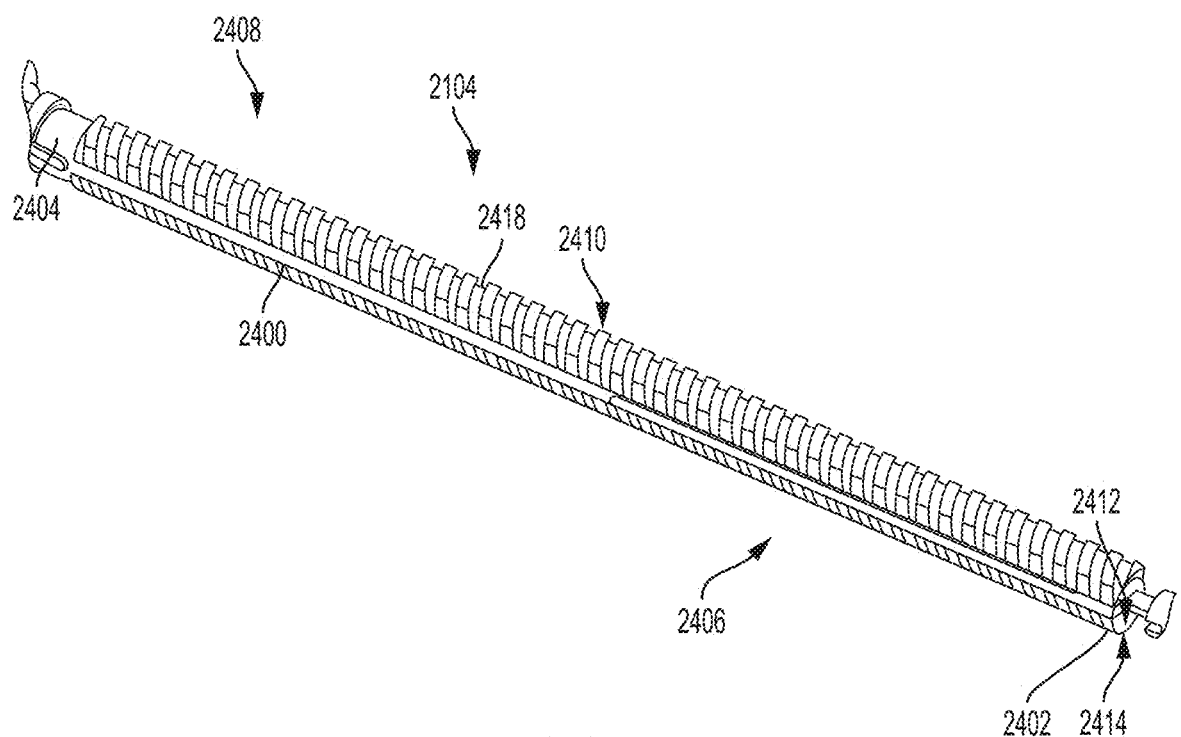
FIG. 36 is an isometric view of a drive assembly of an actuation portion, according to some embodiments.

FIG. 36 is an isometric view of the drive assembly 2104, according to some embodiments. In some embodiments, the drive assembly 2104 includes a drive member 2400 extending from a proximal end 2402 to a distal end 2404, defining a proximal section 2406, a distal section 2408, an outer surface 2410, an inner surface 2412, and an inner lumen 2414 extending from the proximal end 2402 to the distal end 2404. As shown, the proximal section 2406 is slotted longitudinally to define a slot 2416. The outer surface 2410 is threaded, or includes external threads 2418 between the proximal end 2402 and the distal end 2404. In some embodiments, the inner lumen 2414 is configured to receive the body portion 22 of the delivery catheter 14 such that the body portion 22 is passable through the drive member 2400. The inner lumen 2414 also optionally defines a first diameter through the proximal section 2406 and at a location 2430 along the distal section 2408, the distal section 2408 defines a reduced diameter, or an engagement feature 2432 (FIG. 38).

As shown in FIG. 33, in some embodiments, the actuation assembly 2106 includes a deployment knob 2500, a nut portion 2502, a gear portion 2504, a spring keeper 2506, a biasing member 2508, and a retainer 2510.

Figure 38A:
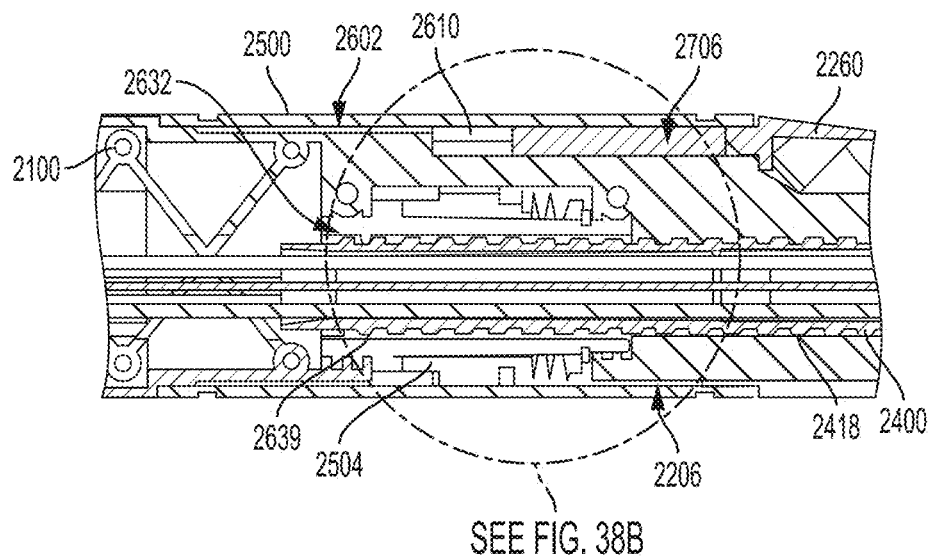
FIGS. 38A and 38B are longitudinal sections of a portion of a delivery catheter, according to some embodiments.
Figure 38B:
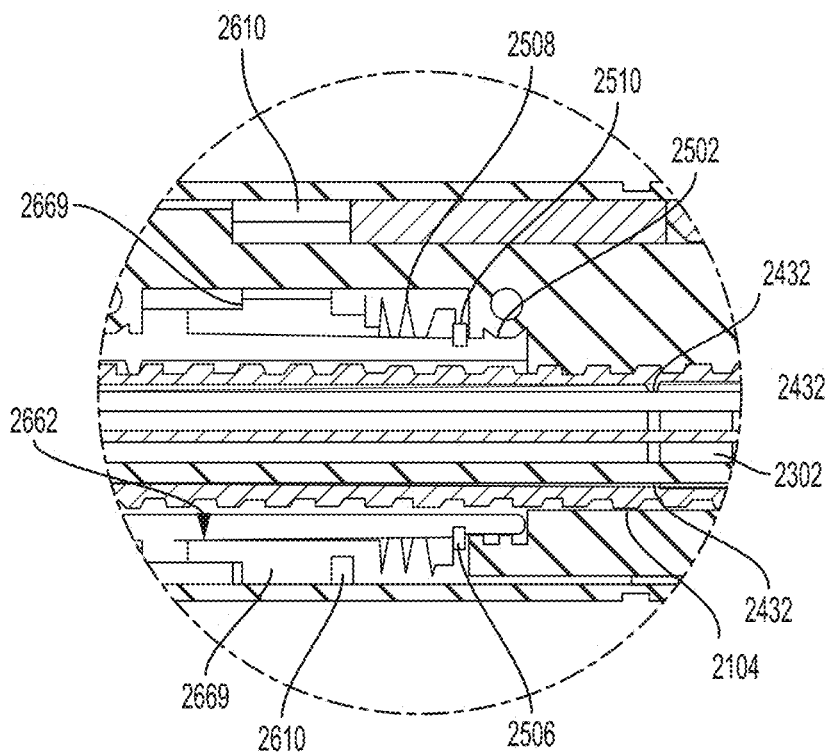
Figure 38C:
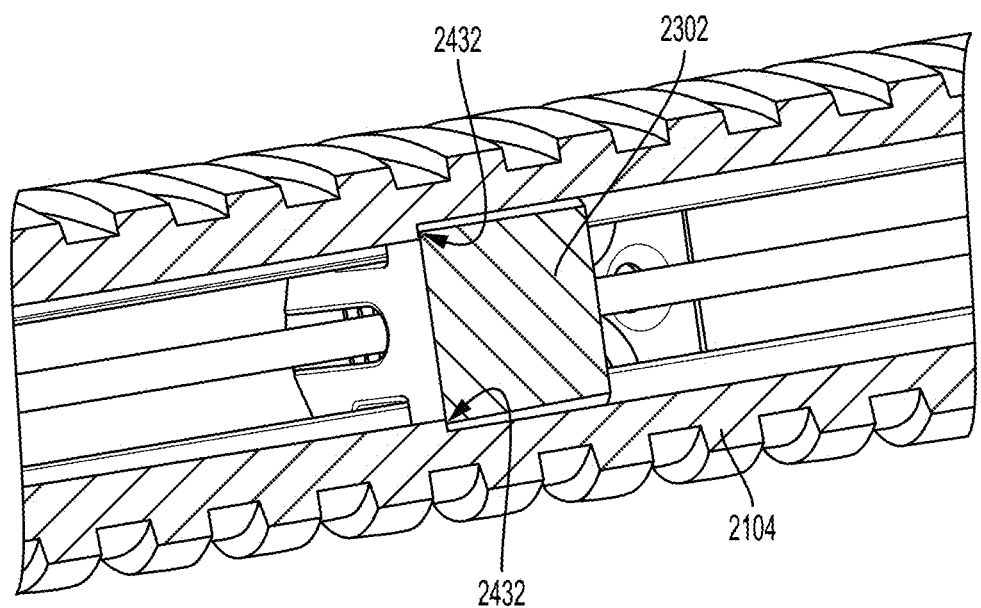
FIG. 38C is a partial longitudinal section of the portion of the delivery catheter of FIGS. 38A and 38B, with additional components removed to show an interaction between a slider and drive assembly of the delivery catheter, according to some embodiments.

As shown in FIG. 33, the deployment knob 2500 is optionally cylindrical and has an outer surface 2600, an inner surface 2602 (FIG. 38), a proximal end 2604, a distal end 2606, an inner lumen 2608 (FIG. 38) extending from the proximal end 2604 to the distal end 2606, and a plurality of engagement features 2610 which can be seen in FIG. 38 (e.g., gear teeth), extending from the inner surface 2602 into the inner lumen 2608 about a circumference of the inner lumen 2608.

Figure 37:
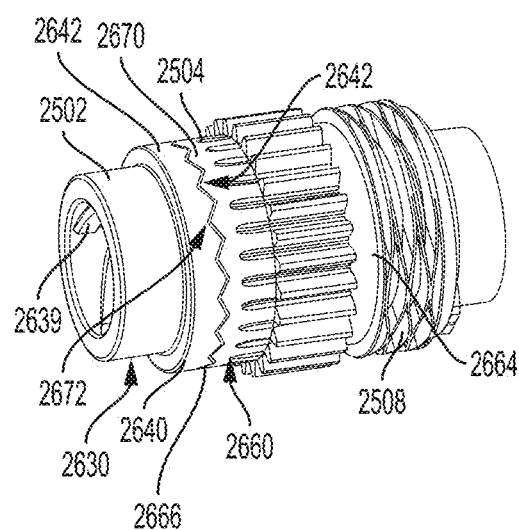
FIG. 37 is an isometric view of a nut portion and a gear portion of an actuation assembly of a delivery catheter, according to some embodiments.

In FIG. 33, the nut portion 2502 is shown threaded onto the drive member 2400. FIG. 37 shows an isometric view of the nut portion 2502 and the gear portion 2504 in an assembled state with the drive member 2400 removed from the nut portion 2502. As shown in FIG. 37, the nut portion 2502 has an outer surface 2630, an inner surface 2632 (FIG. 38), a proximal end 2634, a distal end 2636, an inner lumen 2638 (FIG. 38) extending from the proximal end 2634 to the distal end 2636, and a plurality of internal threads 2639 extending from the inner surface 2632 into the inner lumen 2638, and a ratchet shoulder 2640 defining a ratchet face 2642.

As shown in FIG. 33, and as further described, the gear portion 2504 configured to be rotatably received over the nut portion 2502. As shown in FIG. 37, the gear portion 2504 has an outer surface 2660, an inner surface 2662 (FIG. 38), a proximal end 2664, a distal end 2666, an inner lumen 2668 (FIG. 38) extending from the proximal end 2664 to the distal end 2666, and a plurality of engagement features 2669 (e.g., gear teeth) extending from the outer surface 2660, and a ratchet shoulder 2670 defining a ratchet face 2672 (FIG. 33) configured to mate with, or matingly engage with the ratchet face 2642 of the nut portion 2502.

In some embodiments, the biasing member 2508 is optionally one or more springs (e.g., one or more wave springs) or other biasing means as desired. The spring keeper 2506 is optionally one or more washers and the retainer 2510 is optionally one or more spring clips, although a variety of structures may be employed.

FIG. 38 is a longitudinal section of the actuation portion 2020 showing the actuation assembly 2106 in more detail. As shown, the actuation assembly 2106 is maintained by the housing assembly 2100 with the deployment knob 2500 rotatably received over the outer surface 2206 and secured against longitudinal translation. As shown, the knob support 2260 is placed at the proximal end 2202 of the body portion 2200 to help secure the deployment knob 2500 against longitudinal translation, and provides a gap 2706 between the outer surface 2206 of the body portion 2200 and the inner surface 2602 of the deployment knob 2500 so that the plurality of engagement features 2610 have room to rotate about part of the outer surface 2006 of the body portion 2200. As shown, the deployment knob 2500 is axially offset from the nut portion 2502 and the gear portion 2504. The plurality of engagement features 2610 of the deployment knob 2500 are exposed to the plurality of engagement features 2669 of the nut portion 2502 through the actuation assembly window 2242 (FIG. 33), which is formed as an opening through the body portion 2200 on the lower side of the body portion 2200. Thus, rotation of the deployment knob 2500 causes the engagement features 2610 to mesh with the engagement features 2669 resulting in positive or negative angular rotation of the gear portion 2504.

As shown in FIG. 38, the gear portion 2504 and the nut portion 2502 are rotatably received by the housing assembly 2100 with the nut portion 2502 secured against longitudinal translation by the housing assembly 2100. The gear portion 2504 is slidably and rotatably received over the nut portion 2502 and is permitted a limited amount of longitudinal travel by the housing assembly 2100. The gear portion 2504 is secured to the body portion 2200 of the housing assembly 2100 with the spring keeper 2506 and the retainer 2510 holding the biasing member 2508 against the gear portion 2504 to bias the gear portion 2504 distally. In this manner, the gear portion 2504 can be displaced a limited amount in the proximal direction once the biasing force (e.g., spring constant) of the biasing member 2508 is overcome. So biased, the ratchet face 2672 engages with the ratchet face 2642 of the nut portion 2502 (FIG. 37) so that rotation the gear portion 2504 results in rotation of the nut portion 2502 until a torsional limit is exceeded such that the biasing force is overcome, and the ratchet face 2672 and the ratchet face 2642 slip, or ratchet over one another. In this manner, the actuation assembly 2106 defines a clutch, and more specifically a ratchet or slip clutch, although other clutch mechanisms (e.g., magnetic) are also contemplated and are suitable for use.

According to the foregoing description, rotation of the deployment knob 2500 results in positive or negative angular rotation of the nut portion 2502 with a clutch mechanism defined between the deployment knob 2500 and the nut portion 2502 once sufficient resistance to rotation of the nut portion 2502 is encountered. As will be subsequently described, rotation of the nut portion 2502 (and thus rotation of the deployment knob 2500) is used to drive the drive assembly 2104, and more specifically to longitudinally translate the drive member 2400 in proximal and distal directions within the housing assembly 2100.

Figure 39:
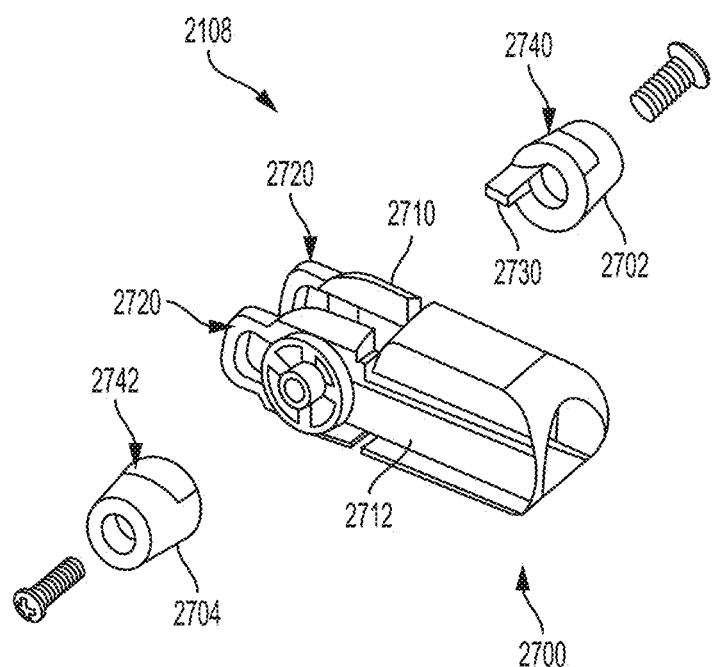
FIG. 39 is an isometric view of a release assembly of a delivery catheter, according to some embodiments.

FIG. 39 is an isometric view of the release assembly 2108, according to some embodiments. As shown in FIG. 39, in some embodiments, the release assembly 2108 includes a lock flexure 2700, a first button 2702, and a second button 2704. In some embodiments, the lock flexure 2700 includes a first flex arm 2710 and a second flex arm 2712. Each of the first flex arm 2710 and the second flex arm 2712 includes a grasping portion 2720 configured to engage and grasp the retraction feature 2322 at the proximal end 2310 of the slide rail 2300 (FIG. 34) upon inward flexing of the first flex arm 2710 and the second flex arm 2712. The first button 2702 and the second button 2704 are secured to the first flex arm 2710 and the second flex arm 2712 and such that the first button 2702 and the second button 2704 are able to be depressed to inwardly flex the first flex arm 2710 and the second flex arm 2712. In some examples, the release assembly 2108 includes a first stop feature 2730 formed on the first button 2702 and a similar, second stop feature (not shown) formed on the second button 2704. Each of the first stop feature 2730 and the second stop feature is optionally configured to help prevent inadvertent longitudinal retraction of the slide rail 2300 (FIG. 34) in the proximal direction. The release assembly 2108 also optionally includes a first locking feature 2740 (e.g., a channel) and a second locking feature 2742 (e.g., a channel) formed by the first button 2702 and the second button 2704 such that the release assembly 2108 is secured longitudinally to the housing assembly 2100 until the first button 2702 and the second button 2704 are depressed.

A shown in FIG. 33, in some embodiments, the catheter subassembly 2110 is coupled to the body portion 22 (FIG. 2) of the delivery catheter 14 (FIG. 2). For example, the catheter subassembly 2110 optionally includes a tube extension 2800 (e.g., for receiving a guidewire that can pass through the actuation portion 2020 to the body portion 22 of the delivery catheter 14), a proximal coupling 2802 and a distal coupling 2804. The distal coupling 2804 is optionally secured to the connector hub 46 of the body portion 22 and the proximal coupling 2802 is optionally secured to a portion of the housing assembly 2100, as described in further detail below. In some examples, the proximal coupling 2802 includes a clip slot 2806 Generally, the plurality of constraints 28 and the stake member 30 (FIG. 2) are permitted to bypass the catheter subassembly 2110 to be secured to the rack assembly 2102, as described in further detail below.

Some methods of assembling the actuation portion 2020 include assembling the catheter subassembly 2110 to the body portion 22 of the delivery catheter 14 by securing the distal coupling 2804 to the connector hub 46 of the body portion 22. The nose cone 2266 is received over the body portion 22 (e.g., coaxially received over the body portion 22) of the delivery catheter 14 such that the connector hub 46 and/or distal coupling 2804 are engaged with (e.g., received within) and abutted against the nose cone 2266. The tube extension 2800 of the catheter subassembly 2110 is received within the slide rail 2300 and the slider 2302 (FIG. 34) of the rack assembly 2102 (e.g., coaxially received within the slide rail 2300 and the slider 2302) such that the slide rail 2300 and the slider 2302 are slidable longitudinally over the tube extension 2800 (e.g., being slidable along the tube extension 2800 between the proximal coupling 2802 and the distal coupling 2804).

The drive assembly 2104, and in particular the drive member 2400 is slidably received over the rack assembly 2102 (e.g., coaxially received over the rack assembly 2102). FIG. 38 shows a portion of this interaction between the drive assembly 2104 and the rack assembly 2102, wherein the drive member 2400 is slidable over the slide rail 2300 and along the slide rail 2300 until the distal engagement face 2344 of the slider 2302 is proximally engaged by the engagement feature 2432 formed inside of the drive member 2400. Once the drive member 2400 is moved proximally sufficiently such that the engagement feature 2432 engages the distal engagement face 2344 (FIG. 34) of the slider 2302, then the slider 2302 is moved proximally, or is longitudinally translated in a proximal direction, within the slide rail 2300 as the drive member 2400 slides over the slide rail 2300. This interaction will be described in greater detail with respect to FIGS. 40-43, which are illustrative of operation of the actuation portion 2020, according to some examples.

As indicated by FIG. 38, the nut portion 2502 of the actuation assembly 2106 is threaded onto the drive member 2400 with the internal threads 2639 engaged with the external threads 2418. As previously described, the gear portion 2504 is slidably and rotatably received over the nut portion 2502 and engaged in clutch arrangement such that rotation of the gear portion 2504 results in rotation of the nut portion 2502 up until a torsional limit is reached at which point the gear portion 2504 is allowed to slip against the nut portion 2502. Although a clutch arrangement is defined by the nut portion 2502 and the gear portion 2504 according to various examples, it should also be understood the two can simply be rotationally fixed together (e.g., being formed integrally with one another or simply by being separate, but fixedly connected parts).

As previously described, the actuation assembly 2106 is maintained by the housing assembly 2100 with the deployment knob 2500 rotatably received over the outer surface 2206 of the body portion 2200 and secured against longitudinal translation. The knob support 2260 is located at the proximal end 2604 of the deployment knob 2500 to help secure the deployment knob 2500 against longitudinal translation, and also to provide a gap 2706 between the outer surface 2206 of the body portion 2200 and the inner surface 2602 of the deployment knob 2500 in which the engagement features 2610 have room to rotate. The plurality of engagement features 2610 of the deployment knob 2500 are exposed to the plurality of engagement features 2669 of the nut portion 2502 through the actuation assembly window 2242 such that rotation of the deployment knob 2500 causes the engagement features 2610 to mesh with the engagement features 2669 resulting in positive or negative angular rotation of the gear portion 2504, which translates to longitudinal translation (proximal or distal, depending upon the direction of rotation of the deployment knob 2500) of the drive member 2400.

As understood with reference to FIG. 33, the lock flexure 2700 is configured to be slidably received in the release assembly track 2230 (FIG. 32) such that the first button 2702 and the second button 2704 are received in the distal enlarged ends 2238 of each of the first elongate slot 2232 and the second elongate slot 2234. The distal enlarged ends 2238 engage with the first button 2702 and the second button 2704 to "lock" the release assembly 2108 to the housing assembly 2100. When the first button 2702 and the second button 2704 are depressed to flex the first flex arm 2710 and the second flex arm 2712 (FIG. 39) inwardly, the first locking feature 2740 and the second locking feature 2742 (FIG. 39) move inwardly and accept the edges of the first elongate slot 2232 and the second elongate slot 2234. This "unlocks" the release assembly 2108 and permits the first button 2702 and the second button 2704, and thus the lock flexure 2700 to be slide proximally out of the distal enlarged ends 2238 of each of the first elongate slot 2232 and the second elongate slot 2234 and proximally along the release assembly track 2230.

Figure 40:
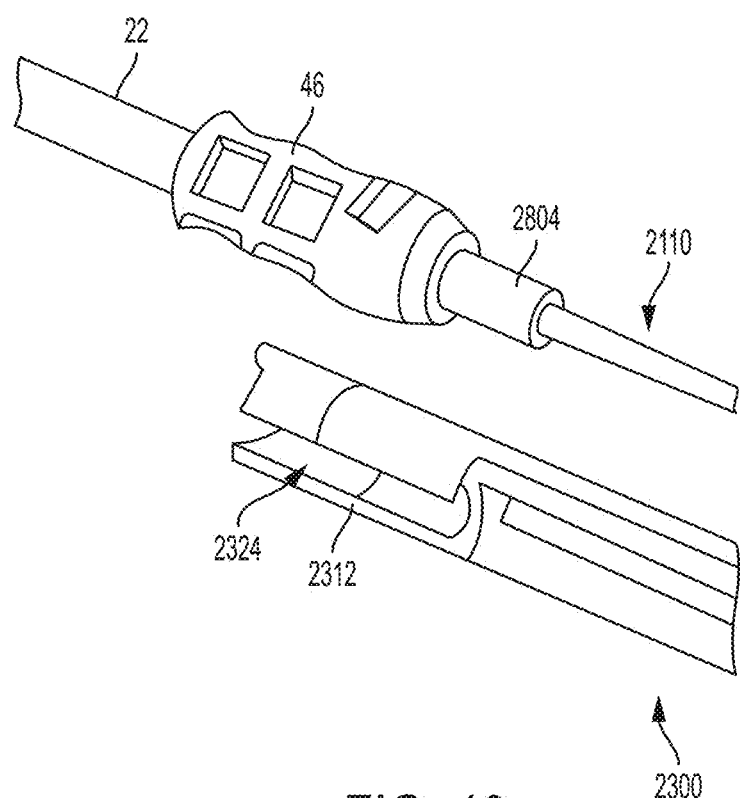
FIG. 40 is an enlarged view of a distal coupling of a catheter subassembly secured to a connector hub of a body portion of a delivery catheter juxtaposed with a distal end of a slide rail, according to some embodiments.

FIG. 40 is an enlarged view of the distal coupling 2804 of the catheter subassembly 2110 secured to the connector hub 46 of the body portion 22 of the delivery catheter 14 (FIG. 2) juxtaposed with the distal end 2312 of the slide rail 2300. The distal end 2312 of the slide rail 2300 receives abuts against the distal coupling 2804 and/or connector hub 46 to stop distal movement of the slide rail 2300 (unless purposefully released to be removed from the housing assembly 2100, as described below). The distal end 2312 of the slide rail 2300, and in particular the slot 2324 receives and secures the proximal end 30a of the stake member 30 to the slide rail 2300. Though not shown in FIG. 40, the slot 2324 also permits the plurality of constraints 28 to pass from the connector hub 46 of the body portion 22 through the slot 2324 to be attached to the clip 2340 of the slider 2302, and in particular to be secured in the plurality of apertures 2342 of the clip 2340 (FIG. 34).

Figure 41:
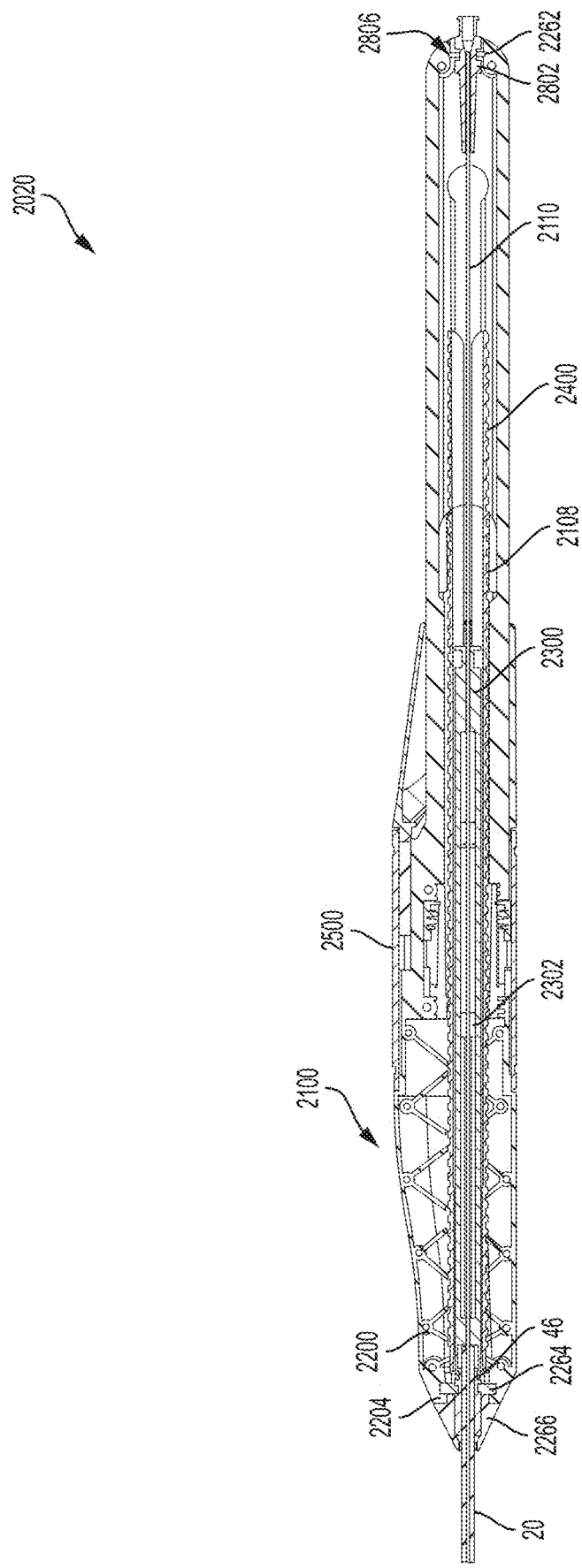
FIGS. 41-44 are longitudinal cross sections of an actuation portion of a delivery catheter at various stages of operation, according to some embodiments.
Figure 42:
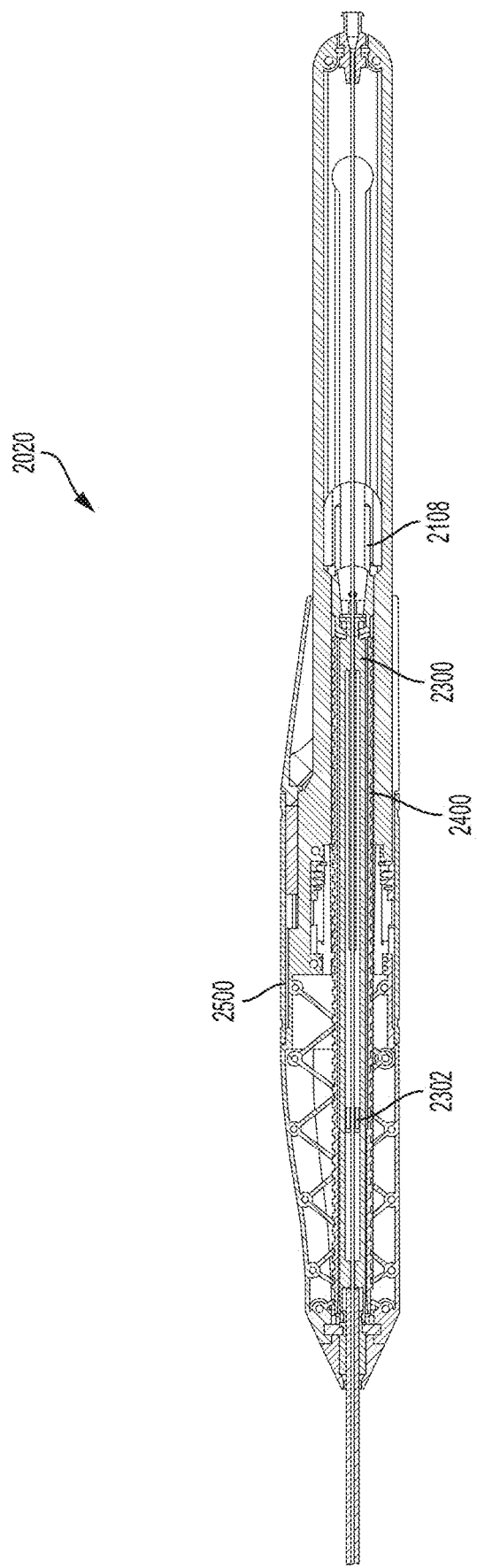

FIGS. 40-42 are longitudinal cross sections of the actuation portion 2020 at various stages of operation, according to some embodiments. As shown in FIG. 41, the nose cone 2266 is received over the connector hub 46, inserted into the distal end 2204 of the body portion 2200 of the housing assembly 2100, and the nose cone 2266 and the connector hub 46 are secured to the body portion 2200 using the distal lock clip 2264 which passes through the distal clip slot 2214 (FIG. 33) in the body portion 2200, the clip slot 2268 in the nose cone 2266 (FIG. 33), and over a clip slot 2808 (FIG. 40) in the connector hub 46 to secure the connector hub 46 and the nose cone 2266 to the housing assembly 2100. In turn, the proximal lock clip 2262 is received through the proximal clip slot 2216 (FIG. 33) in the body portion 2200 and over the clip slot 2806 in the proximal coupling 2802 of the catheter subassembly 2110 to secure the proximal coupling 2802, and thus the catheter subassembly 22110 to the housing assembly 2100.

Some examples of methods for operating the actuation portion 2020 are described below with reference to FIGS. 40-43. As shown in FIG. 41, the deployment knob 2500 has been rotated such that the drive member 2400 has been moved proximally to move the slider 2302 proximally, pulling the plurality of constraints 28 (FIG. 2) proximally. As shown in FIG. 14A, by pulling the plurality of constraints 28 proximally, the proximal constraining loop 195, the distal constraining loop 196, and the intermediate constraining loop 197 constrict about the prosthetic valve 16 to transition the valve to the compacted delivery state. The prosthetic valve 16 can then be retracted into the sheath 12 for intraluminal delivery to a desired treatment site, or location.

The prosthetic valve 16 (or other implantable device) can be extended from the sheath 12 and the deployment knob 2500 can be derotated, or rotated in the reverse direction to de-tension, or remove tension, on the plurality of constraints 28 with the drive member 2400 moving distally to the position shown in FIG. 42. In some examples, a bias of the prosthetic valve 16 to an expanded state causes provides a distal tension on the plurality of constraints 28, causing the slider 2302 to move distally with the drive member 2400 as previously described.

Figure 43:
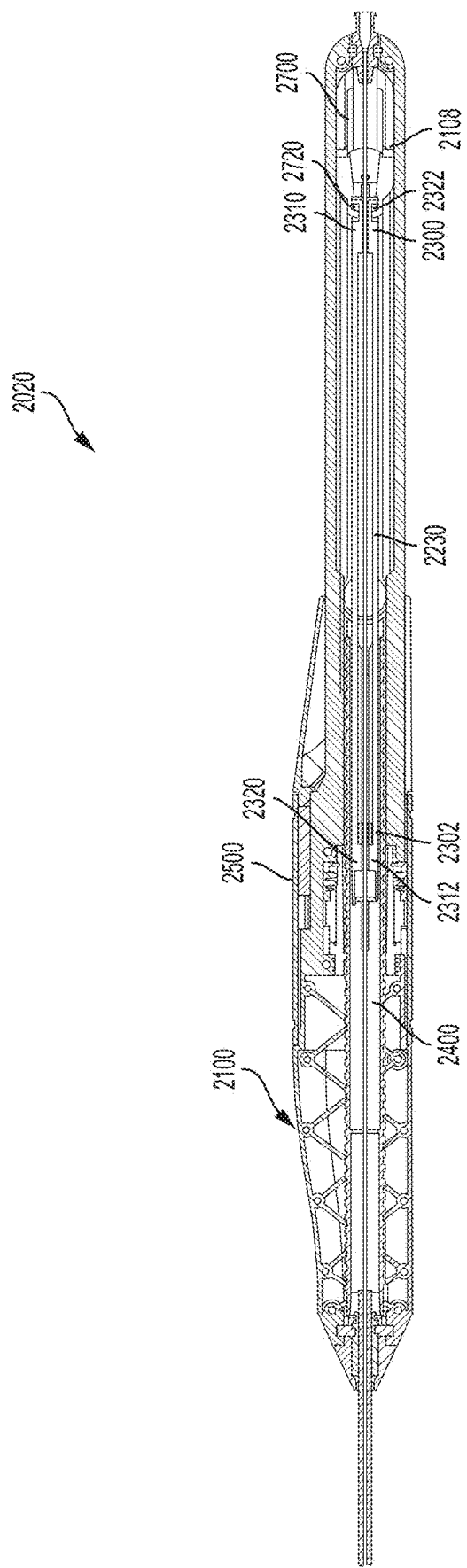

With the tension on the constraints 28 by the actuation portion 2020 reduced, or removed a release operation can be performed to transition the release assembly 2108 to the position shown in FIG. 43. In particular, the first button 2702 and the second button 2704 (FIG. 33) are depressed causing the first locking feature 2740 and the second locking feature 2742 (FIG. 39) to move into position to permit proximal movement of the lock flexure 2700. At the same time, the first flex arm 2710 and the second flex arm 2712 (FIG. 39) are flexed inwardly such that the grasping portions 2720 of each of the first flex arm 2710 and the second flex arm 2712 engage and grasp the retraction feature 2322 at the proximal end 2310 of the slide rail 2300. With the first locking feature 2740 and the second locking feature 2742 engaged with the edges of the release assembly track 2230, the release assembly 2108 is locked in an inwardly deflected position and thus locked to the slide rail 2300 by the grasping portions 2720. The release assembly 2108 is then slide proximally in the release assembly track 2230, pulling the slide rail 2300 proximally within the housing assembly 2100.

As the slide rail 2300 is pulled proximally, the proximal end 30a of the stake member 30 (FIG. 2) is retracted proximally and the distal constraining loop 196, the intermediate constraining loop 197, and the proximal constraining loop 195, and in particular the respective catches 192, 194, 190, are released from the stake member 30. Once the slide rail 2300 has been sufficiently retracted, the stop 2320 at the distal end 2312 of the slide rail 2300 engages the slider 2302 and begins retracting the slider 2302 proximally with the slide rail 2300. At this point, the plurality of constraints 28, now free from the stake member 30, retract from around the prosthetic valve 16, freeing the prosthetic valve (or other implantable device) from the delivery catheter 14 (e.g., at a desired delivery site).

Figure 44:
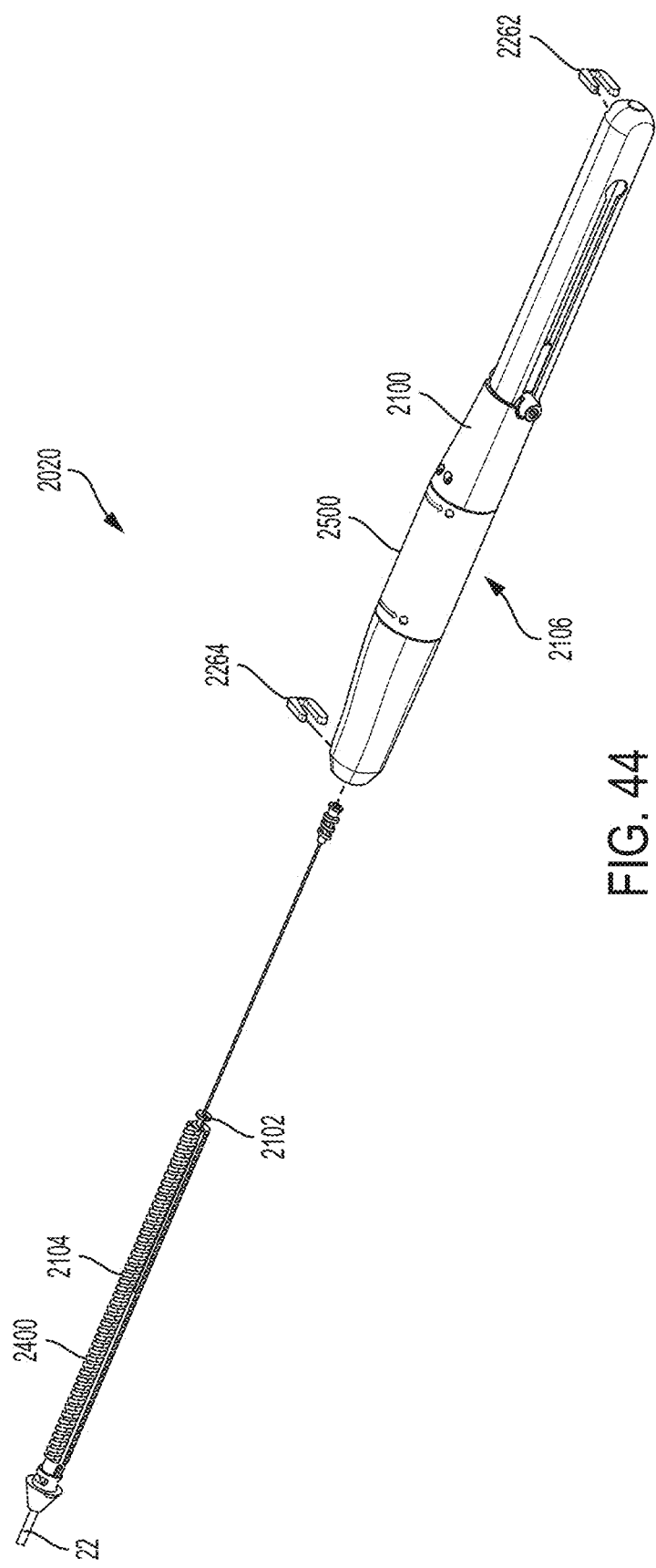

FIG. 44 is illustrative of still another operational method for the actuation portion 2020. For example, in the instance that a user (not shown) wishes to bypass the functionality of the actuation portion 2020, the user may remove the distal lock clip 2264 and the proximal lock clip 2262 from the housing assembly 2100 freeing the nose cone 2266, the connector hub 46, and the catheter subassembly 2110 from the housing assembly 2100. The deployment knob 2500 may then be rotated in the direction causing the drive member 2400 to move distally until the drive member 2400 is driven distally out of the nut portion 2502 (FIG. 38) and thus released from the actuation assembly 2106. The rack assembly 2102 and the drive assembly 2104 can then be pulled distally from the housing assembly 2100, along with the body portion 22 of the delivery catheter 14 (FIG. 2). The user may then directly access the plurality of constraints 28 and the stake member 30 (FIG. 2) as desired for manual manipulation. This may be desirable if delivery issues are encountered or that the user wishes to undertake other diagnostic or remedial measures. As previously stated, the foregoing actuation portion 2020 and associated methods is interchangeably usable with the delivery catheter 1014, including use with different implantable devices (e.g., stent grafts) as desired.

Figure 45:
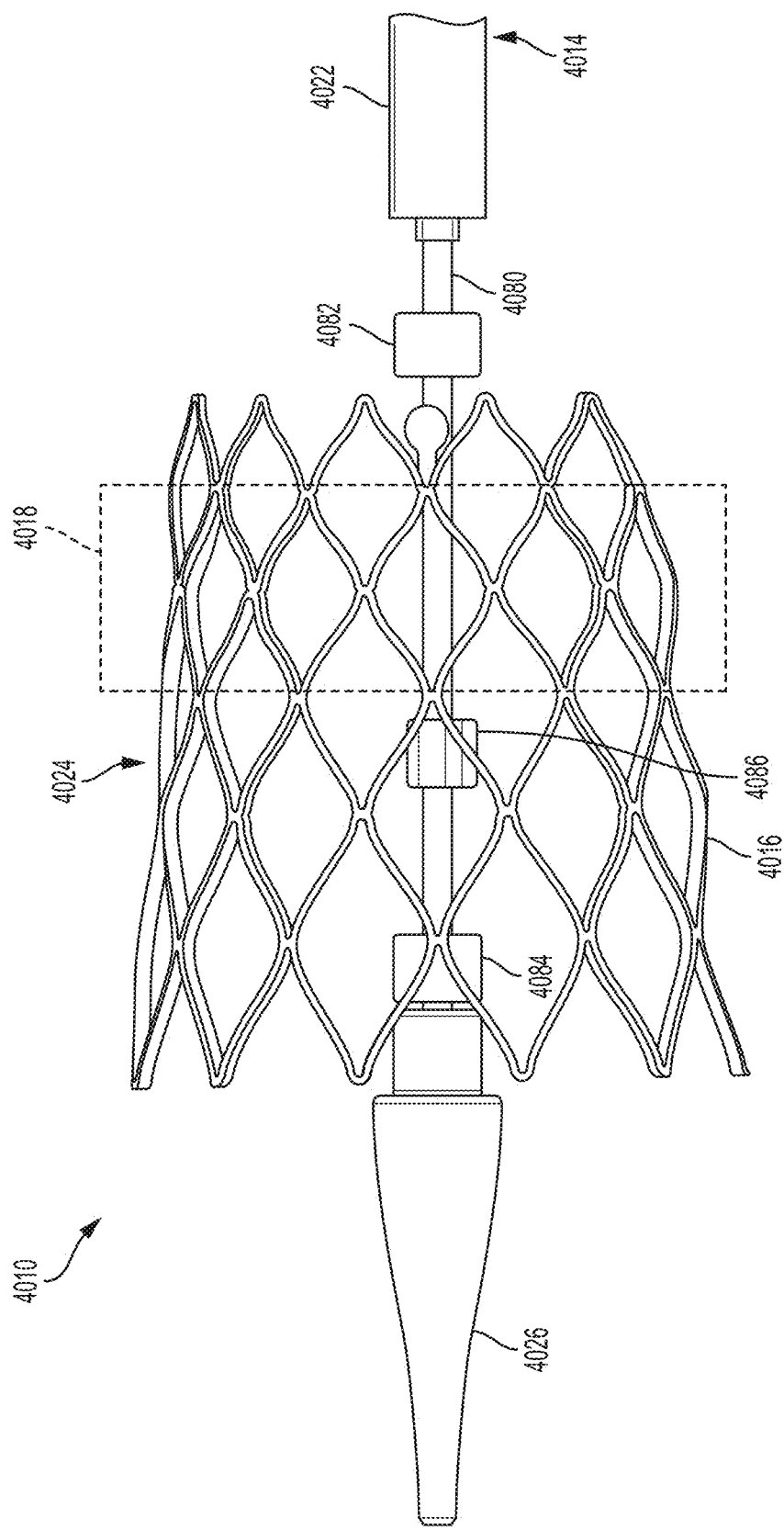
FIG. 45 is a side view of another transcatheter delivery system, according to some embodiments.
Figure 46:
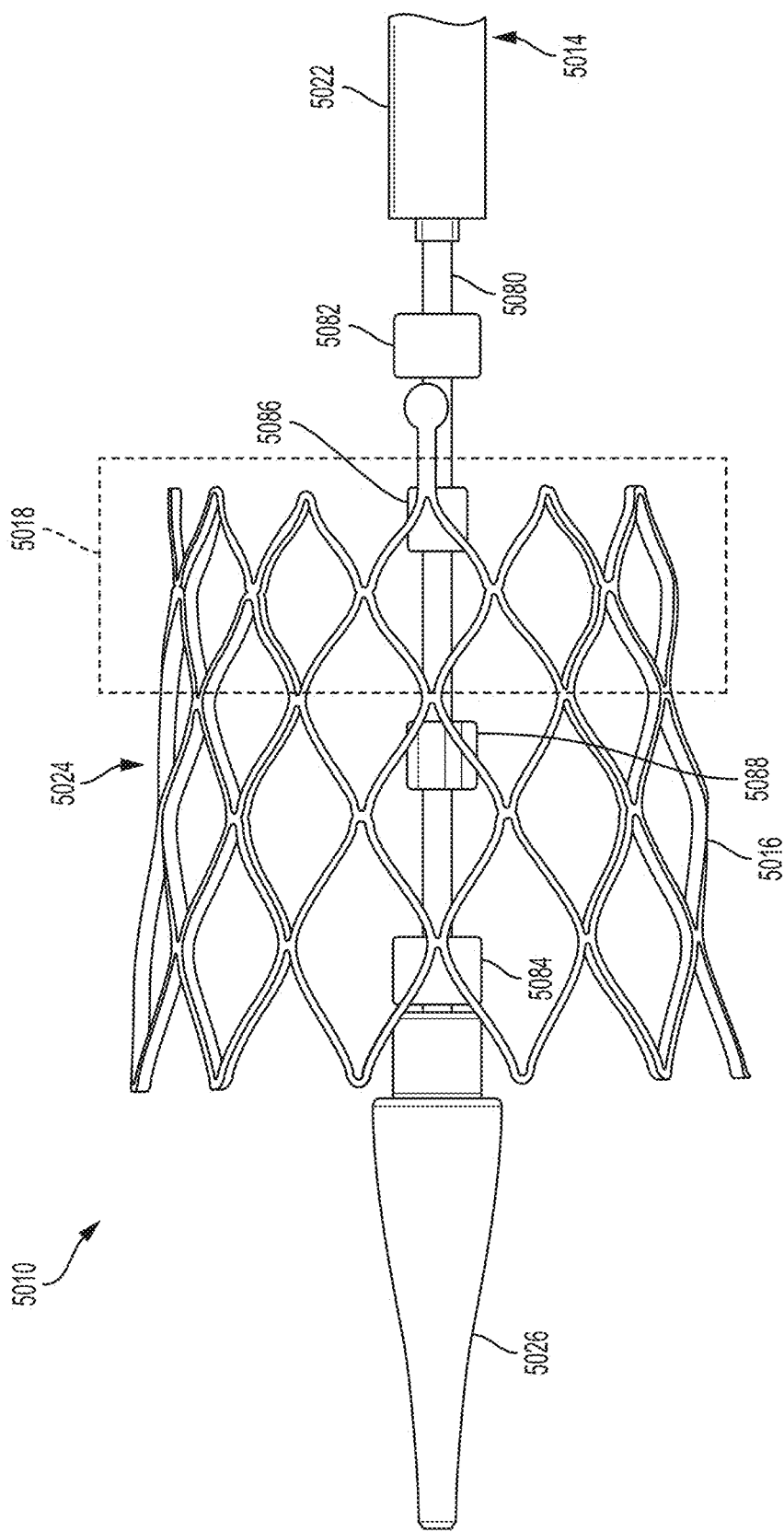
FIG. 46 is a side view of another transcatheter delivery system, according to some embodiments.
Figure 47:
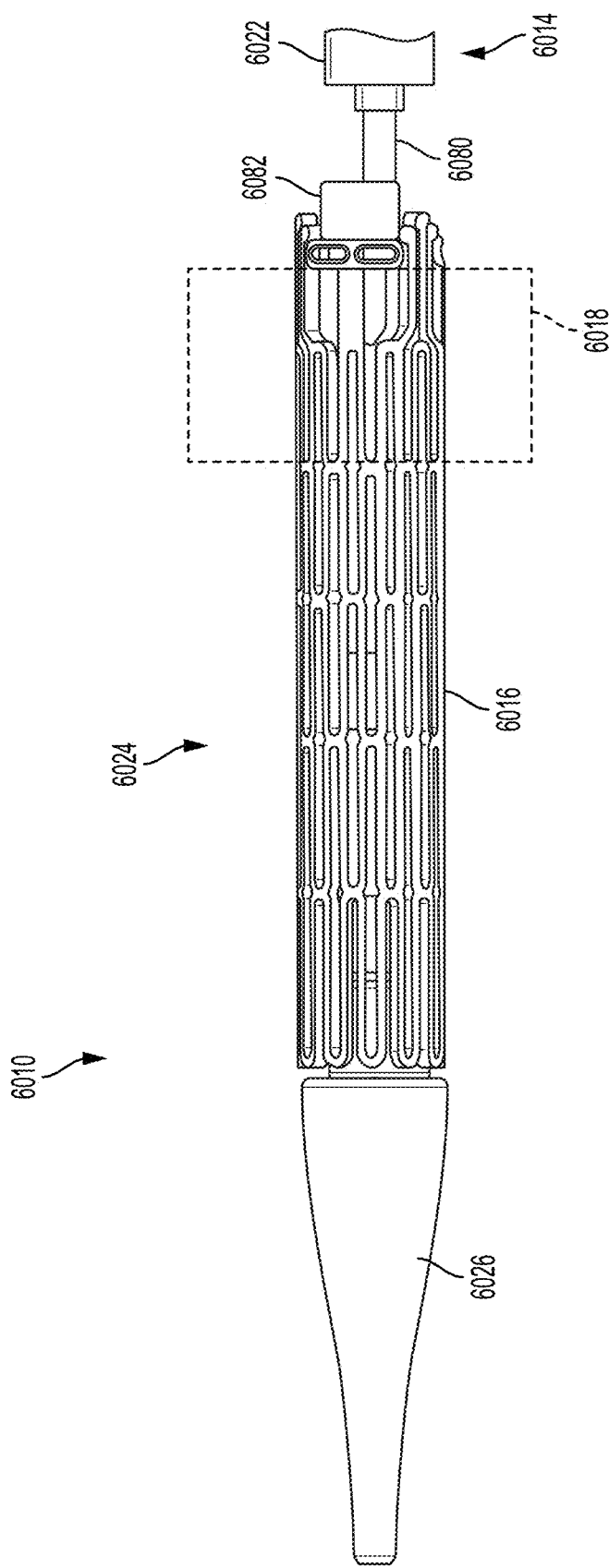
FIG. 47 is a side view of another transcatheter delivery system, according to some embodiments.

FIGS. 45 to 47 schematically illustrate various additional, optional positions of guides (e.g., proximal, distal, and/or intermediate guides) relative to various leaflet construct positions of prosthetic valves according to various examples. For reference, only frames are shown of the illustrative prosthetic valves for ease of visualization. For these additional examples, it should be understood that any of the leaflet constructs previously described (and associated prosthetic valves) may be positioned relative to the various guide locations in a similar manner to those locations shown in FIGS. 45 to 47.

FIG. 45 is a side view of another transcatheter delivery system 4010, in accordance with an embodiment. The delivery catheter 4014 includes a body portion 4022, a support portion 4024, a tip portion 4026, and a plurality of constraints (not shown). As shown, the implantable device 4016 may be a prosthetic valve including a leaflet construct (not shown) located inside, and supported by the support portion 4024 within the bounds of a leaflet region 4018. In some embodiments, the leaflet region 4018 is positioned along the support portion 4024 between the proximal guide 4082 and the distal guide 4084. For example, in some embodiments, the leaflet region 4018 does not extend longitudinally beyond the proximal guide 4082 and the distal guide 4084. In some embodiments, the leaflet region 4018 can be located between the intermediate guide 4086 and the proximal guide 4082, which may reduce or eliminate volume of the guide(s) in the leaflet region 4018 when the implantable device 4016 is compacted into the delivery state onto the support portion 4024.

FIG. 46 is a side view of another transcatheter delivery system 5010, in accordance with an embodiment. The delivery catheter 5014 includes a body portion 5022, a support portion 5024, a tip portion 5026, and a plurality of constraints (not shown). As shown, the support portion 5024 is generally configured to be received in an implantable device 5016 and to support the implantable device 5016 through delivery to, and deployment at a desired treatment location in a body of a patient (not shown). As shown, the support portion 5024 includes a shaft 5080, a proximal guide 5082, a first intermediate guide 5086, a second intermediate guide 5088, and a distal guide 5084.

As shown, the implantable device 5016 may be a prosthetic valve including a leaflet construct (not shown) located inside, and supported by the support portion 4024 within the bounds of in a leaflet region 5018. In some embodiments, the leaflet region 5018 is positioned on the support portion 5024 between the proximal guide 5082 and the second intermediate guide 5088. For example, in some embodiments, the leaflet region 5018 is positioned over the first intermediate guide 5086. In some embodiments, the first intermediate guide 5086 is generally smaller than the proximal guide 5082 and the second intermediate guide 5088 so that the volume of the first intermediate guide 5086 in the leaflet region 5018 is reduced when the implantable device 4016 is compacted into the delivery state onto the support portion 5024.

FIG. 47 is a side view of another transcatheter delivery system 6010, in accordance with an embodiment. The delivery catheter 6014 includes a body portion 6022, a support portion 6024, a tip portion 6026, and a plurality of constraints (not shown). As shown, the support portion 6024 is generally configured to be received in an implantable device 6016 and to support the implantable device 6016 through delivery to, and deployment at a desired treatment location in a body of a patient (not shown). As shown, the support portion 6024 includes a shaft 6080, a proximal guide 6082, an intermediate guide (not shown), and a distal guide (not shown).

As shown, the implantable device 6016 may include a frame portion and a valve including a leaflet construct (not shown) supported by the support portion 6024 at a position within the support portion 6024 corresponding to the boundaries of a leaflet region 6018. In some embodiments, the leaflet region 6018 is positioned on the support portion 6024 between the proximal guide 6082 and the distal guide 6084. For example, in some embodiments, the leaflet region 6018 does not extend longitudinally beyond the proximal guide 6082 and the distal guide 6084. In some embodiments, the leaflet region 6018 can be located between the intermediate guide 6086 and the proximal guide 6082, which may reduce or eliminate volume of the guide(s) in the leaflet region 6018. As shown, the implantable device 6016 may include a plurality of posts and thru-hole features (e.g., such as those of FIGS. 25A, 25B and 26 to 30) which may help permit movement of the proximal guide 6082 out of the leaflet region 6018 when the implantable device 4016 is compacted into the delivery state onto the support portion 6024.

Figure 48:
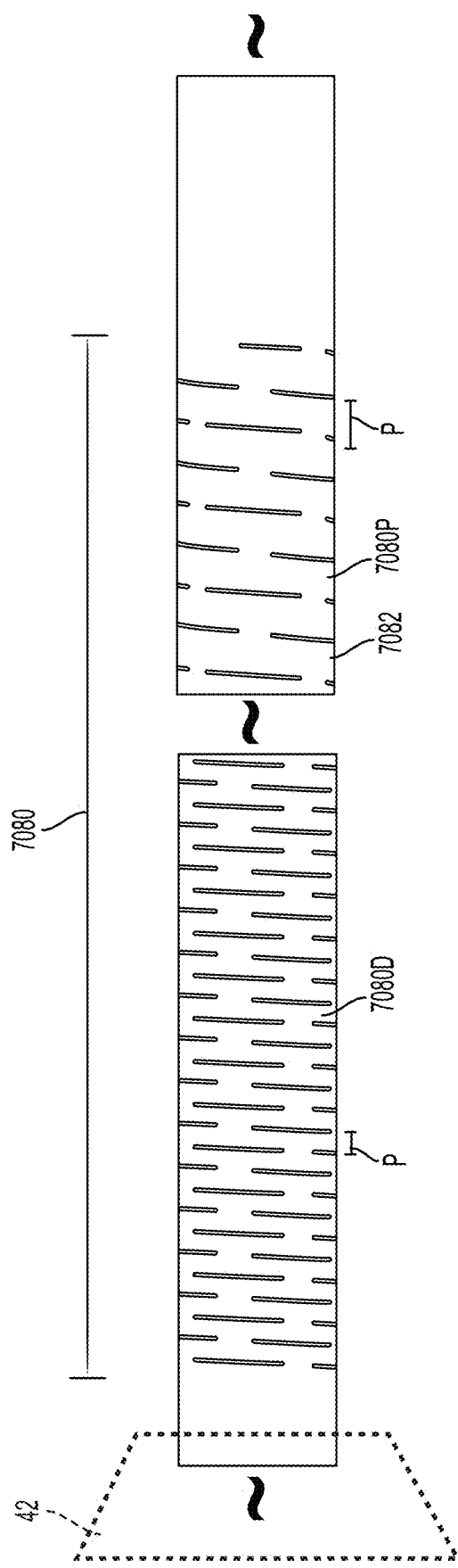
FIG. 48 illustrates enhanced flexibility features of a shaft of a delivery catheter, according to some embodiments.

FIG. 48 shows an enhanced flexibility portion 7080 of shaft 80 (FIG. 4), in accordance with various embodiments, which may be implemented for any of the other shafts previously described as well. As previously referenced, shaft 80 is formed as a hollow tube (e.g., hypotube), for example using nitinol, stainless steel, or other metallic or polymeric materials. In various examples, the shaft 80 is configured to receive a guidewire (not shown) for guiding the delivery catheter in which the shaft 80 is assembled to a desired treatment location. If desired, a liner (not shown) of a polymeric or other low friction material may be incorporated into the shaft 80 to reduce wear or interference with a guidewire (not shown) received within the shaft 80.

In some examples, the enhanced flexibility portion 7080 includes a cut pattern formed through the wall of the shaft 80 (e.g., laser cut). Although the pattern is described as being a "cut" pattern, any formation technique (e.g., etching) can be used to form the "cut" pattern. In the example of FIG. 48, the cut pattern is a broken, spiral pattern that leaves continuous longitudinal sections 7082 of the shaft 80. In different terms, the cut pattern includes intermittent, helical cuts that are staggered along the longitudinal length of the enhanced flexibility portion 7080. The cuts, or turns, define a period, or pitch P between adjacent cut lines in each of the proximal section 7080P and distal section 7080D of the enhanced flexibility portion 7080. As shown in FIG. 48, the pitch P may vary along the length of the enhanced flexibility portion 7080. For example, the pitch P of the spiral cut pattern may be greater in a proximal section 7080P, then smaller at a distal section 7080D. If desired the pitch may increase again at the end of the distal section 7080D to provide another transition to a continuous, or uncut portion at or adjacent the distal section 42 of the body portion 22 (FIG. 4).

In terms of where the enhanced flexibility portion 7080 begins and ends along the length of the shaft 80, that portion 7080 could form an entirety of the length of the shaft 80. However, in various examples, the enhanced flexibility portion 7080 begins at a location at or near the distal section 42 of the body portion 22. In one example, the enhanced flexibility portion extends for 11 cm in total length and initiates approximately 2 mm proximal to distal section 42 of the body portion 22, for example. In terms of pitch P, in one example the distal section 7080D has a pitch of 0.008 inches, with and an intermittent cut pattern of 3.5 cuts per revolution. In terms of the proximal portion 7080P, in one example, the pitch P transitions from pitch from 0.008 inches in the distal section 7080D to 0.016 inches in the proximal section 7080P with 3.5 cuts per revolution over 25 mm.

In another example, enhanced flexibility portion extends for 25 cm (e.g., beginning in a similar location to that described above) with an initial transition in the distal section 7080D extending for 25 mm at a pitch P changing from 0.016 inches to 0.008 inches with 3.5 cuts per rotation, then extending through the distal section 7080P for 150 mm at a pitch P of 0.008 inches with 3.5 cuts per rotation, and then for 25 mm at a pitch P changing from 0.008 inches to 0.016 inches with 3.5 cuts per rotation. Still another example includes an initial transition portion in the distal section 7080P extending for 25 mm at a pitch P changing from 0.016 inches to 0.008 inches with 3.5 cuts per rotation, then extending for 150 mm at a pitch P of 0.008 inches with 3.5 cuts per rotation, and then the proximal portion 7080P extending for 25 mm at a pitch changing from 0.008 inches to 0.016 inches with 3.5 cuts per rotation.

Though some specific examples of cut pattern dimensions are provided, it should be understood that these dimensions are provided for illustrative purposes, and should not be read as limiting design to a particular length, starting point, or ending point for the enhanced flexibility portion 7080. The foregoing dimensions are provided as examples for illustrative purposes, and though each of the foregoing dimensions, any combination of those dimensions, and any range between and including those dimensions are within the scope of inventive concepts described herein, additional dimensions are contemplated and are not outside the scope of such concepts.

In some examples, the shaft 7080 may include a liner (not shown) of a desired material (e.g., polyimide or fluoropolymer) lining the inside surface of the shaft 7080. In other examples, the shaft 7080 may be characterized by an absence of any liner and be continuously formed as a monolithic unit (e.g., entirely of a hypotube). The spiral cut pattern of FIG. 48 can be particularly advantageous in this respect, as the abrasion or other wear on a guidewire received within the shaft 7080 is not present with use of the spiral cut patterns disclosed herein.

Leaflet Materials

The leaflet constructs of the various embodiments may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In other examples, such leaflet constructs may be formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct further comprises a layer of an elastomer and/or an elastomeric material and/or a non-elastomeric material on the composite material. In accordance with some examples, the composite material comprises porous synthetic polymer membrane by weight in a range of about 10% to 90%

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluorom ethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluorom ethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluorom ethyl vinyl ether.

In some examples, the leaflet construct is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet construct further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer material made from porous ePTFE membrane, for instance as generally described in U.S. Pat. No. 7,306,729 to Bacino.

The expanded fluoropolymer membrane, used to form some of the composites described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

Frame Materials

The various frames can be etched, cut, laser cut, stamped, three-dimensional printed or wire wound, among other suitable processes. The frames can be self-expanding or balloon expandable (e.g., when configured for transcatheter implantation) or non-expandable (e.g., when configured for surgical implantation). The various frames can comprise materials, such as, but not limited to, any metallic or polymeric material, such as an elastically (e.g., nitinol) or plastically (e.g., stainless steel) deformable metallic or polymeric material that is generally biocompatible. Other materials suitable for any of the frames described herein include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame as described herein.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Inventive concepts have been described above both generically and with regard to specific embodiments. It will be apparent to those skilled in the art that various modifications and variations can be made in the embodiments without departing from the scope of the disclosure. Thus, it is intended that the disclosure is inclusive of modifications and variations provided they come within the scope of the appended claims.

What is claimed is:

1. A transcatheter delivery system including an actuation portion for a delivery catheter, the actuation portion being configured to tension and de-tension one or more device constraints, the actuation portion comprising:
   a body portion;
   a constraint guide coupled to the body portion;
   at least one constraint maintained by the constraint guide;
   a stake member, the at least one constraint releasably secured to the stake member;
   a housing assembly coupled to the body portion;
   a rack assembly received in the housing assembly and including a slide rail secured to the stake member and slidably receiving a slider secured to the at least one constraint;
   a drive assembly slidably received over the slide rail and engageable with the slider to longitudinally translate the slider within the slide rail;
   an actuation assembly including a rotatable deployment knob and configured to longitudinally translate the drive assembly along the slide rail; and
   a release assembly configured to longitudinally translate the slide rail to longitudinally translate the stake member.

2. The transcatheter delivery system of claim 1, wherein the at least one constraint includes a catch releasably secured to the stake member.

3. A transcatheter delivery system including a delivery catheter, the delivery catheter comprising:
   a body portion,
   a support portion extending from the body portion, the support portion configured to support an implantable device;
   a stake member;
   at least one constraint configured to be tensioned to the stake member to maintain the implantable device in a compacted delivery configuration, to be de-tensioned from the stake member to permit the implantable device to be transitioned to an expanded deployed configuration, and to be released from the stake member to release the implantable device from the delivery catheter; and an actuation portion configured to tension the at least one constraint, to de-tension the at least one constraint, and to release the at least one constraint from the stake member, the actuation portion including, a housing assembly coupled to the body portion, a rack assembly received in the housing assembly and including a slide rail secured to the stake member and slidably receiving a slider secured to the at least one constraint, a drive assembly slidably received over the slide rail and engageable with the slider to longitudinally translate the slider within the slide rail, an actuation assembly including a rotatable deployment knob and configured to longitudinally translate the drive assembly along the slide rail, and a release assembly configured to longitudinally translate the slide rail to longitudinally translate the stake member.

4. The transcatheter delivery system of claim 3, wherein the at least one constraint includes a catch releasably secured to the stake member.

5. The transcatheter delivery system of claim 3, wherein the drive assembly includes a clutch.

6. The transcatheter delivery system of claim 5, wherein the clutch is a ratchet clutch.

7. The transcatheter delivery system of claim 3, wherein the body portion, the rack assembly, and the drive assembly are releasably secured to the housing assembly by one or more clips, such that the rack assembly and the drive assembly are configured to be released from the drive assembly and the housing and slid longitudinally out from a distal end of the housing assembly.

8. The transcatheter delivery system of claim 3, further comprising an implantable device maintained in a compacted delivery configuration on the support portion by the at least one constraint.

9. The transcatheter delivery system of claim 8, wherein the implantable device is a prosthetic valve.

10. The transcatheter delivery system of claim 3, wherein the delivery catheter includes at least two constraints, each constraint configured to be tensioned to the stake member to maintain the implantable device in the compacted delivery configuration, de-tensioned from the stake member to permit the implantable device to be transitioned to the expanded deployed configuration, and to be released from the stake member to release the implantable device from the delivery catheter.

11. The transcatheter delivery system of claim 3, wherein the actuation assembly further includes a nut portion and a gear portion defining a clutch arrangement such that rotation of the gear portion results in rotation of the nut portion up until a torsional limit is reached at which point the gear portion is allowed to slip against the nut portion.

12. The transcatheter delivery system of claim 11, wherein the nut portion is threaded onto the drive assembly.

13. The transcatheter delivery system of claim 12, further comprising a shaft extending through the body portion and the support portion, the shaft including an enhanced flexibility portion proximal to the support portion, the enhanced flexibility portion including a distal section having a cut pattern characterized by a first pitch and a proximal section having a cut pattern characterized by a second pitch that is greater than the first pitch.

14. The transcatheter delivery system of claim 13, wherein the distal section includes a distal transition portion having cut pattern characterized by a third pitch that is greater than the first pitch.

15. The transcatheter delivery system of claim 11, wherein the gear portion includes a plurality of teeth engaged with a plurality of teeth of the deployment knob.

16. A transcatheter delivery system including an actuation assembly for a delivery catheter, the actuation assembly being configured to tension and de-tension one or more device constraints, the actuation assembly comprising:

a body portion;

a constraint guide coupled to the body portion;

at least one constraint maintained by the constraint guide;

a stake member, the at least one constraint releasably secured to the stake member;

a housing assembly coupled to the body portion;

a rack assembly received in the housing assembly and including a slide rail secured to the stake member and slidably receiving a slider secured to the at least one constraint;

a drive assembly slidably received over the slide rail and engageable with the slider to longitudinally translate the slider within the slide rail;

a nut portion threaded onto the drive assembly and a gear portion defining a clutch arrangement such that rotation of the gear portion results in rotation of the nut portion up until a torsional limit is reached at which point the gear portion is allowed to slip against the nut portion; and an actuation assembly including a rotatable deployment knob and configured to longitudinally translate the drive assembly along the slide rail.

17. The transcatheter delivery system of claim 16, wherein the clutch arrangement is a ratchet clutch arrangement.

* * * * *